United States Patent
Nakamura et al.

(10) Patent No.: US 9,782,392 B2
(45) Date of Patent: Oct. 10, 2017

(54) AZAINDOLE DERIVATIVE

(71) Applicant: TAIHO PHARMACEUTICAL CO., LTD., Chiyoda-ku (JP)

(72) Inventors: Masayuki Nakamura, Tsukuba (JP); Hiroyoshi Yamanaka, Moriya (JP); Kazuaki Shibata, Moriya (JP); Morihiro Mitsuya, Tsukuba (JP); Takafumi Harada, Tsukuba (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

(21) Appl. No.: 15/404,253

(22) Filed: Jan. 12, 2017

(65) Prior Publication Data
US 2017/0119743 A1 May 4, 2017

Related U.S. Application Data

(63) Continuation of application No. 15/112,070, filed as application No. PCT/JP2015/053031 on Feb. 4, 2015, now Pat. No. 9,676,773.

(30) Foreign Application Priority Data
Feb. 4, 2014 (JP) .................................. 2014-019584

(51) Int. Cl.
| | | |
|---|---|---|
| C07D 401/14 | (2006.01) |
| A61K 31/437 | (2006.01) |
| A61K 31/444 | (2006.01) |
| A61K 31/5377 | (2006.01) |
| A61K 31/695 | (2006.01) |

(52) U.S. Cl.
CPC .......... A61K 31/437 (2013.01); A61K 31/444 (2013.01); A61K 31/5377 (2013.01); A61K 31/695 (2013.01)

(58) Field of Classification Search
CPC ............................ C07D 401/14; A61K 31/437
USPC .......................................... 546/119; 514/303
See application file for complete search history.

(56) References Cited

U.S. PATENT DOCUMENTS

| | | |
|---|---|---|
| 2005/0137201 A1 | 6/2005 | Aronov et al. |
| 2006/0003968 A1 | 1/2006 | Green et al. |
| 2006/0122213 A1 | 6/2006 | Pierard et al. |
| 2007/0135466 A1 | 6/2007 | Ledeboer et al. |
| 2007/0203142 A1 | 8/2007 | Farmer et al. |
| 2009/0264399 A1 | 10/2009 | Inoue et al. |
| 2010/0069358 A1 | 3/2010 | Graczyk et al. |

FOREIGN PATENT DOCUMENTS

| | | |
|---|---|---|
| CN | 102372717 A | 3/2012 |
| JP | 2007-504252 A | 3/2007 |
| JP | 2008-513352 A | 5/2008 |
| JP | 2008-545660 A | 12/2008 |
| JP | 2010-517980 A | 5/2010 |
| WO | 2005/028475 A2 | 3/2005 |
| WO | 2006/004984 A1 | 1/2006 |
| WO | 2006/127587 A1 | 11/2006 |
| WO | WO 2012/158785 A1 | 11/2012 |
| WO | WO 2013/085802 A1 | 6/2013 |

OTHER PUBLICATIONS

Kamran Goreschi, et al., "Janus kinases in immune cell signaling", Immunological Reviews 2009, vol. 228, 2009 (15 pages).
Melanie G. Cornejo, et al., "JAK3: A two-faced player in hematological disorders", Elsevier, The International Journal of Biochemistry & Cell Biology, vol. 41, 2009, (4 pages).
Anastassios C. Papageorgiou, et al., "Is JAK3 a new drug target for immunomodulation-based therapies?", TRENDS in Pharmacological Sciences, vol. 25, No. 11, Nov. 2004, (5 pages).
Seiji Yokoyama, et al., "Tofacitinib, a Janus kinase inhibitor demonstrates efficacy in an IL-15 transgenic mouse model that recapitulates pathologic manifestations of celiac disease", Journal of Clinical Immunology, 33(3): Apr. 2013, (14 pages).
Wei Xu, et al., "Hemagglutinin from the H5N1 Virus Activates Janus Kinase 3 to Dysregulate Innate Immunity", PLoS One, vol. 7, Issue 2, 2012, (11 pages).
Ghee Chong Koo, et al., "Janus Kinase 3-Activating Mutations Identified in Natural Killer/T-cell Lymphoma", Cancer Discovery, 2012, (8 pages).
J.J. O'Shea, "Targeting the Jak/STAT pathway for immunosuppression", Ann Rheum Dis, vol. 63, 2004, (6 pages).
Byung Il Lee, et al., "Pyrogallin, an ATP-Competitive Inhibitor of JAK3", Bull. Korean Chem. Soc., vol. 32, No. 3, 2011, (3 pages).
Mark E. Flanagan, et al., "Discovery of CP-690,550: A Potent and Selective Janus Kinase (JAK) Inhibitor for the Treatment of Autoimmune Diseases and Organ Transplant Rejection", Journal of Medical Chemistry, vol. 53, No. 24, 2010, (17 pages).

(Continued)

*Primary Examiner* — Niloofar Rahmani
(74) *Attorney, Agent, or Firm* — Oblon, McClelland, Maier & Neustadt, L.L.P.

(57) ABSTRACT

A method for treating rheumatoid arthritis, multiple sclerosis, or a disease involving JAK3, including administering a compound of the formula (I) or a salt thereof to a subject

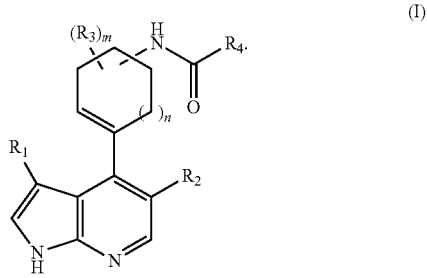

(I)

22 Claims, No Drawings

(56) References Cited

OTHER PUBLICATIONS

Japanese Office Action issued on Apr. 5, 2016 for JP 2015-560995 with partial English translation (3 pages).
International Search Report issued on Apr. 21, 2015 for PCT/JP2015/053031 filed on Feb. 4, 2015.
European Search Report issued Jan. 19, 2017 in Patent Application No. 15746235.9.

AZAINDOLE DERIVATIVE

CROSS REFERENCES TO RELATED APPLICATIONS

This application is a continuation of U.S. patent application Ser. No. 15/112,070, which is the National Stage of the International Patent Application No. PCT/JP2015/053031, filed Feb. 4, 2015, the disclosures of which are incorporated herein by reference in their entireties. This application claims priority to Japanese Application No. 2014-019584, filed Feb. 4, 2014.

TECHNICAL FIELD

The present invention relates to a novel azaindole derivative having a selective JAK3-inhibitory effect and a pharmaceutical composition containing the azaindole derivative as an active ingredient.

BACKGROUND ART

It has been known that JAK3, as well as JAK1, JAK2 and TYK2, is a non-receptor tyrosine kinase belonging to a JAK family, and that JAK3 is involved in the signaling of various cytokines.

JAK1, JAK2 and TYK2 are expressed in a wide range of tissues, whereas the expression of JAK3 is mainly limited to lymphocytes such as T cells, B cells, and natural killer cells. JAK1- and JAK2-deficient mice are embryonic lethal, or die soon after the birth, whereas JAK3-deficient mice or humans develop severe combined immunodeficiency due to the lymphocyte dysfunction.

It is assumed that a JAK3 inhibitor inhibit the signals of six types of cytokines (i.e., IL-2, IL-4, IL-7, IL-9, IL-15, and IL-21), so as to specifically suppress the function of lymphocytes such as T cells or B cells, which play an important role in an immune system. Thus, it is anticipated that such a JAK3 inhibitor can be an effective therapeutic agent for diseases associated with activation of the aforementioned cells, having minimum expression of side effects (Non Patent Literatures 1 and 2).

It has been reported that examples of the disease, which can be treated with the JAK3 inhibitor, include autoimmune disease (rheumatoid arthritis, systemic lupus erythematosus, scleroderma, polymyositis-dermatomyositis, Sjogren's syndrome, Behcet's disease, etc.), allergic disease (bronchial asthma, allergic rhinitis/hay fever, atopic dermatitis, food allergy, anaphylaxis, drug allergy, hives, conjunctivitis, etc.), nervous system disease (multiple sclerosis, Alzheimer's disease, etc.), inflammatory bowel disease (ulcerative colitis, Crohn's disease), psoriasis, contact dermatitis, diabetes, celiac disease, viral infectious disease, acute respiratory distress syndrome (ARDS), graft-versus-host disease (GVHD), transplant rejection, hematologic malignancy (lymphoma, leukemia), and other malignant tumors (Non Patent Literatures 3 to 8).

Moreover, Tofacitinib (Pfizer), a JAK3 inhibitor, has been used as a therapeutic agent for rheumatoid arthritis in clinical sites. It has been reported that this JAK3 inhibitor has low selectivity to JAK3, and thus that side effects (lipid rise, anemia, neutropenia, immunosuppression, etc.) are caused by inhibition of JAK1 and JAK2 (Non Patent Literature 9).

Furthermore, an azaindole derivative having a cyclic substituent at 4-position and an azaindole derivative having cyclic substituents at 3- and 5-positions have been reported as JAK inhibitors. However, these azaindole derivatives have low selectivity to JAK3, and the inhibitory activity thereof is not sufficient (Patent Literatures 1 and 2).

CITATION LIST

Patent Literature

[Patent Literature 1] International Publication No. WO 2006/127587

[Patent Literature 2] International Publication No. WO 2006/004984

Non Patent Literature

[Non Patent Literature 1] Immunol Rev. 2009; 228 (1): 273-87.

[Non Patent Literature 2] Int J Biochem Cell Biol. 2009; 41 (12): 2376-9.

[Non Patent Literature 3] Trends Pharmacol Sci. 2004; 25 (11): 558-62.

[Non Patent Literature 4] J Clin Immunol. 2013; 33 (3): 586-94.

[Non Patent Literature 5] PLoS One. 2012; 7 (2): e31721.

[Non Patent Literature 6] Cancer Discov. 2012; 2 (7): 591-7.

[Non Patent Literature 7] Ann Rheum Dis. 2004; 63 (Suppl II): ii67-ii71.

[Non Patent Literature 8] Bull Korean Chem Soc. 2011; 32 (3): 1077-1079.

[Non Patent Literature 9] J Med Chem. 2010; 53 (24): 8468-84.

SUMMARY OF INVENTION

Technical Problem

It is an object of the present invention to provide a novel compound, which selectively and strongly inhibits JAK3, or a salt thereof, and a pharmaceutical composition containing the same.

Solution to Problem

As a result of intensive studies directed toward achieving the aforementioned object, the present inventors have found that a compound group, which contains azaindole as a basic structure, has a cycloalkenyl group at 4-position, and further has a cyclic substituent at 3-position, has a selective inhibitory activity on JAK3. Moreover, the inventors have found that the compound of the present invention has an excellent effect to suppress the growth of human peripheral blood mononuclear cells (hereinafter referred to as PBMC), and have then confirmed that the compound is useful as a pharmaceutical agent for treating various diseases involving JAK3 (in particular, autoimmune disease). Furthermore, the inventors have confirmed that the compound of the present invention has excellent oral absorbability and is useful as an oral pharmaceutical product, thereby completing the present invention.

The present invention provides the following [1] to [21].

[1] A compound of the following formula (I), or a salt thereof:

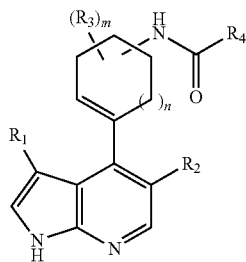

where
R$_1$ represents an optionally substituted C$_4$-C$_{10}$ cycloalkyl group, an optionally substituted C$_4$-C$_{10}$ cycloalkenyl group, an optionally substituted C$_4$-C$_{10}$ cycloalkynyl group, an optionally substituted C$_6$-C$_{14}$ aromatic hydrocarbon group, or an optionally substituted 4- to 10-membered saturated or unsaturated heterocyclic group;

R$_2$ represents a hydrogen atom, a halogen atom, a hydroxy group, a cyano group, a nitro group, —C(=O)R$_x$, —C(=O)OR$_x$, —C(=O)N(R$_x$)(R$_y$), —N(R$_x$)(R$_y$), —NR$_x$C(=O)R$_y$, —NR$_x$S(=O)$_2$R$_y$, —NR$_x$C(=O)OR$_y$, —NR$_x$C(=O)N(R$_y$)(R$_z$), —NR$_x$S(=O)$_2$N(R$_y$)(R$_z$), —OC(=O)R$_x$, —OC(=O)OR$_x$, —OC(=O)N(R$_x$)(R$_y$), —SR$_x$, —S(=O)$_2$R$_x$, —S(=O)$_2$OR$_x$, an optionally R$_b$-substituted C$_1$-C$_6$ alkyl group, an optionally R$_b$-substituted C$_2$-C$_6$ alkenyl group, an optionally R$_b$-substituted C$_2$-C$_6$ alkynyl group, an optionally R$_b$-substituted C$_1$-C$_6$ alkoxy group, an optionally R$_c$-substituted C$_3$-C$_{10}$ cycloalkyl group, an optionally R$_c$-substituted C$_6$-C$_{14}$ aromatic hydrocarbon group, or an optionally R$_c$-substituted 4- to 10-membered saturated or unsaturated heterocyclic group;

R$_3$ represents a halogen atom, an amino group, a hydroxy group, a cyano group, a nitro group, a C$_1$-C$_6$ alkyl group, a C$_2$-C$_6$ alkenyl group, a C$_2$-C$_6$ alkynyl group, or a C$_1$-C$_6$ alkoxy group;

R$_4$ represents an optionally R$_b$-substituted C$_2$-C$_6$ alkenyl group or an optionally R$_b$-substituted C$_2$-C$_6$ alkynyl group;

R$_b$ represents a halogen atom, an amino group, a hydroxy group, a cyano group, a nitro group, a C$_1$-C$_6$ alkoxy group, a di- or mono-(C$_1$-C$_6$ alkyl)amino group, or a 4- to 10-membered saturated or unsaturated heterocyclic group;

R$_c$ represents a halogen atom, an amino group, a hydroxy group, a cyano group, a nitro group, an oxo group, an imino group, an N-oxide group, a C$_1$-C$_6$ alkyl group, a C$_2$-C$_6$ alkenyl group, a C$_2$-C$_6$ alkynyl group, a C$_1$-C$_6$ alkoxy group, or a di- or mono-(C$_1$-C$_6$ alkyl)amino group;

R$_x$, R$_y$ and R$_z$, which are the same or different, each represent a hydrogen atom, a C$_1$-C$_6$ alkyl group, a C$_1$-C$_6$ haloalkyl group, a C$_2$-C$_6$ alkenyl group, a C$_2$-C$_6$ alkynyl group, a C$_3$-C$_{10}$ cycloalkyl group, a C$_6$-C$_{14}$ aromatic hydrocarbon group, or a 4- to 10-membered saturated or unsaturated heterocyclic group;

m represents an integer of 0 to 3; and
n represents an integer of 0 to 2.

[2] The compound according to [1] or a salt thereof, where a group with which the C$_4$-C$_{10}$ cycloalkyl group, C$_4$-C$_{10}$ cycloalkenyl group, C$_4$-C$_{10}$ cycloalkynyl group, C$_6$-C$_{14}$ aromatic hydrocarbon group or 4- to 10-membered saturated or unsaturated heterocyclic group, which is represented by R$_1$, is optionally substituted is R$_a$, and the R$_a$ represents a halogen atom, a hydroxy group, a cyano group, a nitro group, an oxo group, an N-oxide group, —C(=O)R$_x$, —C(=O)OR$_x$, —C(=O)N(R$_x$)(R$_y$), —C(=O)SR$_x$, —C(=S)OR$_x$, —C(=O)ON(R$_x$)(R$_y$), —N(R$_x$)(R$_y$), —NR$_x$C(=O)R$_y$, —NR$_x$S(=O)$_2$R$_y$, —NR$_x$C(=O)OR$_y$, —NR$_x$C(=O)N(R$_y$)(R$_z$), —NR$_x$S(=O)$_2$N(R$_y$)(R$_z$), —N(R$_x$)—OR$_y$, =NR$_x$, =N—OR$_x$, —OC(=O)R$_x$, —OC(=S)R$_x$, —OC(=O)OR$_x$, —OC(=O)N(R$_x$)(R$_y$), —OC(=S)OR$_x$, —SR$_x$, —S(=O)$_2$R$_x$, —S(=O)$_2$OR$_x$, —S(=O)$_2$N(R$_x$)(R$_y$), an optionally R$_b$-substituted C$_1$-C$_6$ alkyl group, an optionally R$_b$-Substituted C$_2$-C$_6$ alkenyl group, an optionally R$_b$-substituted C$_2$-C$_6$ alkynyl group, an optionally R$_b$-substituted C$_1$-C$_6$ alkoxy group, an optionally R$_c$-substituted C$_3$-C$_{10}$ cycloalkyl group, an optionally R$_c$-substituted C$_6$-C$_{14}$ aromatic hydrocarbon group, or an optionally R$_c$-substituted 4- to 10-membered saturated or unsaturated heterocyclic group.

[3] The compound according to [1] or [2], or a salt thereof, where R$_1$ represents an optionally R$_a$-substituted C$_5$-C$_7$ cycloalkenyl group, an optionally R$_a$-substituted C$_6$-C$_{10}$ aromatic hydrocarbon group, or an optionally R$_a$-substituted monocyclic 4- to 7-membered unsaturated heterocyclic group having 1 to 3 heteroatoms selected from the group consisting of N, S and O.

[4] The compound according to any one of [1] to [3] above, or a salt thereof, wherein R$_1$ represents a cyclopentenyl group, a cyclohexenyl group, a phenyl group, a furanyl group, a 1H-pyrazolyl group, a thiazolyl group, an oxazolyl group, an isoxazolyl group, a 1,3,4-thiadiazolyl group, a 1,2,4-oxadiazolyl group, a 1,3,4-oxadiazolyl group, a pyridyl group, a dihydropyranyl group, a dihydrofuranyl group, or a 4,5-dihydro-1,3,4-oxadiazolyl group, and the cycloalkenyl group, aromatic hydrocarbon group, and unsaturated heterocyclic group are optionally substituted with R$_a$.

[5] The compound according to any one of [1] to [4] above, or a salt thereof, where R$_1$ represents a cyclopentenyl group, a cyclohexenyl group, a phenyl group, a furanyl group, a 1H-pyrazolyl group, a thiazolyl group, an oxazolyl group, an isoxazolyl group, a 1,3,4-thiadiazolyl group, a 1,2,4-oxadiazolyl group, a 1,3,4-oxadiazolyl group, a pyridyl group, a dihydropyranyl group, a dihydrofuranyl group, or a 4,5-dihydro-1,3,4-oxadiazolyl group, and the cycloalkenyl group, aromatic hydrocarbon group, and unsaturated heterocyclic group are optionally substituted with a group selected from the group consisting of a halogen atom, an amino group, a hydroxy group, an oxo group, an N-oxide group, a formyl group, a C$_1$-C$_6$ alkyl group (which is optionally substituted with a group selected from the group consisting of a hydroxy group and a di- or mono-(C$_1$-C$_6$ alkyl)amino group), a C$_1$-C$_6$ alkoxy group (which is optionally substituted with a halogen atom), and a 4- to 10-membered saturated heterocyclic group.

[6] The compound according to any one of [1] to [5], or a salt thereof, where R$_1$ represents a cyclopentenyl group; a cyclohexenyl group; a phenyl group; a furanyl group, which is optionally substituted with a group selected from the group consisting of a formyl group and a C$_1$-C$_6$ alkyl group (which is optionally substituted with a group selected from the group consisting of a hydroxy group and a di- or mono-(C$_1$-C$_6$ alkyl)amino group); a 1H-pyrazolyl group, which is optionally substituted with a group selected from the group consisting of a C$_1$-C$_6$ alkyl group and a 4- to 10-membered saturated heterocyclic group; a thiazolyl group; an oxazolyl group; an isoxazolyl group;

a 1,3,4-thiadiazolyl group; a 1,2,4-oxadiazolyl group; a 1,3,4-oxadiazolyl group, which is optionally substituted with a $C_1$-$C_6$ alkyl group; a pyridyl group, which is optionally substituted with a group selected from the group consisting of a halogen atom, an amino group, a hydroxy group, an N-oxide group, a $C_1$-$C_6$ alkyl group (which is optionally substituted with a hydroxy group), and a $C_1$-$C_6$ alkoxy group (which is optionally substituted with a halogen atom); a dihydropyranyl group; a dihydrofuranyl group; or a 4,5-dihydro-1,3,4-oxadiazolyl group, which is optionally substituted with a group selected from the group consisting of an oxo group and a $C_1$-$C_6$ alkyl group.

[7] The compound according to any one of [1] to [6], or a salt thereof, where $R_2$ represents a hydrogen atom, a cyano group, —C(=O)$OR_x$, —C(=O)N($R_x$)($R_y$), an optionally $R_b$-substituted $C_1$-$C_6$ alkyl group, an optionally $R_b$-substituted $C_1$-$C_6$ alkoxy group, or an optionally $R_c$-substituted monocyclic 4- to 7-membered unsaturated heterocyclic group having 1 to 3 heteroatoms selected from the group consisting of N, S and O.

[8] The compound according to any one of [1] to [7], or a salt thereof, where $R_2$ represents a hydrogen atom; a cyano group; a ($C_1$-$C_6$ alkoxy)carbonyl group; a carbamoyl group; a di- or mono-($C_1$-$C_6$ alkyl)carbamoyl group; a $C_1$-$C_6$ alkyl group, which is optionally substituted with a group selected from the group consisting of a hydroxy group, a $C_1$-$C_6$ alkoxy group, a di- or mono-($C_1$-$C_6$ alkyl)amino group, and a 4- to 10-membered saturated heterocyclic group; a $C_1$-$C_6$ alkoxy group; or a monocyclic 5- or 6-membered completely unsaturated heterocyclic group having 1 to 3 N atoms, which is optionally substituted with a $C_1$-$C_6$ alkyl group.

[9] The compound according to any one of [1] to [8] above, or a salt thereof, where m represents 0, n represents 0 or 1, $R_4$ represents a $C_2$-$C_6$ alkenyl group or a $C_2$-$C_6$ alkynyl group, and in the formula (I), the following structure:

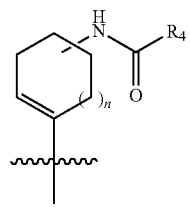

is any one of the following structures:

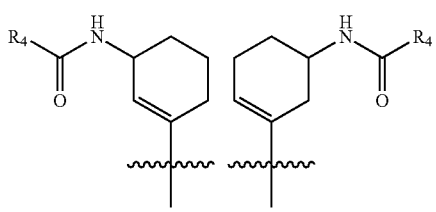

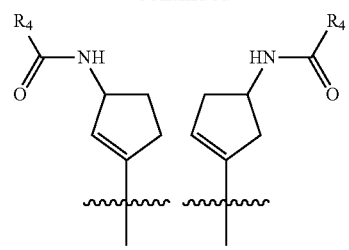

[10] The compound according to any one of [1] to [9], or a salt thereof, where $R_1$ represents a cyclopentenyl group; a cyclohexenyl group; a phenyl group; a furanyl group, which is optionally substituted with a group selected from the group consisting of a formyl group and a $C_1$-$C_6$ alkyl group (which is optionally substituted with a group selected from the group consisting of a hydroxy group and a di- or mono-($C_1$-$C_6$ alkyl)amino group); a 1H-pyrazolyl group, which is optionally substituted with a group selected from the group consisting of a $C_1$-$C_6$ alkyl group and a 4- to 10-membered saturated heterocyclic group; a thiazolyl group; an oxazolyl group; an isoxazolyl group; a 1,3,4-thiadiazolyl group; a 1,2,4-oxadiazolyl group; a 1,3,4-oxadiazolyl group, which is optionally substituted with a $C_1$-$C_6$ alkyl group; a pyridyl group, which is optionally substituted with a group selected from the group consisting of a halogen atom, an amino group, a hydroxy group, an N-oxide group, a $C_1$-$C_6$ alkyl group (which is optionally substituted with a hydroxy group), and a $C_1$-$C_6$ alkoxy group (which is optionally substituted with a halogen atom); a dihydropyranyl group; a dihydrofuranyl group; or a 4,5-dihydro-1,3,4-oxadiazolyl group, which is optionally substituted with a group selected from the group consisting of an oxo group and a $C_1$-$C_6$ alkyl group, $R_2$ represents a hydrogen atom; a cyano group; a ($C_1$-$C_6$ alkoxy)carbonyl group; a carbamoyl group; a di- or mono-($C_1$-$C_6$ alkyl)carbamoyl group; a $C_1$-$C_6$ alkyl group, which is optionally substituted with a group selected from the group consisting of a hydroxy group, a $C_1$-$C_6$ alkoxy group, a di- or mono-($C_1$-$C_6$ alkyl)amino group, and a 4- to 10-membered saturated heterocyclic group; a $C_1$-$C_6$ alkoxy group; or a monocyclic 5- or 6-membered completely unsaturated heterocyclic group having 1 to 3 N atoms, which is optionally substituted with a $C_1$-$C_6$ alkyl group, m represents 0, n represents 0 or 1, $R_4$ represents a $C_2$-$C_6$ alkenyl group, and in the formula (I), the following structure:

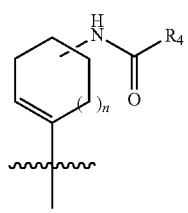

is any one of the following structures:

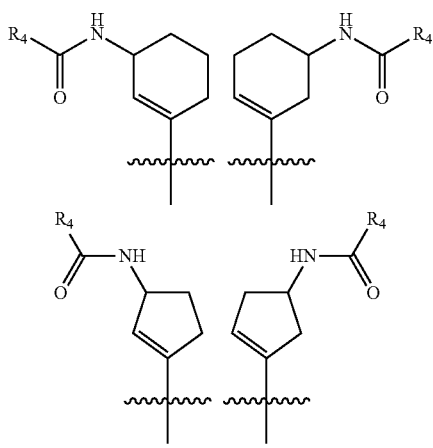

[11] The compound according to any one of [1] to [10], or a salt thereof, where the compound is any of compounds represented by the following (1) to (11):
(1) N-(3-(3-phenyl-1H-pyrrolo[2,3-b]pyridin-4-yl)cyclohex-3-en-1-yl)acrylamide,
(2) N-(3-(3-(1H-pyrazol-4-yl)-1H-pyrrolo[2,3-b]pyridin-4-yl)cyclohex-3-en-1-yl)acrylamide,
(3) N-(3-(3-(2-methoxypyridin-3-yl)-1H-pyrrolo[2,3-b]pyridin-4-yl)cyclohex-3-en-1-yl)acrylamide,
(4) N-(3-(3-(furan-2-yl)-1H-pyrrolo[2,3-b]pyridin-4-yl)cyclohex-3-en-1-yl)acrylamide,
(5) N-(3-(3-(4-(hydroxymethyl)furan-2-yl)-1H-pyrrolo[2,3-b]pyridin-4-yl)cyclohex-3-en-1-yl)acrylamide,
(6) N-(3-(3-(2,5-dihydrofuran-3-yl)-1H-pyrrolo[2,3-b]pyridin-4-yl)cyclohex-3-en-1-yl)acrylamide,
(7) N-(3-(3-(oxazol-5-yl)-1H-pyrrolo[2,3-b]pyridin-4-yl)cyclohex-3-en-1-yl)acrylamide,
(8) N-(3-(3-(1,3,4-oxadiazol-2-yl)-1H-pyrrolo[2,3-b]pyridin-4-yl)cyclohex-3-en-1-yl)acrylamide,
(9) (S)-N-(3-(3-(1,3,4-oxadiazol-2-yl)-1H-pyrrolo[2,3-b]pyridin-4-yl)cyclohex-3-en-1-yl)acrylamide,
(10) N-(3-(3-(1,3,4-oxadiazol-2-yl)-1H-pyrrolo[2,3-b]pyridin-4-yl)cyclopent-3-en-1-yl)acrylamide, and
(11) (S)-N-(3-(3-(isoxazol-5-yl)-1H-pyrrolo[2,3-b]pyridin-4-yl)cyclohex-3-en-1-yl)acrylamide.
[12] A JAK3 inhibitor containing, as an active ingredient, the compound according to any one of [1] to [11] or a salt thereof.
[13] A pharmaceutical composition containing the compound according to any one of [1] to [11] or a salt thereof.
[14] The pharmaceutical composition according to [13], where the pharmaceutical composition is a pharmaceutical composition for treating a disease involving JAK3.
[15] An agent for preventing and/or treating rheumatoid arthritis or multiple sclerosis, containing, as an active ingredient, the compound according to any one of [1] to [11] or a salt thereof.
[16] The compound according to any one of [1] to [11] or a salt thereof, for treating a disease involving JAK3.
[17] The compound according to any one of [1] to [11] or a salt thereof, for preventing and/or treating rheumatoid arthritis or multiple sclerosis.
[18] Use of the compound according to any one of [1] to [11] or a salt thereof for producing a medicament for treating a disease involving JAK3.
[19] Use of the compound according to any one of [1] to [11] or a salt thereof for producing a medicament for preventing and/or treating rheumatoid arthritis or multiple sclerosis.
[20] A method for preventing and/or treating a disease involving JAK3, containing administering the compound according to any one of [1] to [11] or a salt thereof.
[21] A method for preventing and/or treating rheumatoid arthritis or multiple sclerosis, containing administering the compound according to any one of [1] to [11] or a salt thereof.

Advantageous Effects of Invention

The present invention provides a novel azaindole derivative useful as a selective JAK3 inhibitor, which is of the above formula (I), or a salt thereof.

It has been revealed that the compound of the present invention or a salt thereof has an excellent selective JAK3-inhibitory activity and suppresses the growth of human PBMC based on JAK3 signals. In addition, the compound of the present invention has excellent oral absorbability, and thus, it is useful as a pharmaceutical agent for oral administration. Accordingly, the compound of the present invention or a salt thereof is capable of preventing and/or treating a disease involving JAK3 such as rheumatoid arthritis and multiple sclerosis, without having severe side effects caused by JAK1 and JAK2 (lipid rise, anemia, neutropenia, immunosuppression, etc.).

DESCRIPTION OF EMBODIMENTS

The compound of the present invention of the above formula (I) is a compound, which contains azaindole as a basic structure, has a cycloalkenyl group at 4-position, and further has a cyclic substituent at 3-position, and it is a novel compound, which is not described in any one of the aforementioned Citations.

In the description regarding substituents in the present description, "$C_x$-$C_y$" indicates a substituent in which the number of carbon atoms in the alkyl portion or alkoxy portion is X to Y. For example, "$C_1$-$C_6$ alkyl group" indicates an alkyl group having 1 to 6 carbon atoms, and "($C_1$-$C_6$ alkoxy)carbonyl group" indicates a carbonyl group to which an alkoxy group having 1 to 6 carbon atoms binds. In addition, "X- to Y-membered" indicates that the number of atoms constituting a ring (the number of ring members) is X to Y. For example, "4- to 10-membered saturated heterocyclic group" means a saturated heterocyclic group having 4 to 10 ring members.

In the present description, specific examples of the "halogen atom" include a fluorine atom, a chlorine atom, a bromine atom, and an iodine atom.

In the present description, the "alkyl group" is a linear or branched saturated hydrocarbon group, and specific examples of the alkyl group include a methyl group, an ethyl group, an n-propyl group, an isopropyl group, an n-butyl group, an isobutyl group, a sec-butyl group, a tert-butyl group, an n-pentyl group, and an n-hexyl group.

In the present description, the "alkenyl group" is a linear or branched unsaturated hydrocarbon group containing at least one carbon-carbon double bond, and specific examples of the alkenyl group include a vinyl group, an allyl group, a 1-propenyl group, a 1-methylvinyl group, a 1-butenyl group, a 2-butenyl group, and a 3-butenyl group.

In the present description, the "alkynyl group" is a linear or branched unsaturated hydrocarbon group containing at least one carbon-carbon triple bond, and specific examples of the alkynyl group include an ethynyl group, a 1-propynyl group, a 2-propynyl group, a 1-butynyl group, a 2-butynyl group, and a 3-butynyl group.

In the present description, the "haloalkyl group" is a group in which one to all hydrogen atoms of the above described alkyl group are substituted with halogen atoms, and specific examples of the haloalkyl group include a monofluoromethyl group, a difluoromethyl group, a trifluoromethyl group, a 1-fluoroethyl group, a 2-fluoroethyl group, a 1,1-difluoroethyl group, a 1,2-difluoroethyl group, and a 2,2-difluoroethyl group.

In the present description, the "alkoxy group" is an oxy group to which the above described alkyl group binds, and specific examples of the alkoxy group include a methoxy group, an ethoxy group, an n-propoxy group, an isopropoxy group, an n-butoxy group, an isobutoxy group, and a tert-butoxy group.

In the present description, the "cycloalkyl group" is a monocyclic or polycyclic saturated hydrocarbon group, and specific examples of the cycloalkyl group include a cyclopropyl group, a cyclobutyl group, a cyclopentyl group, a cyclohexyl group, a cycloheptyl group, a decalyl group, and an adamantyl group.

In the present description, the "cycloalkenyl group" is a monocyclic or polycyclic unsaturated hydrocarbon group containing at least one carbon-carbon double bond, and specific examples of the cycloalkenyl group include a cyclobutenyl group, a cyclopentenyl group, a cyclohexenyl group, and a cycloheptenyl group.

In the present description, the "cycloalkynyl group" is a monocyclic or polycyclic unsaturated hydrocarbon group containing at least one carbon-carbon triple bond, and specific examples of the cycloalkynyl group include a cyclobutynyl group, cyclopentynyl group, a cyclohexynyl group, and a cycloheptynyl group.

In the present description, the "di- or mono-alkylamino group" is an amino group in which one or two hydrogen atoms are substituted with the above described alkyl groups, and specific examples of the di- or mono-alkylamino group include a methylamino group, a dimethylamino group, an ethylmethylamino group, and an isopropylamino group.

In the present description, the "alkylcarbonyl group" is a carbonyl group to which the above described alkyl group binds, and specific examples of the alkylcarbonyl group include an acetyl group and a propionyl group.

In the present description, the "alkoxycarbonyl group" is a carbonyl group to which the above described alkoxy group binds, and specific examples of the alkoxycarbonyl group include a methoxycarbonyl group and an ethoxycarbonyl group.

In the present description, "di- or mono-alkylcarbamoyl group" is a carbonyl group to which the above described di- or mono-alkylamino group binds, and specific examples of the di- or mono-alkylcarbamoyl group include a methylcarbamoyl group, a dimethylcarbamoyl group, an ethylmethylcarbamoyl group, and an isopropylcarbamoyl group.

In the present description, the "alkylcarbonylamino group" is an amino group in which one hydrogen atom is substituted with the above described alkylcarbonyl group, and specific examples of the alkylcarbonylamino group include an acetamide group and propionamide group.

In the present description, "alkoxycarbonylamino group" is an amino group in which one hydrogen atom is substituted with the above described alkoxycarbonyl group, and specific examples of the alkoxycarbonylamino group include a methoxycarbonylamino group and an ethoxycarbonylamino group.

In the present description, the "alkylcarbonyloxy group" is an oxy group to which the above described alkylcarbonyl group binds, and specific examples of the alkylcarbonyloxy group include an acetoxy group and a propionyloxy group.

In the present description, the "alkoxycarbonyloxy group" is an oxy group to which the above described alkoxycarbonyl group binds, and specific examples of the alkoxycarbonyloxy group include a methoxycarbonyloxy group and an ethoxycarbonyloxy group.

In the present description, the "di- or mono-alkylcarbamoyloxy group" is an oxy group to which the above described di- or mono-alkylcarbamoyl group binds, and specific examples of the di- or mono-alkylcarbamoyloxy group include a methylcarbamoyloxy group and a dimethylcarbamoyloxy group.

In the present description, the "alkylthio group" is a mercapto group in which a hydrogen atom is substituted with the above described alkyl group, and specific examples of the alkylthio group include a methylthio group and an ethylthio group.

In the present description, the "alkylsulfonyl group" is a sulfonyl group to which the above described alkyl group binds, and specific examples of the alkylsulfonyl group include a methylsulfonyl group and an ethylsulfonyl group.

In the present description, the "alkoxysulfonyl group" is a sulfonyl group to which the above described alkoxy group binds, and specific examples of the alkoxysulfonyl group include a methoxysulfonyl group and an ethoxysulfonyl group.

In the present description, the "alkylsulfonamide group" is an amino group in which one hydrogen atom is substituted with the above described alkylsulfonyl group, and specific examples of the alkylsulfonamide group include a methylsulfonamide group and an ethylsulfonamide group.

In the present description, the "di- or mono-alkylsulfamoyl group" is a sulfonyl group to which the above described di- or mono-alkylamino group binds, and specific examples of the di- or mono-alkylsulfamoyl group include an N-methylsulfamoyl group and an N,N-dimethylsulfamoyl group.

In the present description, the "di- or mono-alkylsulfamoylamino group" is an amino group in which one hydrogen atom is substituted with the above described di- or mono-alkylsulfamoyl group, and specific examples of the di- or mono-alkylsulfamoylamino group include an N-methylsulfamoylamino group and an N,N-dimethylsulfamoylamino group.

In the present description, the "aromatic hydrocarbon group" is a monocyclic or polycyclic aromatic hydrocarbon group, and it may be a group in which only some rings exhibit aromaticity. Specific examples include a phenyl group, a naphthyl group, and a tetrahydronaphthyl group.

In the present description, the "saturated heterocyclic group" is a monocyclic or polycyclic saturated heterocyclic group having a heteroatom selected from the group consisting of N, S and O, and specific examples of the saturated heterocyclic group include a pyrrolidinyl group, a piperidinyl group, a piperazinyl group, a hexamethyleneimino group, a morpholino group, a thiomorpholino group, a homopiperazinyl group, an oxetanyl group, a tetrahydrofuranyl group, and a tetrahydropyranyl group.

In the present description, the "unsaturated heterocyclic group" is a monocyclic or polycyclic, completely unsaturated heterocyclic group having a heteroatom selected from the group consisting of N, S and O (hereinafter also referred to as a "completely unsaturated heterocyclic group"), or a partially unsaturated heterocyclic group (hereinafter also referred to as a "partially unsaturated heterocyclic group"). Specific examples of the completely unsaturated heterocyclic group include an imidazolyl group, a thienyl group, a furanyl group, a pyrrolyl group, an oxazolyl group, an isoxazolyl group, a thiazolyl group, an isothiazolyl group, a thiadiazolyl group, an oxadiazolyl group, a pyrazolyl group, a triazolyl group, a tetrazolyl group, a pyridyl group, a pyrazyl group, a pyrimidinyl group, a pyridazinyl group, an indolyl group, an isoindolyl group, an indazolyl group, a triazolopyridyl group, a benzimidazolyl group, a benzoxazolyl group, a benzothiazolyl group, a benzothienyl group, a benzofuranyl group, a purinyl group, a quinolyl group, an isoquinolyl group, a quinazolinyl group, and a quinoxalyl group. Specific examples of the partially unsaturated heterocyclic group include a dihydropyranyl group, a dihydrofuranyl group, a dihydrooxadiazolyl group, a methylenedioxyphenyl group, an ethylenedioxyphenyl group, and a dihydrobenzofuranyl group.

In the present description, $R_a$ represents a halogen atom, a hydroxy group, a cyano group, a nitro group, an oxo group, an N-oxide group, $-C(=O)R_x$, $-C(=O)OR_x$, $-C(=O)N(R_x)(R_y)$, $-C(=O)SR_x$, $-C(=S)OR_x$, $-C(=O)ON(R_x)(R_y)$, $-N(R_x)(R_y)$, $-NR_xC(=O)R_y$, $-NR_xS(=O)_2R_y$, $-NR_xC(=O)OR_y$, $-NR_xC(=O)N(R_y)(R_z)$, $-NR_xS(=O)_2N(R_y)(R_z)$, $-N(R_x)-OR_y$, $=NR_x$, $=N-OR_x$, $-OC(=O)R_x$, $-OC(=S)R_x$, $-OC(=O)OR_x$, $-OC(=O)N(R_x)(R_y)$, $-OC(=S)OR_x$, $-SR_x$, $-S(=O)_2R_x$, $-S(=O)_2OR_x$, $-S(=O)_2N(R_x)(R_y)$, an optionally $R_b$-substituted $C_1$-$C_6$ alkyl group, an optionally $R_b$-substituted $C_2$-$C_6$ alkenyl group, an optionally $R_b$-substituted $C_2$-$C_6$ alkynyl group, an optionally $R_b$-substituted $C_1$-$C_6$ alkoxy group, an optionally $R_c$-substituted $C_3$-$C_{10}$ cycloalkyl group, an optionally $R_c$-substituted $C_6$-$C_{14}$ aromatic hydrocarbon group, or an optionally $R_c$-substituted 4- to 10-membered saturated or unsaturated heterocyclic group.

When the group represented by $R_a$ is substituted with $R_b$ or $R_c$, the substituents $R_b$ and $R_c$ may be identical to or different from one another, and the number of the substituents is not particularly limited. The number of the $R_b$ or $R_c$ is preferably from 1 to 5, more preferably from 1 to 3, and particularly preferably from 1 or 2.

In the present description, $R_b$ represents a halogen atom, an amino group, a hydroxy group, a cyano group, a nitro group, a $C_1$-$C_6$ alkoxy group, a di- or mono-($C_1$-$C_6$ alkyl)amino group, or a 4- to 10-membered saturated or unsaturated heterocyclic group.

In the present description, $R_c$ represents a halogen atom, an amino group, a hydroxy group, a cyano group, a nitro group, an oxo group, an imino group, an N-oxide group, a $C_1$-$C_6$ alkyl group, a $C_2$-$C_6$ alkenyl group, a $C_2$-$C_6$ alkynyl group, a $C_1$-$C_6$ alkoxy group, or a di- or mono-($C_1$-$C_6$ alkyl)amino group.

In the present description, $R_x$, $R_y$ and $R_z$, which are the same or different, each represent a hydrogen atom, a $C_1$-$C_6$ alkyl group, a $C_1$-$C_6$ haloalkyl group, a $C_2$-$C_6$ alkenyl group, a $C_2$-$C_6$ alkynyl group, a $C_3$-$C_{10}$ cycloalkyl group, a $C_6$-$C_{14}$ aromatic hydrocarbon group, or a 4- to 10-membered saturated or unsaturated heterocyclic group.

In the compound of the present invention of formula (I), $R_1$ represents an optionally substituted $C_4$-$C_{10}$ cycloalkyl group, an optionally substituted $C_4$-$C_{10}$ cycloalkenyl group, an optionally substituted $C_4$-$C_{10}$ cycloalkynyl group, an optionally substituted $C_6$-$C_{14}$ aromatic hydrocarbon group, or an optionally substituted 4- to 10-membered saturated or unsaturated heterocyclic group.

A group with which the $C_4$-$C_{10}$ cycloalkyl group, $C_4$-$C_{10}$ cycloalkenyl group, $C_4$-$C_{10}$ cycloalkynyl group, $C_6$-$C_{14}$ aromatic hydrocarbon group or 4- to 10-membered saturated or unsaturated heterocyclic group, which is represented by $R_1$, is optionally substituted is preferably $R_a$, and examples of the $R_a$ include a halogen atom, a hydroxy group, a cyano group, a nitro group, an oxo group, an N-oxide group, $-C(=O)R_x$, $-C(=O)OR_x$, $-C(=O)N(R_x)(R_y)$, $-C(=O)SR_x$, $-C(=S)OR_x$, $-C(=O)ON(R_x)(R_y)$, $-N(R_x)(R_y)$, $-NR_xC(=O)R_y$, $-NR_xS(=O)_2R_y$, $-NR_xC(=O)OR_y$, $-NR_xC(=O)N(R_y)(R_z)$, $-NR_xS(=O)_2N(R_y)(R_z)$, $-N(R_x)-OR_y$, $=NR_x$, $=N-OR_x$, $-OC(=O)R_x$, $-OC(=S)R_x$, $-OC(=O)OR_x$, $-OC(=O)N(R_x)(R_y)$, $-OC(=S)OR_x$, $-SR_x$, $-S(=O)_2R_x$, $-S(=O)_2OR_x$, $-S(=O)_2N(R_x)(R_y)$, an optionally $R_b$-substituted $C_1$-$C_6$ alkyl group, an optionally $R_b$-substituted $C_2$-$C_6$ alkenyl group, an optionally $R_b$-substituted $C_2$-$C_6$ alkynyl group, an optionally $R_b$-Substituted $C_1$-$C_6$ alkoxy group, an optionally $R_c$-substituted $C_3$-$C_{10}$ cycloalkyl group, an optionally $R_c$-substituted $C_6$-$C_{14}$ aromatic hydrocarbon group, and an optionally $R_c$-substituted 4- to 10-membered saturated or unsaturated heterocyclic group.

In the "optionally substituted $C_4$-$C_{10}$ cycloalkyl group" represented by $R_1$, the "$C_4$-$C_{10}$ cycloalkyl group" is preferably a $C_4$-$C_7$ cycloalkyl group, more preferably a $C_5$-$C_7$ cycloalkyl group, even more preferably a cyclopentyl group or a cyclohexyl group, and particularly preferably a cyclohexyl group.

In the "optionally substituted $C_4$-$C_{10}$ cycloalkyl group" represented by $R_1$, the substituent is preferably $R_a$, more preferably a halogen atom or an optionally $R_b$-substituted $C_1$-$C_6$ alkyl group, and particularly preferably a halogen atom or a $C_1$-$C_6$ alkyl group. The number of the substituents is not particularly limited, and it is preferably 0, namely, not-substituted, or 1 to 3, and particularly preferably not-substituted.

In the "optionally substituted $C_4$-$C_{10}$ cycloalkenyl group" represented by $R_1$, the "$C_4$-$C_{10}$ cycloalkenyl group" is preferably a $C_4$-$C_7$ cycloalkenyl group, more preferably a $C_5$-$C_7$ cycloalkenyl group, even more preferably a cyclopentenyl group or a cyclohexenyl group, and particularly preferably a cyclohexenyl group.

In the "optionally substituted $C_4$-$C_{10}$ cycloalkenyl group" represented by $R_1$, the substituent is preferably $R_a$, more preferably a halogen atom, a hydroxy group, an oxo group, or an optionally $R_b$-substituted $C_1$-$C_6$ alkyl group, more preferably a halogen atom, a hydroxy group, an oxo group, or a $C_1$-$C_6$ alkyl group, and particularly preferably a hydroxy group or an oxo group. The number of the substituents is not particularly limited, and it is preferably 0, namely, not-substituted, or 1 to 3, and particularly preferably not-substituted or 1.

In the "optionally substituted $C_4$-$C_{10}$ cycloalkynyl group" represented by $R_1$, the "$C_4$-$C_{10}$ cycloalkynyl group" is preferably a $C_4$-$C_7$ cycloalkynyl group, more preferably a $C_5$-$C_7$ cycloalkynyl group, even more preferably a cyclopentynyl group or a cyclohexynyl group, and particularly preferably a cyclohexynyl group.

In the "optionally substituted $C_4$-$C_{10}$ cycloalkynyl group" represented by $R_1$, the substituent is preferably $R_a$, more preferably a halogen atom or an optionally $R_b$-substituted $C_1$-$C_6$ alkyl group, and particularly preferably a halogen atom or a $C_1$-$C_6$ alkyl group. The number of the substituents is not particularly limited, and it is preferably 0, namely, not-substituted, or 1 to 3, and particularly preferably not-substituted.

In the "optionally substituted $C_6$-$C_{14}$ aromatic hydrocarbon group" represented by $R_1$, the "$C_6$-$C_{14}$ aromatic hydrocarbon group" is preferably a $C_6$-$C_{10}$ aromatic hydrocarbon group, more preferably a phenyl group or a naphthyl group, and particularly preferably a phenyl group.

In the "optionally substituted $C_6$-$C_{14}$ aromatic hydrocarbon group" represented by $R_1$, the substituent is preferably $R_a$, more preferably a halogen atom or an optionally $R_b$-substituted $C_1$-$C_6$ alkyl group, and particularly preferably a halogen atom or a $C_1$-$C_6$ alkyl group. The number of the substituents is not particularly limited, and it is preferably 0, namely, not-substituted, or 1 to 3, and particularly preferably not-substituted.

In the "optionally substituted 4- to 10-membered saturated heterocyclic group" represented by $R_1$, the "4- to 10-membered saturated heterocyclic group" is preferably a monocyclic or polycyclic 4- to 10-membered saturated heterocyclic group having 1 to 3 heteroatoms selected from the group consisting of N, S and O, more preferably a monocyclic 4- to 7-membered saturated heterocyclic group having 1 to 3 heteroatoms selected from the group consisting of N, S and O, and even more preferably a pyrrolidinyl group, a piperidinyl group, a piperazinyl group, a hexamethyleneimino group, a morpholino group, a thiomorpholino group, a homopiperazinyl group, an oxetanyl group, a tetrahydrofuranyl group, or a tetrahydropyranyl group.

In the "optionally substituted 4- to 10-membered saturated heterocyclic group" represented by $R_1$, the substituent is preferably $R_a$, more preferably a halogen atom or an optionally $R_b$-substituted $C_1$-$C_6$ alkyl group, and particularly preferably a halogen atom or a $C_1$-$C_6$ alkyl group. The number of the substituents is not particularly limited, and it is preferably 0, namely, not-substituted, or 1 to 3, and particularly preferably not-substituted.

In the "optionally substituted 4- to 10-membered unsaturated heterocyclic group" represented by $R_1$, the "4- to 10-membered unsaturated heterocyclic group" is preferably a monocyclic or polycyclic 4- to 10-membered unsaturated heterocyclic group having 1 to 3 heteroatoms selected from the group consisting of N, S and O, more preferably a monocyclic 4- to 7-membered unsaturated heterocyclic group having 1 to 3 heteroatoms selected from the group consisting of N, S and O, even more preferably an imidazolyl group, a thienyl group, a furanyl group, a pyrrolyl group, an oxazolyl group, an isoxazolyl group, a thiazolyl group, an isothiazolyl group, a thiadiazolyl group, an oxadiazolyl group, a pyrazolyl group, a triazolyl group, a pyridyl group, a pyrazyl group, a pyrimidinyl group, a pyridazinyl group, a dihydropyranyl group, a dihydrofuranyl group, or a dihydrooxadiazolyl group, further preferably a furanyl group, a 1H-pyrazolyl group, a 4H-pyrazolyl group, a thiazolyl group, an oxazolyl group, an isoxazolyl group, a 1,2,3-thiadiazolyl group, a 1,2,4-thiadiazolyl group, a 1,3,4-thiadiazolyl group, a 1,2,3-oxadiazolyl group, a 1,2,4-oxadiazolyl group, a 1,3,4-oxadiazolyl group, a pyridyl group, a 3,4-dihydro-2H-pyranyl group, a 3,6-dihydro-2H-pyranyl group, a 2,3-dihydrofuranyl group, a 2,5-dihydrofuranyl group, a 2,5-dihydro-1,3,4-oxadiazolyl group, or a 4,5-dihydro-1,3,4-oxadiazolyl group, still further preferably a furanyl group, a 1H-pyrazolyl group, a thiazolyl group, an oxazolyl group, an isoxazolyl group, a 1,3,4-thiadiazolyl group, a 1,2,4-oxadiazolyl group, a 1,3,4-oxadiazolyl group, a pyridyl group, a 3,6-dihydro-2H-pyranyl group, a 2,5-dihydrofuranyl group, or a 4,5-dihydro-1,3,4-oxadiazolyl group, still further preferably a furanyl group, a 1H-pyrazolyl group, a thiazolyl group, an oxazolyl group, a 1,3,4-thiadiazolyl group, a 1,3,4-oxadiazolyl group, a pyridyl group, a 3,6-dihydro-2H-pyranyl group, a 2,5-dihydrofuranyl group, or a 4,5-dihydro-1,3,4-oxadiazolyl group, and particularly preferably a furanyl group, a 1H-pyrazolyl group, an oxazolyl group, a 1,3,4-thiadiazolyl group, a 1,3,4-oxadiazolyl group, a pyridyl group, a 2,5-dihydrofuranyl group, or a 4,5-dihydro-1,3,4-oxadiazolyl group.

In the "optionally substituted 4- to 10-membered unsaturated heterocyclic group" represented by $R_1$, the substituent is preferably $R_a$, more preferably a halogen atom, an amino group, a hydroxy group, an oxo group, an N-oxide group, —C(=O)$R_x$, an optionally $R_b$-substituted $C_1$-$C_6$ alkyl group, an optionally $R_b$-substituted $C_1$-$C_6$ alkoxy group, or an optionally $R_c$-substituted 4- to 10-membered saturated heterocyclic group, even more preferably a halogen atom; an amino group; an oxo group; an N-oxide group; a formyl group; a $C_1$-$C_6$ alkyl group optionally substituted with a group selected from the group consisting of a hydroxy group and a di- or mono-($C_1$-$C_6$ alkyl)amino group; a $C_1$-$C_6$ alkoxy group optionally substituted with a halogen atom; or a 4- to 10-membered saturated heterocyclic group, and particularly preferably a halogen atom; an oxo group; a $C_1$-$C_6$ alkyl group optionally substituted with a hydroxy group; or a $C_1$-$C_6$ alkoxy group. The number of the substituents is not particularly limited, and it is preferably 0, namely, not-substituted, or 1 to 3, and particularly preferably not-substituted, or 1 or 2.

The $R_1$ in the present invention is preferably an optionally substituted $C_4$-$C_{10}$ cycloalkenyl group, an optionally substituted $C_6$-$C_{14}$ aromatic hydrocarbon group, or an optionally substituted monocyclic or polycyclic 4- to 10-membered unsaturated heterocyclic group having 1 to 3 heteroatoms selected from the group consisting of N, S and O, more preferably, an optionally $R_a$-substituted $C_4$-$C_{10}$ cycloalkenyl group, an optionally $R_a$-substituted $C_6$-$C_{14}$ aromatic hydrocarbon group, or an optionally $R_a$-substituted monocyclic or polycyclic 4- to 10-membered unsaturated heterocyclic group having 1 to 3 heteroatoms selected from the group consisting of N, S and O, even more preferably, an optionally $R_a$-substituted $C_5$-$C_7$ cycloalkenyl group, an optionally $R_a$-substituted $C_6$-$C_{10}$ aromatic hydrocarbon group, or an optionally $R_a$-substituted monocyclic 4- to 7-membered unsaturated heterocyclic group having 1 to 3 heteroatoms selected from the group consisting of N, S and O, further preferably, a cyclopentenyl group, a cyclohexenyl group, a phenyl group, a furanyl group, a 1H-pyrazolyl group, a thiazolyl group, an oxazolyl group, an isoxazolyl group, a 1,3,4-thiadiazolyl group, a 1,2,4-oxadiazolyl group, a 1,3,4-oxadiazolyl group, a pyridyl group, a dihydropyranyl group, a dihydrofuranyl group, or a 4,5-dihydro-1,3,4-oxadiazolyl group (where the cycloalkenyl group, aromatic hydrocarbon group, and unsaturated heterocyclic group are optionally substituted with $R_a$), further preferably, a cyclopentenyl group, a cyclohexenyl group, a phenyl group, a furanyl group, a 1H-pyrazolyl group, a thiazolyl group, an oxazolyl group, an isoxazolyl group, a 1,3,4-thiadiazolyl group, a 1,2,4-oxadiazolyl group, a 1,3,4-oxadiazolyl group, a pyridyl group, a dihydropyranyl group, a dihydrofuranyl group, or a 4,5-dihydro-1,3,4-oxadiazolyl group (where the cycloalkenyl group, aromatic hydrocarbon group, and unsaturated heterocyclic group are optionally substituted with a group selected from the group consisting of a halogen atom, an amino group, a hydroxy group, an oxo group, an N-oxide group, a formyl group, a $C_1$-$C_6$ alkyl group (which is optionally substituted with a group selected from the group consisting of a hydroxy group and a di- or mono-($C_1$-$C_6$ alkyl)amino group), a $C_1$-$C_6$ alkoxy group (which is optionally substituted with a halogen atom), and 4- to 10-membered saturated heterocyclic group), still further preferably, a cyclopentenyl group; a cyclohexenyl group; a phenyl group; and a furanyl group optionally substituted with a group selected from the group consisting of a formyl group and a $C_1$-$C_6$ alkyl group (which is optionally substituted with a hydroxy group and a di- or mono-($C_1$-$C_6$ alkyl)amino group); a 1H-pyrazolyl group optionally substituted with a group selected from the group consisting of a $C_1$-$C_6$ alkyl group and a 4- to 10-membered saturated heterocyclic group; a thiazolyl group; an oxazolyl group; an isoxazolyl group; a 1,3,4-thiadiazolyl group; a 1,2,4-oxadiazolyl group; a 1,3,4-oxadiazolyl group optionally substituted with a $C_1$-$C_6$ alkyl group; a pyridyl group optionally substituted with a group selected from the group consisting of a halogen atom, an amino group, a hydroxy group, an N-oxide group, a $C_1$-$C_6$ alkyl group (which is optionally substituted with a hydroxy group), and a $C_1$-$C_6$ alkoxy group (which is optionally substituted with a halogen atom); a dihydropyranyl group; a dihydrofuranyl group; and a 4,5-dihydro-1,3,4-oxadiazolyl group optionally substituted with a group selected from the group consisting of an oxo group and a $C_1$-$C_6$ alkyl group, and particularly preferably, a phenyl group; a furanyl group optionally substituted with a $C_1$-$C_6$ alkyl group (which is optionally substituted with a hydroxy group); a 1H-pyrazolyl group; an oxazolyl group; a 1,3,4-thiadiazolyl group; a 1,3,4-oxadiazolyl group; a pyridyl group optionally substituted with a group selected from the group consisting of a halogen atom and a $C_1$-$C_6$ alkoxy group; a dihydrofuranyl group; and a 4,5-dihydro-1,3,4-oxadiazolyl group optionally substituted with a group selected from the group consisting of an oxo group and a $C_1$-$C_6$ alkyl group.

In the compound of the present invention of formula (I), $R_2$ represents a hydrogen atom, a halogen atom, a hydroxy group, a cyano group, a nitro group, —C(=O)$R_x$, —C(=O)O$R_x$, —C(=O)N($R_x$)($R_y$), —N($R_x$)($R_y$), —NR$_x$C(=O)$R_y$, —NR$_x$S(=O)$_2$$R_y$, —NR$_x$C(=O)O$R_y$, —NR$_x$C(=O)N($R_y$)($R_z$), —NR$_x$S(=O)$_2$N($R_y$)($R_z$), —OC(=O)$R_x$, —OC(=O)O$R_x$, —OC(=O)N($R_x$)($R_y$), —S$R_x$, —S(=O)$_2$$R_x$, —S(=O)$_2$O$R_x$, an optionally $R_b$-Substituted $C_1$-$C_6$ alkyl group, an optionally $R_b$-Substituted $C_2$-$C_6$ alkenyl group, an optionally $R_b$-substituted $C_2$-$C_6$ alkynyl group, an optionally $R_b$-substituted $C_1$-$C_6$ alkoxy group, an optionally $R_c$-substituted $C_3$-$C_{10}$ cycloalkyl group, an optionally $R_c$-substituted $C_6$-$C_{14}$ aromatic hydrocarbon group, or an optionally $R_c$-substituted 4- to 10-membered saturated or unsaturated heterocyclic group.

The "—C(=O)$R_x$" represented by $R_2$ is preferably a formyl group or a ($C_1$-$C_6$ alkyl)carbonyl group, more preferably a formyl group, an acetyl group, or a propionyl group, and particularly preferably a formyl group.

The "—C(=O)O$R_x$" represented by $R_2$ is preferably a carboxy group or a ($C_1$-$C_6$ alkoxy)carbonyl group, more preferably a methoxycarbonyl group or an ethoxycarbonyl group, and particularly preferably a methoxycarbonyl group.

The "—C(=O)N($R_x$)($R_y$)" represented by $R_2$ is preferably a carbamoyl group (—C(=O)NH$_2$) or a di- or mono-($C_1$-$C_6$ alkyl)carbamoyl group, and particularly preferably a carbamoyl group, a methylcarbamoyl group, or a dimethylcarbamoyl group.

The "—N($R_x$)($R_y$)" represented by $R_2$ is preferably an amino group or a di- or mono-($C_1$-$C_6$ alkyl)amino group, more preferably an amino group, a methylamino group, or a dimethylamino group, and particularly preferably an amino group.

The "—NR$_x$C(=O)$R_y$" represented by $R_2$ is preferably a formamide group or a ($C_1$-$C_6$ alkyl)carbonylamino group, more preferably a formamide group, an acetamide group, or a propionamide group, and particularly preferably a formamide group.

The "—NR$_x$S(=O)$_2$$R_y$" represented by $R_2$ is preferably a hydrosulfonylamino group (—NH—S(=O)$_2$H) or a ($C_1$—C(alkyl)sulfonamide group, more preferably a hydrosulfonylamino group, a methylsulfonamide group, or an ethylsulfonamide group, and particularly preferably a hydrosulfonylamino group.

The "—NR$_x$C(=O)O$R_y$" represented by $R_2$ is preferably a carboxyamino group (—NH—C(=O)OH) or a ($C_1$-$C_6$ alkoxy)carbonylamino group, more preferably a carboxyamino group, a methoxycarbonylamino group, or an ethylcarbonylamino group, and particularly preferably a carboxyamino group.

The "—NR$_x$C(=O)N($R_y$)($R_z$)" represented by $R_2$ is preferably a ureido group (—NH—C(=O)NH$_2$) or a di- or mono-($C_1$-$C_6$ alkyl)ureido group, more preferably a ureido group, a 3-methylureido group, or a 3,3-dimethylureido group, and particularly preferably a ureido group.

The "—NR$_x$S(=O)$_2$N($R_y$)($R_z$)" represented by $R_2$ is preferably a sulfamoylamino group (—NH—S(=O)$_2$NH$_2$) or a di- or mono-($C_1$-$C_6$ alkyl)sulfamoylamino group, more preferably a sulfamoylamino group, an N-methylsulfamoylamino group, or an N,N-dimethylsulfamoylamino group, and particularly preferably a sulfamoylamino group.

The "—OC(=O)$R_x$" represented by $R_2$ is preferably a formyloxy group, or a ($C_1$-$C_6$ alkyl)carbonyloxy group, more preferably a formyloxy group, an acetoxy group, or a propionyloxy group, and particularly preferably a formyloxy group.

The "—OC(=O)O$R_x$" represented by $R_2$ is preferably a carboxyoxy group or a ($C_1$-$C_6$ alkoxy)carbonyloxy group, more preferably a carboxyoxy group, a methoxycarbonyloxy group, or an ethoxycarbonyloxy group, and particularly preferably a carboxyoxy group.

The "—OC(=O)N($R_x$)($R_y$)" represented by $R_2$ is preferably a carbamoyloxy group (—OC(=O)NH$_2$) or a di- or mono-($C_1$-$C_6$ alkyl)carbamoyloxy group, more preferably a carbamoyloxy group, a methylcarbamoyloxy group, or a dimethylcarbamoyloxy group, and particularly preferably a carbamoyloxy group.

The "—S$R_x$" represented by $R_2$ is preferably a mercapto group or a ($C_1$-$C_6$ alkyl)thio group, more preferably a mercapto group, a methylthio group, or an ethylthio group, and particularly preferably a mercapto group.

The "—S(=O)$_2$$R_x$" represented by $R_2$ is preferably a ($C_1$-$C_6$ alkyl)sulfonyl group, more preferably a methylsulfonyl group or an ethylsulfonyl group, and particularly preferably a methylsulfonyl group.

The "—S(=O)$_2$O$R_x$" represented by $R_2$ is preferably a sulfo group (—S(=O)$_2$OH) or a ($C_1$-$C_6$ alkoxy)sulfonyl group, more preferably a sulfo group, a methoxysulfonyl group, or an ethoxysulfonyl group, and particularly preferably a sulfo group.

In the "optionally $R_b$-substituted $C_1$-$C_6$ alkyl group" represented by $R_2$, the "$C_1$-$C_6$ alkyl group" is preferably a $C_1$-$C_4$ alkyl group, more preferably a methyl group or an ethyl group, and particularly preferably a methyl group.

In the "optionally $R_b$-substituted $C_1$-$C_6$ alkyl group" represented by $R_2$, the $R_b$ is preferably a hydroxy group, a $C_1$-$C_6$ alkoxy group, a di- or mono-($C_1$-$C_6$ alkyl)amino group, or a 4- to 10-membered saturated heterocyclic group, more preferably a hydroxy group, a $C_1$-$C_6$ alkoxy group, a di- or mono-($C_1$-$C_6$ alkyl)amino group, or a monocyclic 5- or 6-membered saturated heterocyclic group having 1 to 3 heteroatoms selected from the group consisting of N and O, and particularly preferably a hydroxy group, a $C_1$-$C_6$ alkoxy group, a di- or mono-($C_1$-$C_6$ alkyl)amino group, or a morpholino group. The number of the $R_b$ is not particularly limited, and it is preferably 0, namely, not-substituted, or 1 to 3, and particularly preferably 1.

In the "optionally $R_b$-substituted $C_2$-$C_6$ alkenyl group" represented by $R_2$, the "$C_2$-$C_6$ alkenyl group" is preferably a $C_2$-$C_4$ alkenyl group, and particularly preferably a vinyl group.

In the "optionally $R_b$-substituted $C_2$-$C_6$ alkenyl group" represented by $R_2$, the $R_b$ is preferably a halogen atom. The number of the $R_b$ is not particularly limited, and it is preferably 0, namely, not-substituted, or 1 to 3, and particularly preferably not-substituted.

In the "optionally $R_b$-substituted $C_2$-$C_6$ alkynyl group" represented by $R_2$, the "$C_2$-$C_6$ alkynyl group" is preferably a $C_2$-$C_4$ alkynyl group, and particularly preferably an ethynyl group.

In the "optionally $R_b$-substituted $C_2$-$C_6$ alkynyl group" represented by $R_2$, the $R_b$ is preferably a halogen atom. The number of the $R_b$ is not particularly limited, and it is preferably 0, namely, not-substituted, or 1 to 3, and particularly preferably not-substituted.

In the "optionally $R_b$-substituted $C_1$-$C_6$ alkoxy group" represented by $R_2$, the "$C_1$-$C_6$ alkoxy group" is preferably a $C_1$-$C_4$ alkoxy group, more preferably a methoxy group or an ethoxy group, and particularly preferably a methoxy group.

In the "optionally $R_b$-substituted $C_1$-$C_6$ alkoxy group" represented by $R_2$, the $R_b$ is preferably a halogen atom. The number of the $R_b$ is not particularly limited, and it is preferably 0, namely, not-substituted, or 1 to 3, and particularly preferably not-substituted.

In the "optionally $R_c$-substituted $C_3$-$C_{10}$ cycloalkyl group" represented by $R_2$, the "$C_3$-$C_{10}$ cycloalkyl group" is preferably a $C_4$-$C_7$ cycloalkyl group, more preferably a $C_5$-$C_7$ cycloalkyl group, even more preferably a cyclopentyl group or a cyclohexyl group, and particularly preferably a cyclohexyl group.

In the "optionally $R_c$-substituted $C_3$-$C_{10}$ cycloalkyl group" represented by $R_2$, the $R_c$ is preferably a halogen atom. The number of the $R_c$ is not particularly limited, and it is preferably 0, namely, not-substituted, or 1 to 3, and particularly preferably not-substituted.

In the "optionally $R_c$-substituted $C_6$-$C_{14}$ aromatic hydrocarbon group" represented by $R_2$, the "$C_6$-$C_{14}$ aromatic hydrocarbon group" is preferably a $C_6$-$C_{10}$ aromatic hydrocarbon group, more preferably a phenyl group or a naphthyl group, and particularly preferably a phenyl group.

In the "optionally $R_c$-substituted $C_6$-$C_{14}$ aromatic hydrocarbon group" represented by $R_2$, the $R_c$ is preferably a halogen atom. The number of the $R_c$ is not particularly limited, and it is preferably 0, namely, not-substituted, or 1 to 3, and particularly preferably not-substituted.

In the "optionally $R_c$-substituted 4- to 10-membered saturated heterocyclic group" represented by $R_2$, the "4- to 10-membered saturated heterocyclic group" is preferably a monocyclic or polycyclic 4- to 10-membered saturated heterocyclic group having 1 to 3 heteroatoms selected from the group consisting of N, S and O, more preferably a monocyclic 4- to 7-membered saturated heterocyclic group having 1 to 3 heteroatoms selected from the group consisting of N and O, even more preferably a pyrrolidinyl group, a piperidinyl group, a piperazinyl group, a hexamethyleneimino group, a morpholino group, a homopiperazinyl group, an oxetanyl group, a tetrahydrofuranyl group, or a tetrahydropyranyl group, and particularly preferably a morpholino group.

In the "optionally $R_c$-substituted 4- to 10-membered saturated heterocyclic group" represented by $R_2$, the $R_c$ is preferably a halogen atom. The number of the $R_c$ is not particularly limited, and it is preferably 0, namely, not-substituted, or 1 to 3, and particularly preferably not-substituted.

In the "optionally $R_c$-substituted 4- to 10-membered unsaturated heterocyclic group" represented by $R_2$, the "4- to 10-membered unsaturated heterocyclic group" is preferably a monocyclic or polycyclic 4- to 10-membered unsaturated heterocyclic group having 1 to 3 heteroatoms selected from the group consisting of N, S and O, more preferably a monocyclic 4- to 7-membered unsaturated heterocyclic group having 1 to 3 heteroatoms selected from the group consisting of N, S and O, even more preferably a monocyclic 5- or 6-membered completely unsaturated heterocyclic group having 1 to 3 N atoms, further preferably an imidazolyl group, a pyrazolyl group, a triazolyl group, a pyridyl group, a pyrazyl group, a pyrimidinyl group, or a pyridazinyl group, still further preferably a pyrazolyl group, and particularly preferably a 1H-pyrazolyl group.

In the "optionally $R_c$-substituted 4- to 10-membered unsaturated heterocyclic group" represented by $R_2$, the $R_c$ is preferably a halogen atom or a $C_1$-$C_6$ alkyl group, and particularly preferably a $C_1$-$C_6$ alkyl group. The number of the $R_c$ is not particularly limited, and it is preferably 0, namely, not-substituted, or 1 to 3, and particularly preferably not-substituted or 1.

The $R_2$ in the present invention is preferably a hydrogen atom, a cyano group, —C(=O)OR$_x$, —C(=O)N(R$_x$)(R$_y$), an optionally $R_b$-substituted $C_1$-$C_6$ alkyl group, an optionally $R_b$-substituted $C_1$-$C_6$ alkoxy group, or an optionally $R_c$-substituted monocyclic 4- to 7-membered unsaturated heterocyclic group having 1 to 3 heteroatoms selected from the group consisting of N, S and O, more preferably, a hydrogen atom; a cyano group; a ($C_1$-$C_6$ alkoxy)carbonyl group; a carbamoyl group; a di- or mono-($C_1$-$C_6$ alkyl)carbamoyl group; a $C_1$-$C_6$ alkyl group optionally substituted with a group selected from the group consisting of a hydroxy group, a $C_1$-$C_6$ alkoxy group, a di- or mono-($C_1$-$C_6$ alkyl)amino group, and a 4- to 10-membered saturated heterocyclic group; a $C_1$-$C_6$ alkoxy group; or a monocyclic 5- or 6-membered completely unsaturated heterocyclic group having 1 to 3 N atoms, which is optionally substituted with a $C_1$-$C_6$ alkyl group, even more preferably, a hydrogen atom; a cyano group; a $C_1$-$C_6$ alkoxy group; or a pyrazolyl group optionally substituted with a $C_1$-$C_6$ alkyl group, and particularly preferably, a hydrogen atom.

In the compound of the present invention of formula (I), $R_3$ represents a halogen atom, an amino group, a hydroxy group, a cyano group, a nitro group, a $C_1$-$C_6$ alkyl group, a $C_2$-$C_6$ alkenyl group, a $C_2$-$C_6$ alkynyl group, or a $C_1$-$C_6$ alkoxy group.

The $R_3$ in the present invention is preferably a halogen atom or a $C_1$-$C_6$ alkyl group, and particularly preferably a halogen atom.

The number of the $R_3$ in the present invention, which is m, is preferably 0 to 2, more preferably 0 or 1, and particularly preferably 0, namely, not-substituted.

In the compound of the present invention of formula (I), $R_4$ represents an optionally $R_b$-substituted $C_2$-$C_6$ alkenyl group or an optionally $R_b$-substituted $C_2$-$C_6$ alkynyl group.

In the "optionally $R_b$-substituted $C_2$-$C_6$ alkenyl group" represented by $R_4$, the "$C_2$-$C_6$ alkenyl group" is preferably a $C_2$-$C_4$ alkenyl group, more preferably a vinyl group, an allyl group, a 1-propenyl group, a 1-methylvinyl group, a 1-butenyl group, a 2-butenyl group, or a 3-butenyl group, even more preferably a vinyl group or a 1-propenyl group, and particularly preferably a vinyl group.

In the "optionally $R_b$-substituted $C_2$-$C_6$ alkenyl group" represented by $R_4$, the $R_b$ is preferably a halogen atom, an amino group, a $C_1$-$C_6$ alkoxy group, or a di- or mono-($C_1$-$C_6$ alkyl)amino group, more preferably a halogen atom or a $C_1$-$C_6$ alkoxy group, and particularly preferably a halogen atom. The number of the $R_b$ is not particularly limited, and it is preferably 0, namely, not-substituted, or 1 to 3, and particularly preferably not-substituted.

The "optionally $R_b$-substituted $C_2$-$C_6$ alkynyl group" represented by $R_4$ is preferably a $C_2$-$C_4$ alkynyl group, more preferably an ethynyl group, a 1-propynyl group, or a 1-butynyl group, even more preferably an ethynyl group or a 1-propynyl group, and particularly preferably an ethynyl group.

In the "optionally $R_b$-substituted $C_2$-$C_6$ alkynyl group" represented by $R_4$, the $R_b$ is preferably a halogen atom, an amino group, a $C_1$-$C_6$ alkoxy group, or a di- or mono-($C_1$-$C_6$ alkyl)amino group, more preferably a halogen atom or a $C_1$-$C_6$ alkoxy group, and particularly preferably a halogen atom. The number of the $R_b$ is not particularly limited, and it is preferably 0, namely, not-substituted, or 1 to 3, and particularly preferably not-substituted.

The $R_4$ in the present invention is preferably a $C_2$-$C_6$ alkenyl group or a $C_2$-$C_6$ alkynyl group, more preferably a $C_2$-$C_4$ alkenyl group or a $C_2$-$C_4$ alkynyl group, even more preferably a vinyl group, a 1-propenyl group, an ethynyl group, or a 1-propynyl group, further preferably a vinyl group or an ethynyl group, and particularly preferably a vinyl group.

The n in the present invention is preferably 0 or 1, and particularly preferably 1.

In the compound of the present invention of formula (I), the following structure

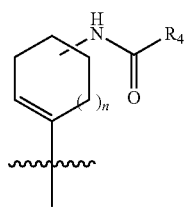

is preferably the following structures (1) to (7).

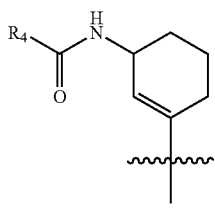
(1)

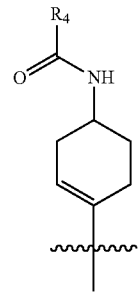
(2)

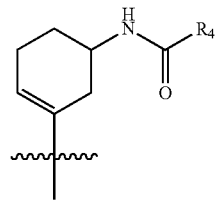
(3)

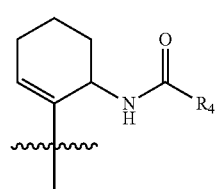
(4)

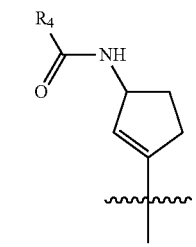
(5)

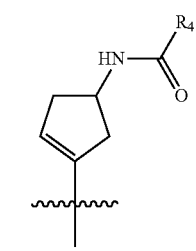
(6)

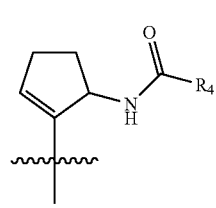
(7)

Among these structures, the structures (1), (3), (5) and (6) are more preferable, the structures (1) and (3) are even more preferable, and the structure (3) is particularly preferable.

A preferred compound of the present invention is a compound in which $R_1$ represents an optionally $R_a$-substituted $C_4$-$C_{10}$ cycloalkenyl group, an optionally $R_a$-substituted $C_6$-$C_{14}$ aromatic hydrocarbon group, or an optionally $R_a$-substituted monocyclic or polycyclic 4- to 10-membered unsaturated heterocyclic group having 1 to 3 heteroatoms selected from the group consisting of N, S and O, $R_2$ represents a hydrogen atom, a cyano group, —C(=O)OR$_x$, —C(=O)N(R$_x$)(R$_y$), an optionally R$_b$-substituted $C_1$-$C_6$ alkyl group, an optionally R$_b$-substituted $C_1$-$C_6$ alkoxy group, or an optionally R$_c$-substituted monocyclic 4- to 7-membered unsaturated heterocyclic group having 1 to 3 heteroatoms selected from the group consisting of N, S and O, m represents 0, n represents 0 or 1, $R_4$ represents a $C_2$-$C_6$ alkenyl group or a $C_2$-$C_6$ alkynyl group, $R_a$ represents a halogen atom, a hydroxy group, a cyano group, a nitro group, an oxo group, an N-oxide group, —C(=O)R$_x$, —C(=O)OR$_x$, —C(=O)N(R$_x$)(R$_y$), —C(=O)SR$_x$, —C(=S)OR$_x$, —C(=O)ON(R$_x$)(R$_y$), —N(R$_x$)(R$_y$), —NR$_x$C(=O)R$_y$, —NR$_x$S(=O)$_2$R$_y$, —NR$_x$C(=O)OR$_y$, —NR$_x$C(=O)N(R$_y$)(R$_z$), —NR$_x$S(=O)$_2$N(R$_y$)(R$_z$), —N(R$_x$)—OR$_y$, =NR$_x$, =N—OR$_x$, —OC(=O)R$_x$, —OC(=S)R$_x$, —OC(=O)OR$_x$, —OC(=O) N(R$_x$)(R$_y$), —OC(=S) OR$_x$, —SR$_x$, —S(=O)$_2$R$_x$, —S(=O)$_2$OR$_x$, —S(=O)$_2$N(R$_x$)(R$_y$), an optionally R$_b$-substituted $C_1$-$C_6$ alkyl group, an optionally R$_b$-Substituted $C_2$-$C_6$ alkenyl group, an optionally R$_b$-substituted $C_2$-$C_6$ alkynyl group, an optionally R$_b$-substituted $C_1$-$C_6$ alkoxy group, an optionally R$_c$-substituted $C_3$-$C_{10}$ cycloalkyl group, an optionally R$_c$-substituted $C_6$-$C_{14}$ aromatic hydrocarbon group, or an optionally R$_c$-substituted 4- to 10-membered saturated or unsaturated heterocyclic group, $R_b$ represents a halogen atom, an amino group, a hydroxy group, a cyano group, a nitro group, a $C_1$-$C_6$ alkoxy group, a di- or mono-($C_1$-$C_6$ alkyl)amino group, or a 4- to 10-membered saturated or unsaturated heterocyclic group, $R_c$ represents a halogen atom, an amino group, a hydroxy group, a cyano group, a nitro group, an oxo group, an imino group, an N-oxide group, a $C_1$-$C_6$ alkyl group, a $C_2$-$C_6$ alkenyl group, a $C_2$-$C_6$ alkynyl group, a $C_1$-$C_6$ alkoxy group or a di- or mono-($C_1$-$C_6$ alkyl)amino group, and $R_x$, $R_y$ and $R_z$, which are the same or different, each represent a hydrogen atom, a $C_1$-$C_6$ alkyl group, a $C_1$-$C_6$ haloalkyl group, a $C_2$-$C_6$ alkenyl group, a $C_2$-$C_6$ alkynyl group, a $C_3$-$C_{10}$ cycloalkyl group, a $C_6$-$C_{14}$ aromatic hydrocarbon group, or a 4- to 10-membered saturated or unsaturated heterocyclic group.

The compound of the present invention is more preferably a compound in which $R_1$ represents an optionally R$_a$-substituted $C_5$-$C_7$ cycloalkenyl group, an optionally R$_a$-substituted $C_6$-$C_{10}$ aromatic hydrocarbon group, or an optionally R$_a$-substituted monocyclic 4- to 7-membered unsaturated heterocyclic group having 1 to 3 heteroatoms selected from the group consisting of N, S and O, $R_2$ represents a hydrogen atom; a cyano group; a ($C_1$-$C_6$ alkoxy)carbonyl group; a carbamoyl group; a di- or mono-($C_1$-$C_6$ alkyl)carbamoyl group; a $C_1$-$C_6$ alkyl group optionally substituted with a group selected from the group consisting of a hydroxy group, a $C_1$-$C_6$ alkoxy group, a di- or mono-($C_1$-$C_6$ alkyl)amino group, and a 4- to 10-membered saturated heterocyclic group; a $C_1$-$C_6$ alkoxy group; or a monocyclic 5- or 6-membered completely unsaturated heterocyclic group having 1 to 3 N atoms, which is optionally substituted with a $C_1$-$C_6$ alkyl group, m represents 0, n represents 0 or 1, $R_4$ represents a $C_2$-$C_6$ alkenyl group, and in the formula (I), the following structure:

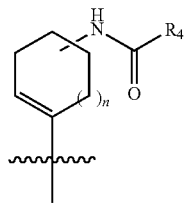

is any one of the following structures:

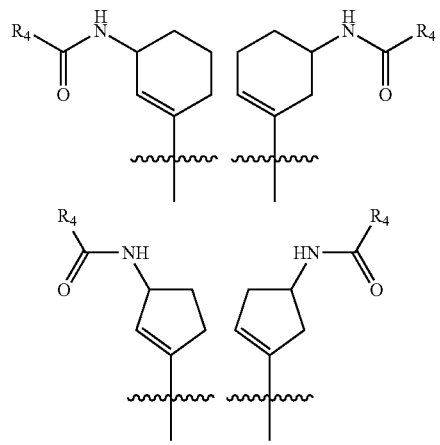

$R_a$ represents a halogen atom, a hydroxy group, a cyano group, a nitro group, an oxo group, an N-oxide group, —C(=O)R$_x$, —C(=O)OR$_x$, —C(=O)N(R$_x$)(R$_y$), —C(=O)SR$_x$, —C(=S)OR$_x$, —C(=O)ON(R$_x$)(R$_y$), —N(R$_x$)(R$_y$), —NR$_x$C(=O)R$_y$, —NR$_x$S(=O)$_2$R$_y$, —NR$_x$C(=O)OR$_y$, —NR$_x$C(=O)N(R$_y$)(R$_z$), —NR$_x$S(=O)$_2$N(R$_y$)(R$_z$), —N(R$_x$)—OR$_y$, =NR$_x$, =N—OR$_x$, —OC(=O)R$_x$, —OC(=S)R$_x$, —OC(=O)OR$_x$, —OC(=O)N(R$_x$)(R$_y$), —OC(=S) OR$_x$, —SR$_x$, —S(=O)$_2$R$_x$, —S(=O)$_2$OR$_x$, —S(=O)$_2$N(R$_x$)(R$_y$), an optionally R$_b$-substituted $C_1$-$C_6$ alkyl group, an optionally R$_b$-substituted $C_2$-$C_6$ alkenyl group, an optionally R$_b$-substituted $C_2$-$C_6$ alkynyl group, an optionally R$_b$-substituted $C_1$-$C_6$ alkoxy group, an optionally R$_c$-substituted $C_3$-$C_{10}$ cycloalkyl group, an optionally R$_c$-substituted $C_6$-$C_{14}$ aromatic hydrocarbon group, or an optionally R$_c$-substituted 4- to 10-membered saturated or unsaturated heterocyclic group, $R_b$ represents a halogen atom, an amino group, a hydroxy group, a cyano group, a nitro group, a $C_1$-$C_6$ alkoxy group, a di- or mono-($C_1$-$C_6$ alkyl)amino group, or a 4- to 10-membered saturated or unsaturated heterocyclic group, $R_c$ represents a halogen atom, an amino group, a hydroxy group, a cyano group, a nitro group, an oxo group, an imino group, an N-oxide group, a $C_1$-$C_6$ alkyl group, a $C_2$-$C_6$ alkenyl group, a $C_2$-$C_6$ alkynyl group, a $C_1$-$C_6$ alkoxy group or a di- or mono-($C_1$-$C_6$ alkyl)amino group, and $R_x$, $R_y$ and $R_z$, which are the same or different, each represent a hydrogen atom, a $C_1$-$C_6$ alkyl group, a $C_1$-$C_6$ haloalkyl group, a $C_2$-$C_6$ alkenyl group, a $C_2$-$C_6$ alkynyl group, a $C_3$-$C_{10}$ cycloalkyl group, a $C_6$-$C_{14}$ aromatic hydrocarbon group, or a 4- to 10-membered saturated or unsaturated heterocyclic group.

The compound of the present invention is even more preferably a compound in which $R_1$ represents an optionally R$_a$-substituted cyclopentenyl group, cyclohexenyl group, phenyl group, furanyl group, 1H-pyrazolyl group, thiazolyl group, oxazolyl group, isoxazolyl group, 1,3,4-thiadiazolyl group, 1,2,4-oxadiazolyl group, 1,3,4-oxadiazolyl group, pyridyl group, dihydropyranyl group, dihydrofuranyl group, or 4,5-dihydro-1,3,4-oxadiazolyl group, $R_2$ represents a hydrogen atom; a cyano group; a ($C_1$-$C_6$ alkoxy)carbonyl group; a carbamoyl group; a di- or mono-($C_1$-$C_6$ alkyl)carbamoyl group; a $C_1$-$C_6$ alkyl group optionally substituted with a group selected from the group consisting of a hydroxy group, a $C_1$-$C_6$ alkoxy group, a di- or mono-($C_1$-$C_6$ alkyl)amino group, and a 4- to 10-membered saturated heterocyclic group; a $C_1$-$C_6$ alkoxy group; or a monocyclic 5- or 6-membered completely unsaturated heterocyclic group having 1 to 3 N atoms, which is optionally substituted with a $C_1$-$C_6$ alkyl group, m represents 0, n represents 0 or 1, $R_4$ represents a $C_2$-$C_6$ alkenyl group, and in the formula (I), the following structure:

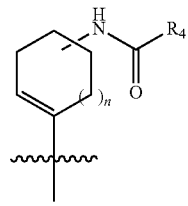

is any one of the following structures:

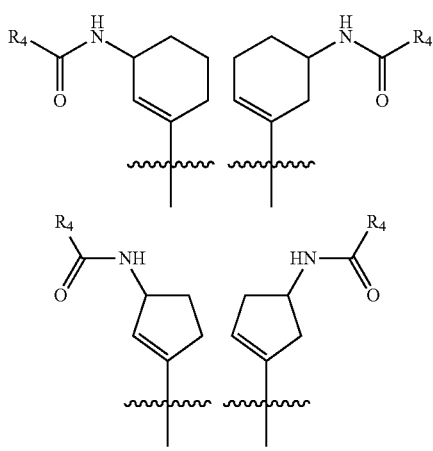

$R_a$ represents a halogen atom, a hydroxy group, a cyano group, a nitro group, an oxo group, an N-oxide group, —C(=O)$R_x$, —C(=O)O$R_x$, —C(=O)N($R_x$)($R_y$), —C(=O)S$R_x$, —C(=S)O$R_x$, —C(=O)ON($R_x$)($R_y$), —N($R_x$)($R_y$), —$NR_x$C(=O)$R_y$, —$NR_x$S(=O)$_2R_y$, —$NR_x$C(=O)O$R_y$, —$NR_x$C(=O)N($R_y$)($R_z$), —$NR_x$S(=O)$_2$N($R_y$)($R_z$), —N($R_x$)—O$R_y$, =N$R_x$, =N—O$R_x$, —OC(=O)$R_x$, —OC(=S)$R_x$, —OC(=O)O$R_x$, —OC(=O) N($R_x$)($R_y$), —OC(=S) O$R_x$, —S$R_x$, —S(=O)$_2R_x$, —S(=O)$_2$O$R_x$, —S(=O)$_2$N($R_x$)($R_y$), an optionally $R_b$-substituted $C_1$-$C_6$ alkyl group, an optionally $R_b$-Substituted $C_2$-$C_6$ alkenyl group, an optionally $R_b$-substituted $C_2$-$C_6$ alkynyl group, an optionally $R_b$-substituted $C_1$-$C_6$ alkoxy group, an optionally $R_c$-substituted $C_3$-$C_{10}$ cycloalkyl group, an optionally $R_c$-substituted $C_6$-$C_{14}$ aromatic hydrocarbon group, or an optionally $R_c$-substituted 4- to 10-membered saturated or unsaturated heterocyclic group, $R_b$ represents a halogen atom, an amino group, a hydroxy group, a cyano group, a nitro group, a $C_1$-$C_6$ alkoxy group, a di- or mono-($C_1$-$C_6$ alkyl)amino group, or a 4- to 10-membered saturated or unsaturated heterocyclic group, $R_c$ represents a halogen atom, an amino group, a hydroxy group, a cyano group, a nitro group, an oxo group, an imino group, an N-oxide group, a $C_1$-$C_6$ alkyl group, a $C_2$-$C_6$ alkenyl group, a $C_2$-$C_6$ alkynyl group, a $C_1$-$C_6$ alkoxy group or a di- or mono-($C_1$-$C_6$ alkyl)amino group, and $R_x$, $R_y$ and $R_z$, which are the same or different, each represent a hydrogen atom, a $C_1$-$C_6$ alkyl group, a $C_1$-$C_6$ haloalkyl group, a $C_2$-$C_6$ alkenyl group, a $C_2$-$C_6$ alkynyl group, a $C_3$-$C_{10}$ cycloalkyl group, a $C_6$-$C_{14}$ aromatic hydrocarbon group, or a 4- to 10-membered saturated or unsaturated heterocyclic group.

The compound of the present invention is further preferably a compound in which $R_1$ represents a cyclopentenyl group, a cyclohexenyl group, a phenyl group, a furanyl group, a 1H-pyrazolyl group, a thiazolyl group, an oxazolyl group, an isoxazolyl group, a 1,3,4-thiadiazolyl group, a 1,2,4-oxadiazolyl group, a 1,3,4-oxadiazolyl group, a pyridyl group, a dihydropyranyl group, a dihydrofuranyl group, or a 4,5-dihydro-1,3,4-oxadiazolyl group, which is optionally substituted with a group selected from the group consisting of a halogen atom, an amino group, a hydroxy group, an oxo group, an N-oxide group, a formyl group, a $C_1$-$C_6$ alkyl group (which is optionally substituted with a group selected from the group consisting of a hydroxy group and a di- or mono-($C_1$-$C_6$ alkyl)amino group), a $C_1$-$C_6$ alkoxy group (which is optionally substituted with a halogen atom), and a 4- to 10-membered saturated heterocyclic group, $R_2$ represents a hydrogen atom; a cyano group; a ($C_1$-$C_6$ alkoxy)carbonyl group; a carbamoyl group; a di- or mono-($C_1$-$C_6$ alkyl)carbamoyl group; a $C_1$-$C_6$ alkyl group optionally substituted with a group selected from the group consisting of a hydroxy group, a $C_1$-$C_6$ alkoxy group, a di- or mono-($C_1$-$C_6$ alkyl)amino group, and a 4- to 10-membered saturated heterocyclic group; a $C_1$-$C_6$ alkoxy group; or a monocyclic 5- or 6-membered completely unsaturated heterocyclic group having 1 to 3 N atoms, which is optionally substituted with a $C_1$-$C_6$ alkyl group, m represents 0, n represents 0 or 1, $R_4$ represents a $C_2$-$C_6$ alkenyl group, and in the formula (I), the following structure:

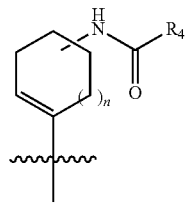

is any one of the following structures:

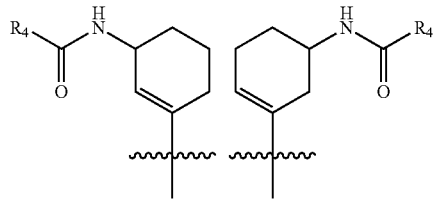

-continued

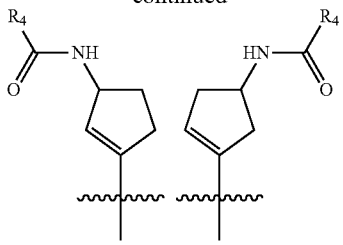

The compound of the present invention is particularly preferably a compound in which $R_1$ represents a cyclopentenyl group; a cyclohexenyl group; a phenyl group; a furanyl group optionally substituted with a group selected from the group consisting of a formyl group and a $C_1$-$C_6$ alkyl group (which is optionally substituted with a group selected from the group consisting of a hydroxy group and a di- or mono-($C_1$-$C_6$ alkyl)amino group); a 1H-pyrazolyl group optionally substituted with a group selected from the group consisting of a $C_1$-$C_6$ alkyl group and a 4- to 10-membered saturated heterocyclic group; a thiazolyl group; an oxazolyl group; an isoxazolyl group; an 1,3,4-thiadiazolyl group; an 1,2,4-oxadiazolyl group; a 1,3,4-oxadiazolyl group optionally substituted with a $C_1$-$C_6$ alkyl group; a pyridyl group optionally substituted with a group selected from the group consisting of a halogen atom, an amino group, a hydroxy group, an N-oxide group, a $C_1$-$C_6$ alkyl group (which is optionally substituted with a hydroxy group) and a $C_1$-$C_6$ alkoxy group (which is optionally substituted with a halogen atom); a dihydropyranyl group; a dihydrofuranyl group; or a 4,5-dihydro-1,3,4-oxadiazolyl group optionally substituted with a group selected from the group consisting of an oxo group and a $C_1$-$C_6$ alkyl group, $R_2$ represents a hydrogen atom; a cyano group; a ($C_1$-$C_6$ alkoxy)carbonyl group; a carbamoyl group; a di- or mono-($C_1$-$C_6$ alkyl)carbamoyl group; a $C_1$-$C_6$ alkyl group optionally substituted with a group selected from the group consisting of a hydroxy group, a $C_1$-$C_6$ alkoxy group, a di- or mono-($C_1$-$C_6$ alkyl)amino group, and a 4- to 10-membered saturated heterocyclic group; a $C_1$-$C_6$ alkoxy group; or a monocyclic 5- or 6-membered completely unsaturated heterocyclic group having 1 to 3 N atoms, which is optionally substituted with a $C_1$-$C_6$ alkyl group, m represents 0, n represents 0 or 1, $R_4$ represents a $C_2$-$C_6$ alkenyl group, and in the formula (I), the following structure:

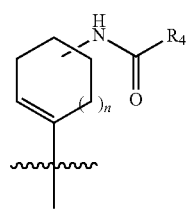

is any one of the following structures:

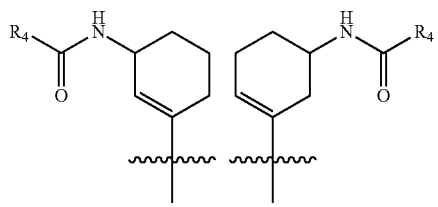

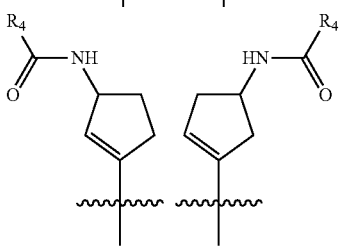

Specific examples of the preferred compound of the present invention include:
(1) N-(3-(3-phenyl-1H-pyrrolo[2,3-b]pyridin-4-yl)cyclohex-3-en-1-yl)acrylamide (Compound 1),
(2) N-(3-(3-(1H-pyrazol-4-yl)-1H-pyrrolo[2,3-b]pyridin-4-yl)cyclohex-3-en-1-yl)acrylamide (Compound 3),
(3) N-(3-(3-(2-methoxypyridin-3-yl)-1H-pyrrolo[2,3-b]pyridin-4-yl)cyclohex-3-en-1-yl)acrylamide (Compound 6),
(4) N-(3-(3-(furan-2-yl)-1H-pyrrolo[2,3-b]pyridin-4-yl)cyclohex-3-en-1-yl)acrylamide (Compound 12),
(5) N-(3-(3-(4-(hydroxymethyl)furan-2-yl)-1H-pyrrolo[2,3-b]pyridin-4-yl)cyclohex-3-en-1-yl)acrylamide (Compound 14),
(6) N-(3-(3-(2,5-dihydrofuran-3-yl)-1H-pyrrolo[2,3-b]pyridin-4-yl)cyclohex-3-en-1-yl)acrylamide (Compound 34),
(7) N-(3-(3-(oxazol-5-yl)-1H-pyrrolo[2,3-b]pyridin-4-yl)cyclohex-3-en-1-yl)acrylamide (Compound 48),
(8) N-(3-(3-(1,3,4-oxadiazol-2-yl)-1H-pyrrolo[2,3-b]pyridin-4-yl)cyclohex-3-en-1-yl)acrylamide (Compound 49),
(9) (S)-N-(3-(3-(1,3,4-oxadiazol-2-yl)-1H-pyrrolo[2,3-b]pyridin-4-yl)cyclohex-3-en-1-yl)acrylamide (Compound 55),
(10) N-(3-(3-(1,3,4-oxadiazol-2-yl)-1H-pyrrolo[2,3-b]pyridin-4-yl)cyclopent-3-en-1-yl)acrylamide (Compound 57), and
(11) (S)-N-(3-(3-(isoxazol-5-yl)-1H-pyrrolo[2,3-b]pyridin-4-yl)cyclohex-3-en-1-yl)acrylamide (Compound 59).

Next, methods for producing the compound according to the present invention will be described.

The compound of the present invention of formula (I) can be produced by, for example, the following Production Methods A to E.

<Production Method A>

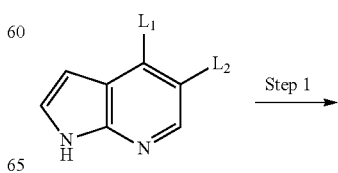

27
-continued

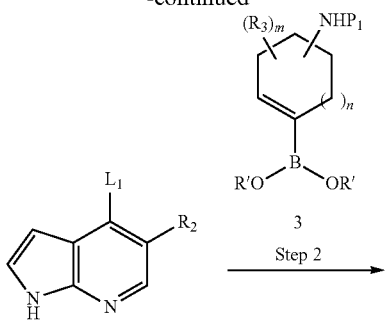

Step 2

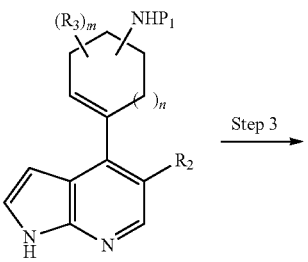

Step 3

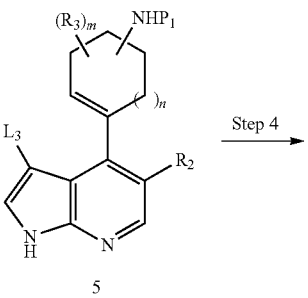

Step 4

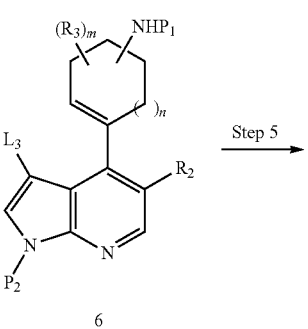

Step 5

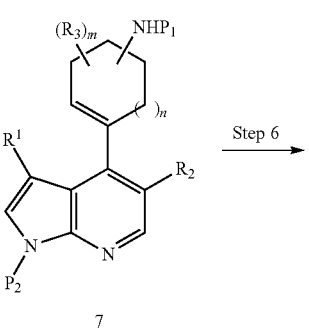

Step 6

28
-continued

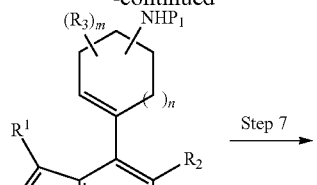

Step 7

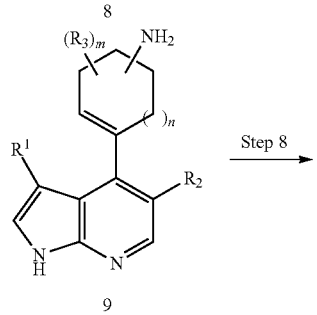

Step 8

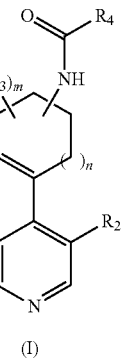

(I)

where $L_1$, $L_2$, and $L_3$, which are the same or different, each represent a leaving group, $P_1$ and $P_2$ each represent a protective group, and other symbols have the same meanings as described above.

(Step 1)

This step is a method of allowing the compound of formula 1 to react with arylboronic acid or arylboronic acid ester, or with unsaturated hetero ring-boronic acid or unsaturated hetero ring-boronic acid ester, each of which is a commercially available product or can be produced by a known method, according to a coupling reaction, when $L_2$ in the compound of formula 1 has a leaving group such as halogen, so as to obtain the compound of formula 2.

This step can be generally carried out according to a known method (for example, Chemical Reviews, Vol. 95, p. 2457, 1995), and it can be carried out, for example, in the presence of a transition metal catalyst and a base, in a solvent which does not adversely affect the reaction.

The arylboronic acid or arylboronic acid ester, or unsaturated hetero ring-boronic acid or unsaturated hetero ring-boronic acid ester can be used in an amount of from 1 to 10 equivalents, and preferably from 1 to 3 equivalents, based on the amount of the compound of formula 1 (1 mole)

Examples of the transition metal catalyst used herein include palladium catalysts (e.g., palladium acetate, palladium chloride, and tetrakis(triphenylphosphine)palladium) and nickel catalysts (e.g., nickel chloride). As necessary, a ligand (e.g., triphenylphosphine and tri-tert-butylphosphine)

is added to the catalyst, and a metal oxide (e.g., copper oxide and silver oxide) and the like may be used as a co-catalyst. The amount of the transition metal catalyst to be used varies depending on the type of the catalyst, and the transition metal catalyst is used in an amount of generally from about 0.0001 to 1 mole, and preferably from about 0.01 to 0.5 moles, based on the amount of the compound of formula 1 (1 mole). The ligand is used in an amount of generally from about 0.0001 to 4 moles, and preferably from about 0.01 to 2 moles, based on the amount of the compound of formula 1 (1 mole), and the co-catalyst is used in an amount of generally from about 0.0001 to 4 moles, and preferably from about 0.01 to 2 moles, based on the amount of the compound of formula 1 (1 mole).

Examples of the base include organic amines (e.g., trimethylamine, triethylamine, diisopropylethylamine, N-methylmorpholine, 1,8-diazabicyclo[5,4,0]undec-7-ene, pyridine, and N,N-dimethylaniline), alkaline metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide), metal hydrides (e.g., potassium hydride and sodium hydride), alkaline metal alkoxides (e.g., sodium methoxide, sodium ethoxide, sodium tert-butoxide, and potassium tert-butoxide), and alkaline metal disilazides (e.g., lithium disilazide, sodium disilazide, and potassium disilazide). The base is used in an amount of generally from 0.1 to 10 moles, and preferably from about 1 to 5 moles, based on the amount of the compound of formula 1 (1 mole).

The solvent is not particularly limited, as long as it does not adversely affect the reaction. Examples of the solvent include hydrocarbons (e.g., benzene, toluene, and xylene), halogenated hydrocarbons (e.g., chloroform and 1,2-dichloroethane), nitriles (e.g., acetonitrile), ethers (e.g., dimethoxyethane and tetrahydrofuran), alcohols (e.g., methanol and ethanol), aprotic polar solvents (e.g., dimethylformamide, dimethyl sulfoxide, and hexamethylphosphoramide), water, and the mixtures thereof.

The reaction time is from 0.1 to 100 hours, and preferably from 0.5 to 24 hours. The reaction temperature is from 0° C. to the boiling point of the solvent, and preferably from 0° C. to 150° C.

Thus obtained compound of formula 2 can be isolated and purified by a known separation purification means, or it can be subjected to the subsequent step without such isolation and purification.
(Step 2)

This step is a method of allowing the compound of formula 2 to react with the compound of formula 3, which is a commercially available product or can be produced by a known method, according to a coupling reaction, so as to obtain the compound of formula 4. This step can be carried out by the same method as that in Step 1.
(Step 3)

This step is a method of halogenating the compound of formula 4 to obtain the compound of formula 5. The halogenation can be carried out, for example, by a method of using fluorine, chlorine, bromine, iodine, etc., or a method of using N-chlorosuccinimide, N-bromosuccinimide or N-iodosuccinimide. In this reaction, a method of using N-chlorosuccinimide, N-bromosuccinimide, N-iodosuccinimide, etc. is preferable.

Such N-chlorosuccinimide, N-bromosuccinimide, N-iodosuccinimide, etc. can be used in an amount of from 1 to 10 equivalents, and preferably from 1 to 3 equivalents, based on the amount of the compound of formula 4 (1 mole).

The solvent is not particularly limited, as long as it does not adversely affect the reaction. Examples of the solvent include hydrocarbons (e.g., benzene, toluene, and xylene), halogenated hydrocarbons (e.g., chloroform and 1,2-dichloroethane), nitriles (e.g., acetonitrile), ethers (e.g., dimethoxyethane and tetrahydrofuran), alcohols (e.g., methanol and ethanol), aprotic polar solvents (e.g., dimethylformamide, dimethyl sulfoxide, and hexamethylphosphoramide), water, and the mixtures thereof.

The reaction time is from 0.1 to 100 hours, and preferably from 0.5 to 24 hours. The reaction temperature is from 0° C. to the boiling point of the solvent, and preferably from 0° C. to 100° C.

Thus obtained compound of formula 5 can be isolated and purified by a known separation purification means, or it can be subjected to the subsequent step without such isolation and purification.
(Step 4)

This step is a method of introducing a protective group into the compound of formula 5 to obtain the compound of formula 6. The protection can be carried out by a generally known method, for example, the method described in Protective Groups in Organic Synthesis, T. W. Greene, John Wiley & Sons (1981), or a method equivalent thereto. In this reaction, a toluenesulfonate group, a benzenesulfonate group, a methanesulfonate group, a 2-(trimethylsilyl)ethoxymethyl group, a methoxymethyl group, a trityl group, and the like are preferable.

Examples of the protective group agent used in this reaction include toluenesulfonyl chloride, benzenesulfonyl chloride, methanesulfonyl chloride, 2-(chloromethoxy)ethyltrimethylsilane, chloro(methoxy)methane, and trityl chloride. Such a protective group agent is used in an amount of generally from about 1 to 100 moles, and preferably from about 1 to 10 moles, based on the amount of the compound of formula 5 (1 mole).

Examples of the base include organic amines (e.g., trimethylamine, triethylamine, diisopropylethylamine, N-methylmorpholine, 1,8-diazabicyclo[5,4,0]undec-7-ene, pyridine, and N,N-dimethylaniline), alkaline metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide), metal hydrides (e.g., potassium hydride and sodium hydride), alkaline metal alkoxides (e.g., sodium methoxide, sodium ethoxide, sodium tert-butoxide, and potassium tert-butoxide), and alkaline metal disilazides (e.g., lithium disilazide, sodium disilazide, and potassium disilazide). The base is used in an amount of generally from 0.1 to 100 moles, and preferably from about 1 to 10 moles, based on the amount of the compound of formula 5 (1 mole).

The solvent is not particularly limited, as long as it does not adversely affect the reaction. Examples of the solvent include hydrocarbons (e.g., benzene, toluene, and xylene), halogenated hydrocarbons (e.g., chloroform and 1,2-dichloroethane), nitriles (e.g., acetonitrile), ethers (e.g., dimethoxyethane and tetrahydrofuran), alcohols (e.g., methanol and ethanol), aprotic polar solvents (e.g., dimethylformamide, dimethyl sulfoxide, and hexamethylphosphoramide), water, and the mixtures thereof.

The reaction time is from 0.1 to 100 hours, and preferably from 0.5 to 24 hours. The reaction temperature is from 0° C. to the boiling point of the solvent, and preferably from 0° C. to 100° C.

Thus obtained compound of formula 6 can be isolated and purified by a known separation purification means, or it can be subjected to the subsequent step without such isolation and purification.

(Step 5)

This step is a method of allowing the compound of formula 6 to react with arylboronic acid or arylboronic acid ester, or with unsaturated hetero ring-boronic acid or unsaturated hetero ring-boronic acid ester, each of which is a commercially available product or can be produced by a known method, according to a coupling reaction, or of allowing the compound of formula 6 to react with an organic tin compound which is a commercially available product or can be produced by a known method, according to a coupling reaction, so as to obtain the compound of formula 7.

This step can be carried out by the same method as that in Step 1.

(Step 6)

This step is a method of deprotecting the protective group $P_2$ of the compound of formula 7 to obtain the compound of formula 8. The deprotection can be carried out by a generally known method, for example, the method described in Protective Groups in Organic Synthesis, T. W. Greene, John Wiley & Sons (1981), or a method equivalent thereto.

Examples of the protective group include a para-toluenesulfonic acid group and a trimethylsilylethoxymethyl group. When a para-toluenesulfonic acid group is used as a protective group, for example, lithium hydroxide, sodium hydroxide, potassium hydroxide, tetrabutylammonium fluoride, etc. are preferably used. Such a protective group is used in an amount of generally from 0.5 to 100 moles, and preferably from about 1 to 10 moles, based on the amount of the compound of formula 7 (1 mole).

Moreover, when the protective group $P_2$ is a trimethylsilylethoxymethyl group or a trityl group, lithium hydroxide, sodium hydroxide, potassium hydroxide, tetrabutylammonium fluoride, acid (e.g., hydrochloric acid, trifluoroacetic acid, acetic acid, and sulfuric acid) and the like are preferably used. Such a protective group is used in an amount of generally from 0.5 to 100 moles, and preferably from about 1 to 10 moles, based on the amount of the compound of formula 7 (1 mole).

The solvent used in the reaction is not particularly limited, as long as it does not adversely affect the reaction. Examples of the solvent used herein include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane and tetrahydrofuran), aprotic polar solvents (e.g., N,N-dimethylformamide, dimethyl sulfoxide, and hexamethylphosphoramide), and the mixtures thereof.

The reaction time is from 0.1 to 100 hours, and preferably from 0.5 to 24 hours. The reaction temperature is from 0° C. to the boiling point of the solvent, and preferably from 0° C. to 100° C.

Thus obtained compound of formula 8 can be isolated and purified by a known separation purification means, or it can be subjected to the subsequent step without such isolation and purification.

(Step 7)

This step is a method of deprotecting the protective group for the amino group of the compound of formula 8 to obtain the compound of formula 9. The deprotection can be carried out by a generally known method, for example, the method described in Protective Groups in Organic Synthesis, T. W. Greene, John Wiley & Sons (1981), or a method equivalent thereto.

An example of such a protective group is tert-butyloxycarbonyl. When a tert-butyloxycarbonyl group is used as a protective group, for example, the deprotection is preferably carried out under acidic conditions. Examples of the acid include hydrochloric acid, acetic acid, trifluoroacetic acid, sulfuric acid, and tosic acid. The acid is used in an amount of preferably from about 1 to 100 equivalents based on the amount of the compound of formula 8 (1 mole).

The solvent used in the reaction is not particularly limited, as long as it does not adversely affect the reaction. Examples of the solvent used herein include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane and tetrahydrofuran), aprotic polar solvents (e.g., N,N-dimethylformamide, dimethyl sulfoxide, and hexamethylphosphoramide), and the mixtures thereof.

The reaction time is from 0.1 to 100 hours, and preferably from 0.5 to 24 hours. The reaction temperature is from 0° C. to 100° C., and preferably from 0° C. to 50° C.

Thus obtained compound of formula 9 can be isolated and purified by a known separation purification means, or it can be subjected to the subsequent step without such isolation and purification.

(Step 8)

This step is a method of allowing the amino group of the compound of formula 9 to react with carboxylic acid represented by $R_4$—COOH or with an acid halide represented by $R_4$—C(=O)-L (where L represents a chlorine atom or a bromine atom) according to an amidation reaction, so as to obtain the compound of the present invention of formula (I).

When carboxylic acid represented by $R_4$—COOH is used, the carboxylic acid is used in an amount of generally from 0.5 to 10 moles, and preferably from about 1 to 5 moles, based on the amount of the compound of formula 9 (1 mole) in the presence of a condenser. Note that the carboxylic acid is a commercially available product or can be produced according to a known method.

Example of the condenser include N,N'-dicyclohexylcarbodiimide (DCC), N,N'-diisopropylcarbodiimide (DIC), 1-ethyl-3-(3-dimethylaminopropyl)carbodiimide hydrochloride (WSC), diphenylphosphoryl azide (DPPA), benzotriazol-1-yl-oxytrisdimethylaminophosphonium hexafluorophosphate (BOP), benzotriazol-1-yl-oxytripyrrolidinophosphonium hexafluorophosphate (PyBOP), 7-azabenzotriazol-1-yloxytrispyrrolidinophosphonium phosphate (PyAOP), bromotrispyrrolidinophosphonium hexafluorophosphate (BroP), chlorotris(pyrrolidin-1-yl)phosphonium hexafluorophosphate (PyCroP), 3-(diethoxyphosphoryloxy)-1,2,3-benzotriazin-4(3H)-one (DEPBT), O-(benzotriazol-1-yl)-N,N,N',N'-tetramethyluronium hexafluorophosphate (HATU), and 4-(5,6-dimethoxy-1,3,5-triazin-2-yl)-4-methylmorpholine hydrochloride (DMTMM). Examples of the additive used herein include 1-hydroxybenzotriazole (HOBt), 1-hydroxy-7-azabenzotriazole (HOAt), and N-hydroxysuccinimide (HOSu). Such a substance is used in an amount of generally from 1 to 100 moles, and preferably from about 1 to 10 moles, based on the amount of the compound of formula 9 (1 mole).

In addition, a base can be added, as necessary. Examples of such a base include organic amines (e.g., trimethylamine, triethylamine, diisopropylethylamine, N-methylmorpholine, 1,8-diazabicyclo[5,4,0]undec-7-ene, pyridine, and N,N-dimethylaniline), alkaline metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide), metal hydrides (e.g., potassium hydride and sodium hydride), and alkaline metal alkoxides (e.g., sodium methoxide, sodium ethoxide, sodium tert-butoxide, and potassium tert-butoxide). The base is used in an amount of generally from 1 to 100 moles, and preferably from about 1 to 10 moles, based on the amount of the compound of formula 9 (1 mole).

The solvent used in the reaction is not particularly limited, as long as it does not adversely affect the reaction. Examples of the solvent used herein include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane and tetrahydrofuran), aprotic polar solvents (e.g., N,N-dimethylformamide, dimethyl sulfoxide, and hexamethylphosphoramide), and the mixtures thereof.

The reaction time is from 0.1 to 100 hours, and preferably from 0.5 to 24 hours. The reaction temperature is from 0° C. to the boiling point of the solvent, and preferably from 0° C. to 100° C.

When an acid halide represented by $R_4$—C(=O)-L (where L represents a chlorine atom or a bromine atom) is used, the acid halide is used in an amount of generally from 0.5 to 10 moles, and preferably from about 1 to 5 moles, based on the amount of the compound of formula 9 (1 mole). Note that the acid halide is a commercially available product or can be produced according to a known method.

In addition, a base can be added, as necessary. Examples of such a base include organic amines (e.g., trimethylamine, triethylamine, diisopropylethylamine, N-methylmorpholine, 1,8-diazabicyclo[5,4,0]undec-7-ene, pyridine, and N,N-dimethylaniline), alkaline metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide), metal hydrides (e.g., potassium hydride and sodium hydride), and alkaline metal alkoxides (e.g., sodium methoxide, sodium ethoxide, sodium tert-butoxide, and potassium tert-butoxide). The base is used in an amount of generally from 1 to 100 moles, and preferably from about 1 to 10 moles, based on the amount of the compound of formula 9 (1 mole).

The solvent used in the reaction is not particularly limited, as long as it does not adversely affect the reaction. Examples of the solvent used herein include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane and tetrahydrofuran), aprotic polar solvents (e.g., N,N-dimethylformamide, dimethyl sulfoxide, and hexamethylphosphoramide), and the mixtures thereof.

The reaction time is from 0.1 to 100 hours, and preferably from 0.5 to 24 hours. The reaction temperature is from 0° C. to the boiling point of the solvent, and preferably from 0° C. to 100° C.

Thus obtained compound of the present invention of formula (I) can be isolated and purified by a known separation purification means such as concentration, vacuum concentration, crystallization, solvent extraction, reprecipitation or chromatography.

Moreover, in Production Method A, "connection of an azaindole skeleton with the compound of formula 3," "introduction of $R_1$ into the azaindole skeleton," and "deprotection of $P_1$ and introduction of —C(=O)—$R_4$" are carried out in this order. However, this order can be changed. That is to say, the compound can also be synthesized in the order of "introduction of $R_1$ into an azaindole skeleton," "connection of the azaindole skeleton with the compound of formula 3," and "deprotection of $P_1$ and introduction of —C(=O)—$R_4$." Specifically, the compound of formula 2 is subjected to individual steps in the order of Step 3, Step 4, Step 5, and Step 2, so that it can be induced to the compound of formula 7. The conditions applied to each step are the same as those described above. In addition, the compound can also be synthesized in the order of "connection of an azaindole skeleton with the compound of formula 3," "deprotection of $P_1$ and introduction of —C(=O)—$R_4$," and "introduction of $R_1$ into the azaindole skeleton." Specifically, the compound of formula 6 is subjected to individual steps in the order of Step 7, Step 8, Step 5, and Step 6, so that it can be induced to the compound of the present invention of formula (I).

Furthermore, in a suitable intermediate in Production Method A, one substituent represented by $R_2$ can be converted to another substituent represented by $R_2$. For example, a formyl group can be converted to a methyl group substituted with a di- or mono-alkylamino group, a formyl group can be converted to a hydroxymethyl group, an ester group can be converted to a carboxy group, and an ester group can be converted to an amide group. Conversion of the substituents is not limited thereto, and conversions described in known publications and the like are also included. Conversion of the substituent $R_2$ from the compound of formula 7 to the compound of formula 8 is shown in Production Method B, and conversion of the substituent $R_2$ from the compound of formula 8 to the compound of formula 9 is shown in Production Methods C and D. Conversion of $R_2$ is not limited to these intermediates, and it can be carried out as appropriate.

Further, in Step 5 of Production Method A, a method of introducing $R_1$ into an azaindole skeleton has been described. Instead of this method, $R_1$ can also be derived from a formyl group. Such a method will be described in Production Method E.

<Production Method B>

Production Method B is a method of undergoing conversion of the substituent $R_2$ from the compound of formula 7 to the compound of formula 8, so as to obtain the compound of the present invention of formula (I).

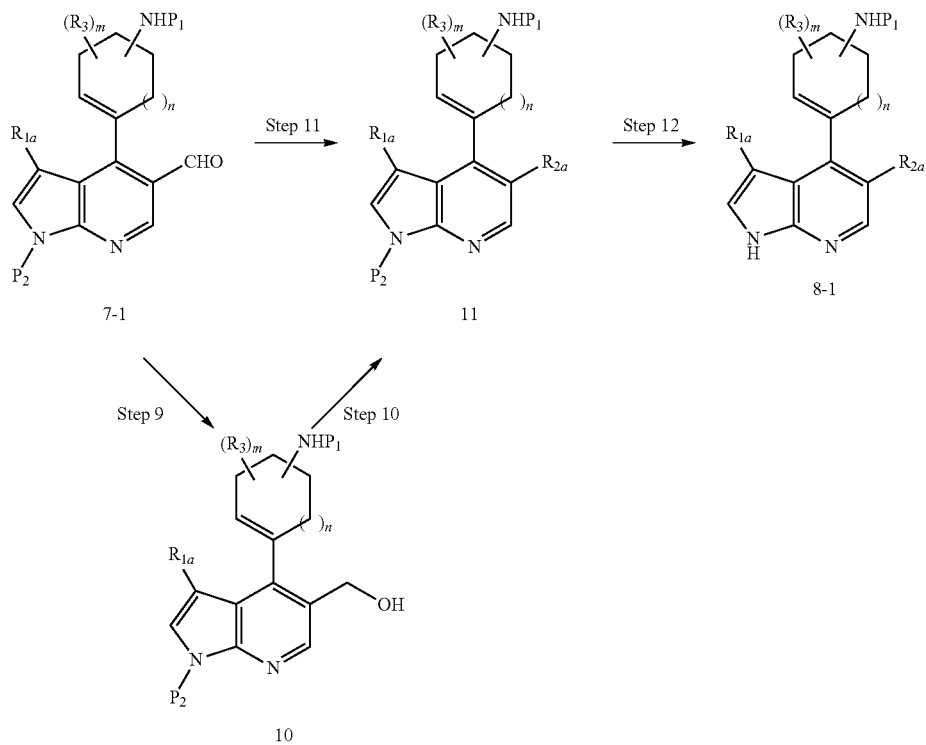

Conversion of the substituent in this production method is conversion of a formyl group to a methyl group substituted with a di- or mono-alkylamino group. The compound of formula 7-1 is the compound of formula 7, in which $R_2$ is a formyl group. The substituent $R_{1a}$ is a substituent having no formyl groups in the substituent $R_x$ thereof, among the substituents defined as $R_1$. The substituent $R_{2a}$ is a methyl group substituted with a di- or mono-alkylamino group, among the substituents defined as $R_2$. Other symbols have the same meanings as those described above.

(Step 9)

This step is a method of subjecting the compound of formula 7-1 to a reduction reaction, resulting in conversion to a hydroxymethyl group, so as to obtain the compound of formula 10.

Examples of the reducer include alkaline metal hydrides (e.g., sodium borohydride, lithium borohydride, sodium cyanoborohydride, sodium triacetoxyborohydride, and lithium aluminum hydride), metal hydrogen complex compounds (e.g., bis(2-methoxyethoxy)aluminum sodium hydride and diisobutyl aluminum hydride), and borane complexes (a borane tetrahydrofuran complex, a borane pyridine complex, etc.). The reducer is used in an amount of generally from about 0.1 to 100 moles, and preferably from about 1 to 10 moles, based on the amount of the compound of formula 7-1 (1 mole).

The solvent is not particularly limited, as long as it does not adversely affect the reaction. Examples of the solvent include hydrocarbons (e.g., benzene, toluene, and xylene), halogenated hydrocarbons (e.g., chloroform and 1,2-dichloroethane), nitriles (e.g., acetonitrile), ethers (e.g., dimethoxyethane and tetrahydrofuran), alcohols (e.g., methanol and ethanol), aprotic polar solvents (e.g., dimethylformamide, dimethyl sulfoxide, and hexamethylphosphoramide), water, and the mixtures thereof.

The reaction time is from 0.1 to 100 hours, and preferably from 0.5 to 24 hours. The reaction temperature is from 0° C. to the boiling point of the solvent, and preferably from 0° C. to 100° C.

Thus obtained compound of formula 10 can be isolated and purified by a known separation purification means, or it can be subjected to the subsequent step without such isolation and purification.

(Step 10)

This step is a method of subjecting the compound of formula 10 to a Mitsunobu reaction to obtain the compound of formula 11.

Examples of the Mitsunobu reagent used herein include diethyl azodicarboxylate and diisopropyl azodicarboxylate. The Mitsunobu reagent is used in an amount of generally from about 1 to 100 moles, and preferably from about 1 to 10 moles, based on the amount of the compound of formula 10 (1 mole).

Examples of the phosphine reagent used herein include triphenylphosphine, tributylphosphine, and trifurylphosphine. The phosphine reagent is used in an amount of generally from about 1 to 100 moles, and preferably from about 1 to 10 moles, based on the amount of the compound of formula 10 (1 mole).

The solvent is not particularly limited, as long as it does not adversely affect the reaction. Examples of the solvent include hydrocarbons (e.g., benzene, toluene, and xylene), halogenated hydrocarbons (e.g., chloroform and 1,2-dichloroethane), nitriles (e.g., acetonitrile), ethers (e.g., dimethoxyethane and tetrahydrofuran), alcohols (e.g., methanol and ethanol), aprotic polar solvents (e.g., dimethylformamide, dimethyl sulfoxide, and hexamethylphosphoramide), water, and the mixtures thereof.

The reaction time is from 0.1 to 100 hours, and preferably from 0.5 to 24 hours. The reaction temperature is from 0° C. to the boiling point of the solvent, and preferably from 0° C. to 100° C.

Thus obtained compound of formula 11 can be isolated and purified by a known separation purification means, or it can be subjected to the subsequent step without such isolation and purification.

(Step 11)

This step is a method of allowing the compound of formula 7-1 to react with amines, which are commercially available products or can be obtained by a known method, according to a reductive amination reaction by the use of a reducer, so as to obtain the compound of formula 11.

Examples of the reducer used herein include metal hydrides such as sodium borohydride, lithium borohydride, sodium cyanoborohydride, sodium triacetoxyborohydride, lithium aluminum hydride, bis(2-methoxyethoxy)aluminum sodium hydride, a borane tetrahydrofuran complex, or diisobutyl aluminum hydride. Moreover, mineral acids such as hydrochloric acid or hydrobromic acid, organic acids such as acetic acid, paratoluenesulfonic acid or trifluoromethanesulfonic acid, or Lewis acids such as titanium tetrachloride or ytterbium trifluoromethanesulfonate may be added and used, as necessary. The reducer is used in an amount of generally from 0.5 to 100 moles, and preferably from about 0.5 to 10 moles, based on the amount of the compound of formula 7-1 (1 mole). The acid is used in an amount of generally from 0.5 to 100 moles, and preferably from about 1 to 10 moles, based on the amount of the compound of formula 7-1 (1 mole).

The solvent is not particularly limited, as long as it does not adversely affect the reaction. Examples of the solvent include hydrocarbons (e.g., benzene, toluene, and xylene), halogenated hydrocarbons (e.g., chloroform and 1,2-dichloroethane), nitriles (e.g., acetonitrile), ethers (e.g., dimethoxyethane and tetrahydrofuran), alcohols (e.g., methanol and ethanol), aprotic polar solvents (e.g., dimethylformamide, dimethyl sulfoxide, and hexamethylphosphoramide), water, and the mixtures thereof.

The reaction time is from 0.1 to 100 hours, and preferably from 0.5 to 24 hours. The reaction temperature is from 0° C. to the boiling point of the solvent, and preferably from 0° C. to 100° C.

Thus obtained compound of formula 11 can be isolated and purified by a known separation purification means, or it can be subjected to the subsequent step without such isolation and purification.

(Step 12)

This step is a method of deprotecting the protective group $P_2$ of the compound of formula 11 to obtain the compound of formula 8-1. This step can be carried out by the same method as that in Step 6.

Thus obtained compound of formula 8-1 was treated in the same manner as in the case of inducing the compound of formula 8 to the compound of the present invention of formula (I) in Production Method A, so as to obtain the compound of the present invention of formula (I).

<Production Method C>

Production Method C is a method of undergoing conversion of the substituent $R_2$ from the compound of formula 8 to the compound of formula 9, so as to obtain the compound of the present invention of formula (I).

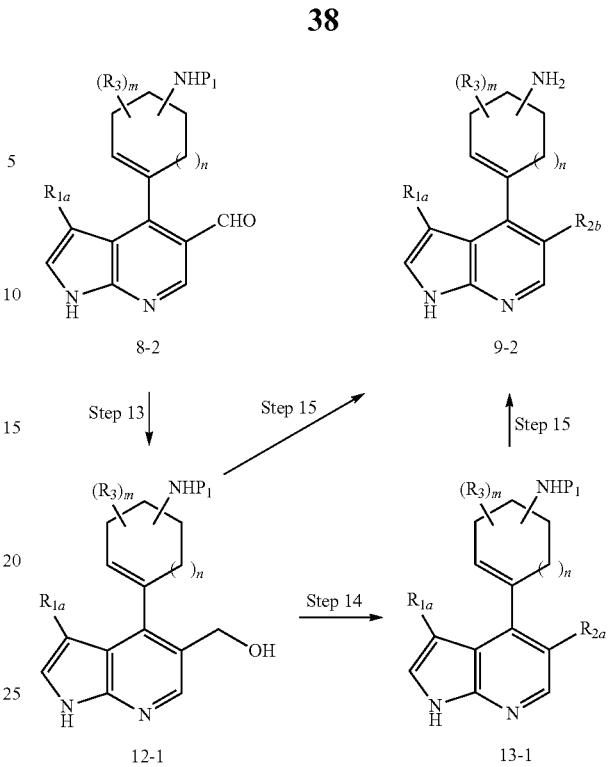

The conversion of the substituent is conversion of a formyl group to a methyl group substituted with a di- or mono-alkylamino group, and conversion of a formyl group to a hydroxymethyl group. The compound of formula 8-2 is the compound of formula 8, in which $R_2$ is a formyl group. The substituent $R_{2b}$ is a hydroxymethyl group, or a methyl group substituted with a di- or mono-alkylamino group, among the substituents defined as $R_2$. Other symbols have the same meanings as those described above.

(Step 13)

This step is a method of subjecting the formyl group of the compound of formula 8-2 to a reduction reaction so that it is converted to a hydroxymethyl group, so as to obtain the compound of formula 12-1. This step can be carried out by the same method as that in Step 9.

(Step 14)

This step is a method of subjecting the compound of formula 12-1 to a Mitsunobu reaction to obtain the compound of formula 13-1. This step can be carried out by the same method as that in Step 10.

(Step 15)

This step is a method of deprotecting the protective group for the amino group of the compound of formula 12-1 or the compound of formula 13-1, so as to obtain the compound of formula 9-2. This step can be carried out by the same method as that in Step 7.

Thus obtained compound of formula 9-2 can be isolated and purified by a known separation purification means, or it can be subjected to the subsequent step without such isolation and purification.

Thus obtained compound of formula 9-2 was treated in the same manner as in the case of inducing the compound of formula 9 to the compound of the present invention of formula (I) in Production Method A, so as to obtain the compound of the present invention of formula (I).

<Production Method D>

Production Method D is a method of undergoing conversion of the substituent $R_2$ from the compound of formula 8 to the compound of formula 9, so as to obtain the compound of the present invention of formula (I).

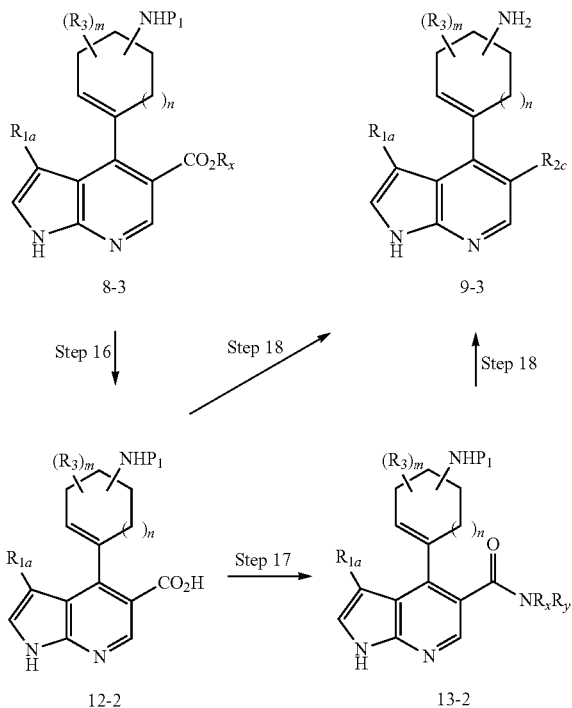

8-3

9-3

12-2

13-2

The compound of formula 8-3 is the compound of formula 8, in which $R_2$ represents an ester group $C(=O)OR_x$. The conversion of the substituent is conversion of the ester group to a carboxy group and an amide group. The substituent $R_{2c}$ is a carboxy group or a group represented by $-C(=O)-N(R_x)(R_y)$, among the substituents defined as $R_2$. Other symbols have the same meanings as those described above.

(Step 16)

This step is a method of subjecting the compound of formula 8-3 to a hydrolysis reaction under basic conditions, so as to obtain the compound of formula 12-2.

Examples of the base, which is preferably used herein, include sodium hydrogen carbonate, sodium carbonate, potassium carbonate, cesium carbonate, sodium hydroxide, potassium hydroxide, and lithium hydroxide. The base is used in an amount of generally from 0.5 to 100 moles, and preferably from about 1 to 10 moles, based on the amount of the compound of formula 8-3 (1 mole).

The solvent is not particularly limited, as long as it does not adversely affect the reaction. Examples of the solvent include water, methanol, ethanol, isopropanol, tetrahydrofuran, 1,4-dioxane, and N,N-dimethylformamide. These solvents can be used alone or in combination. The reaction time is from 0.1 to 100 hours, and preferably from 0.5 to 24 hours. The reaction temperature is from 0° C. to the boiling point of the solvent, and preferably from 0° C. to 100° C. Thus obtained compound of formula 12-2 can be isolated and purified by a known separation purification means, or it can be subjected to the subsequent step without such isolation and purification.

(Step 17)

This step is a method of subjecting the compound of formula 12-2 and amine to an amidation reaction to obtain the compound of formula 13-2.

The amidation can be carried out by a conventionally known method. An example of such a conventionally known method is a method of allowing the compound of formula 12-2 to react with the corresponding amine in the presence of a condenser (see "*Peptide Gosei no Kiso to Jikken* (Base and Experiments of Peptide Synthesis)" (Nobuo IZUMIYA, et al., Maruzen, 1983)). Thus obtained compound of formula 13-2 can be isolated and purified by a known separation purification means, or it can be subjected to the subsequent step without such isolation and purification.

(Step 18)

This step is a method of deprotecting the protective group for the amino group of the compound of formula 12-2 or the compound of formula 13-2, so as to obtain the compound of formula 9-3. This step can be carried out by the same method as that in Step 7. Thus obtained compound of formula 9-3 can be isolated and purified by a known separation purification means, or it can be subjected to the subsequent step without such isolation and purification.

<Production Method E>

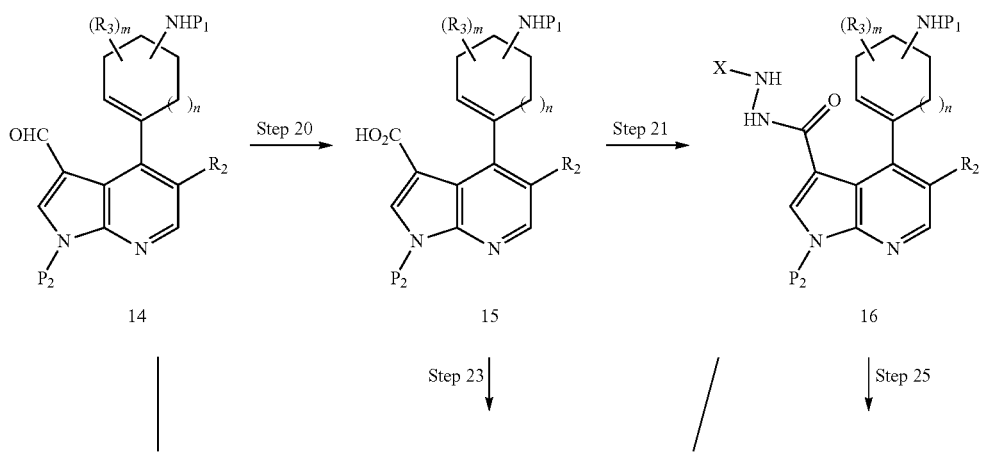

14

15

16

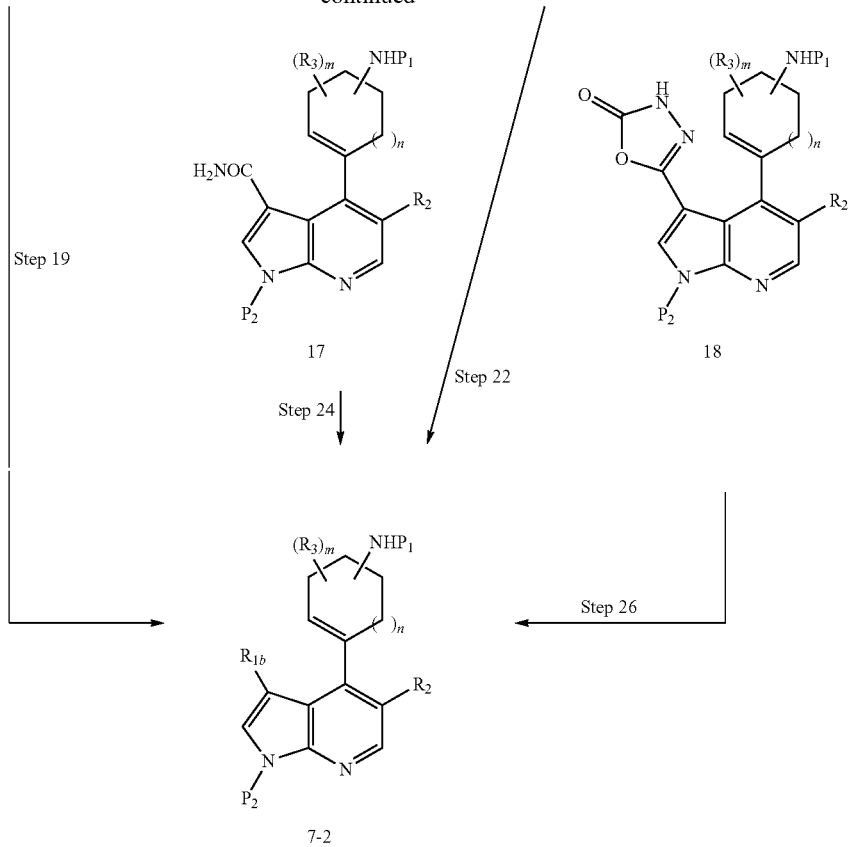

Production Method E is a method of inducing the compound of formula 14 having a formyl group as a substituent of azaindole to the compound of formula 7-2 having $R_1$ via conversion of the formyl group. $R_{1b}$ is an oxazol-5-yl group, a 4-methyl-5-oxo-4,5-dihydro-1,3,4-oxadiazol-2-yl group, a 1,3,4-oxadiazol-2-yl group, or a 1,2,4-oxadiazol-5-yl group, among substituents represented by $R_1$. The compound of formula 14 can be obtained from commercially available 4-chloro-1H-pyrrolo[2,3-b]pyridine-3-carbaldehyde or the like, via Step 2 and Step 4. Other symbols have the same meanings as those described above.

(Step 19)

This step is a method of allowing the compound of formula 14 to act on para-tolylsulfonylmethylisocyanide under basic conditions to construct an oxazole ring, so as to obtain the compound of formula 7-2.

The para-tolylsulfonylmethylisocyanide is used in an amount of generally from 1 to 100 moles, and preferably from about 1 to 10 moles, based on the amount of the compound of formula 14 (1 mole).

Either an organic base or an inorganic base can be used herein as a base. Examples of the organic base include alkyl amines such as dicyclohexylamine, diisopropylamine, diethylamine, triethylamine, tributylamine or diisopropylethylamine, alkyl anilines such as N,N-dimethylaniline, heterocyclic amines such as piperidine, pyrrolidine, 2,2,6,6-tetramethylpiperidine, morpholine, piperazine, imidazole, 1-ethylpiperidine, 4-methylmorpholine, 1-methylpyrrolidine, 1,4-diazabicyclo[2.2.2]octane or 1,8-diazabicyclo[5.4.0]-7-undecene, quaternary ammonium salts such as benzyltriethylammonium chloride or methyltrioctylammonium chloride, and diamines such as N,N,N',N'-tetramethylethylenediamine. Examples of the inorganic base include sodium hydroxide, potassium hydroxide, sodium carbonate, potassium carbonate, sodium hydrogen carbonate, and potassium hydrogen carbonate. The base is used in an amount of generally from 0.5 to 10 moles, and preferably from about 1 to 5 moles, based on the amount of the compound of formula 14 (1 mole).

The solvent used in the reaction is not particularly limited, as long as it does not adversely affect the reaction. Examples of the solvent used herein include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane and tetrahydrofuran), aprotic polar solvents (e.g., N,N-dimethylformamide, dimethyl sulfoxide, and hexamethylphosphoramide), and the mixtures thereof.

The reaction time is from 0.1 to 100 hours, and preferably from 0.5 to 24 hours. The reaction temperature is from 0° C. to the boiling point of the solvent, and preferably from 0° C. to 100° C.

Thus obtained compound of formula 7-2 can be isolated and purified by a known separation purification means, or it can be subjected to the subsequent step without such isolation and purification.

(Step 20)

This step is a method of subjecting the compound of formula 14 to an oxidation reaction to obtain the compound of formula 15.

The oxidation can be carried out by a generally known method, for example, the method described in "5th edition,

*Jikken Kagaku Koza* 17, *Yuki Kagobutsu no Gosei V, Sanka Hanno* (5th Edition, Experimental Chemistry Seminar 17, Synthesis of Organic Compounds V, Oxidation Reaction)," edited by the Chemical Society of Japan (2005), or a method equivalent thereto. In this reaction, Pinnick oxidation (for example, Tetrahedron 1981, 37, 2091) is preferably used.

Thus obtained compound of formula 15 can be isolated and purified by a known separation purification means, or it can be subjected to the subsequent step without such isolation and purification.

(Step 21)

This step is a method of subjecting the compound of formula 15 and hydrazines, which are commercially available products or can be produced by a known method, to a dehydration condensation reaction, so as to obtain the compound of formula 16. Examples of the hydrazines used in this step include hydrazine monohydrate and formyl hydrazine. This step can be carried out according to a known method by the use of a common condenser, so as to obtain the compound of formula 16.

This step can be carried out by the same method as that in Step 8.

Thus obtained compound of formula 16 can be isolated and purified by a known separation purification means, or it can be subjected to the subsequent step without such isolation and purification.

(Step 22)

This step is a method of converting the acyl hydrazide group of the compound of formula 16 to a 1,3,4-oxadiazole ring to obtain the compound of formula 7-2.

This step can be carried out according to generally known methods (for example, J. Med. Chem, Vol. 34, p. 2060, 1991, Tetrahedron Letters, vol. 49, p. 879, 2008, J. Med. Chem., vol. 52, p. 6270, 2009). The compound of formula 7-2 can be synthesized, for example, by allowing triethyl orthoformate, triethyl orthoacetate, triethyl orthopropionate, acid anhydride, acetyl chloride or the like to react with the compound of formula 16, and such a compound is used in an amount of generally from 1 to 100 moles, and preferably from about 1 to 10 moles, based on the amount of the compound of formula 16 (1 mole).

As necessary, Lewis acid, which includes mineral acids such as hydrochloric acid or hydrobromic acid and organic acids such as acetic acid, para-toluenesulfonic acid or trifluoromethanesulfonic acid, may be added. The acid is used in an amount of generally from 0.01 to 100 moles, and preferably from about 0.05 to 10 moles, based on the amount of Compound 16 (1 mole).

The solvent used in the reaction is not particularly limited, as long as it does not adversely affect the reaction. Examples of the solvent used herein include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane and tetrahydrofuran), aprotic polar solvents (e.g., N,N-dimethylformamide, dimethyl sulfoxide, and hexamethylphosphoramide), and the mixtures thereof. Thus obtained compound of formula 7-2 can be isolated and purified by a known separation purification means, or it can be subjected to the subsequent step without such isolation and purification.

(Step 23)

This step can be carried out by the same method as that in Step 14.

Thus obtained compound of formula 17 can be isolated and purified by a known separation purification means, or it can be subjected to the subsequent step without such isolation and purification.

(Step 24)

This step is a method of converting the amide group of the compound of formula 17 to a 1,2,4-oxadiazole ring, so as to obtain the compound of formula 7-2.

This step can be carried out by the same method as that in Step 22.

Thus obtained compound of formula 7-2 can be isolated and purified by a known separation purification means, or it can be subjected to the subsequent step without such isolation and purification.

(Step 25)

This step is a method of converting the acyl hydrazide group of the compound of formula 16 to a 1,3,4-oxadiazolone ring, so as to obtain the compound of formula 18. The compound of formula 18 can be synthesized, for example, by allowing carbonylimidazole, phosgene or the like to react with the compound of formula 16.

This step can be carried out by the same method as that in Step 22.

Thus obtained compound of formula 18 can be isolated and purified by a known separation purification means, or it can be subjected to the subsequent step without such isolation and purification.

(Step 26)

This step is a method of subjecting the compound of formula 18 to an alkylation reaction in the presence of a base to obtain the compound of formula 7-2.

The alkylation can be carried out by a conventionally known method.

Thus obtained compound of formula 7-2 can be isolated and purified by a known separation purification means, or it can be subjected to the subsequent step without such isolation and purification.

Thus obtained compound of formula 7-2 can be induced to the compound of the present invention of formula (I) in the same manner as the method of obtaining the compound of the present invention of formula (I) from the compound of formula 7 in Production Method A.

The compound of the present invention can easily be isolated and purified according to an ordinary separation means. Examples of such means include solvent extraction, recrystallization, preparatory reverse-phase high-performance liquid chromatography, column chromatography, and preparatory thin-layer chromatography.

When the compound of the present invention has isomers such as an optical isomer, a stereoisomer, a regioisomer, a rotational isomer or a tautomer, such isomers and the mixtures thereof are all included in the compound of the present invention. For example, when the compound of the present invention has an optical isomer, an optical isomer obtained as a result of resolution of a racemic mixture is also included in the compound of the present invention.

The compound of the present invention or a salt thereof may be a crystal. Even if the crystal form is a single form or a polymorphic mixture, the crystal is included in the compound of the present invention or a salt thereof. Such a crystal can be produced by crystallizing this compound according to a known crystallization method. The compound of the present invention or a salt thereof may be either a solvate (for example, a hydrate), or a non-solvate, and both of them are included in the compound of the present invention or a salt thereof. Compounds labeled with isotopes (for example, deuterium, $^3$H, $^{13}$C, $^{14}$C, $^{35}$S, and $^{125}$I) or the like are also included in the compound of the present invention or a salt thereof.

A prodrug of the compound of the present invention or a salt thereof means a compound, which is converted to the compound of the present invention or a salt thereof as a result of a reaction with enzyme, gastric acid or the like under in vivo physiological conditions; namely, a compound, which undergoes enzymatic oxidation, reduction, hydrolysis, etc., so that it is changed to the compound of the present invention or a salt thereof, or a compound, which undergoes hydrolysis or the like by the action of gastric acid or the like, so that it is changed to the compound of the present invention or a salt thereof. Moreover, such a prodrug of the compound of the present invention or a salt thereof may also be a compound, which changes to the compound of the present invention or a salt thereof under physiological conditions as described in "*Iyakuhin no Kaihatsu* (Development of Pharmaceutical Products)," Vol. 7, *Bunshi Sekkei* (Molecular Designing), pp. 163-198, published by Hirokawa Shoten, 1990.

A salt of the compound of the present invention is not particularly limited, as long as it is pharmaceutically acceptable, and it means a salt commonly used in the field of organic chemistry. Examples of such a salt include salts, such as a base-added salt in a carboxy group when the present compound has the carboxy group, or an acid-added salt in an amino group or a basic heterocyclic group when this compound has the amino group or the basic heterocyclic group.

Examples of the base-added salt include: alkaline metal salts such as a sodium salt or a potassium salt; alkaline-earth metal salts such as a calcium salt or a magnesium salt; ammonium salts; and organic amine salts such as a trimethylamine salt, a triethylamine salt, a dicyclohexylamine salt, an ethanolamine salt, a diethanolamine salt, a triethanolamine salt, a procaine salt, and an N,N'-dibenzylethylenediamine salt.

Examples of the acid-added salt include: inorganic acid salts such as a hydrochloride, a sulfate, a nitrate, a phosphate, or a perchlorate; organic acid salts such as an acetate, a formate, a maleate, a fumarate, a tartrate, a citrate, an ascorbate, or a trifluoroacetate; and sulfonates such as a methanesulfonate, an isethionate, a benzenesulfonate, or a p-toluenesulfonate.

The compound of the present invention or a salt thereof has a higher selective inhibitory activity on JAK3, than on JAK1 and JAK2. In addition, the compound of the present invention or a salt thereof has an excellent action to suppress the growth of human PBMC. Since the compound of the present invention or a salt thereof has an excellent JAK3-inhibitory activity, it is useful as a pharmaceutical agent for preventing or treating a disease involving JAK3. Moreover, since the compound of the present invention or a salt thereof has excellent selectivity to JAK3, it is useful as a pharmaceutical agent with reduced side effects, which are caused by JAK1 and JAK2 (i.e., lipid rise, anemia, neutropenia, immunosuppression, etc.). The "a disease involving JAK3" is a disease, the incidence of which is decreased and the symptoms of which achieve a remission, are alleviated, and/or are completely recovered by deleting, suppressing and/or inhibiting the function of JAK3. Examples of such a disease involving JAK3 include autoimmune disease (rheumatoid arthritis, systemic lupus erythematosus, scleroderma, polymyositis/dermatomyositis, Sjogren's syndrome, Behcet's disease, etc.), allergic disease (bronchial asthma, allergic rhinitis/hay fever, atopic dermatitis, food allergy, anaphylaxis, drug allergy, hives, conjunctivitis, etc.), nervous system disease (multiple sclerosis, Alzheimer's disease, etc.), inflammatory bowel disease (ulcerative colitis, Crohn's disease), psoriasis, contact dermatitis, diabetes, celiac disease, viral infectious disease, acute respiratory distress syndrome (ARDS), graft-versus-host disease (GVHD), transplant rejection, hematologic malignancy (lymphoma, leukemia), and other malignant tumors. Among these diseases, psoriasis, graft-versus-host disease, multiple sclerosis, inflammatory bowel disease, systemic lupus erythematosus and rheumatoid arthritis are preferable, and rheumatoid arthritis or multiple sclerosis is more preferable.

When the compound of the present invention or a salt thereof is used as a pharmaceutical agent, a pharmaceutical carrier can be mixed into the compound, as necessary, and various dosage forms can be adopted depending on prevention or treatment purposes. As such a dosage form, any one of an oral agent, an injection, a suppository, an ointment, an inhalant, a patch and the like may be adopted. Since the compound of the present invention or a salt thereof has excellent oral absorbability, an oral agent is preferably adopted. These dosage forms can be produced by commonly used formulation methods, which are known to a person skilled in the art.

As such pharmaceutical carriers, various types of organic or inorganic carrier substances, which are commonly used as preparation materials, are used. Such a carrier is mixed as an excipient, a binder, a disintegrator or a lubricant into a solid preparation, and is also mixed as a solvent, a solubilizer, a suspending agent, a tonicity agent, a buffer, a soothing agent and the like into a liquid preparation. In addition, preparation additives such as an antiseptic, an antioxidant, a coloring agent, a sweetener or a stabilizer can also be used, as necessary.

In preparing a solid preparation for oral use, an excipient, and as necessary, an excipient, a binder, a disintegrator, a lubricant, a coloring agent, a flavoring agent and the like are added to the compound of the present invention, and thereafter, a tablet, a coated tablet, a granule, a powder agent, a capsule, and the like can be produced by an ordinary method.

In preparing an injection, a pH adjuster, a buffer, a stabilizer, a tonicity agent, a local anesthetic and the like are added to the compound of the present invention, and thereafter, subcutaneous, intramuscular, and intravenous injections can be produced by an ordinary method.

The amount of the compound of the present invention to be mixed into each of the aforementioned dosage unit forms is not constant, and it depends on the symptoms of a patient to whom the compound is to be applied, or the dosage form or the like. In general, the compound of the present invention is desirably used at a dose of approximately from 0.05 to 1,000 mg per dosage unit form in the case of an oral agent, and at a dose of approximately from 0.01 to 500 mg in the case of injection, and at a dose of approximately from 1 to 1,000 mg in the case of a suppository.

The applied dose of a drug having the aforementioned dosage form varies depending on the symptoms, body weight, age, sex and the like of a patient, and it cannot be unconditionally determined. The compound of the present invention may be generally applied at a dose of approximately from 0.05 to 5,000 mg, and preferably from 0.1 to 1,000 mg, per adult (body weight: 50 kg) per day. This dose is preferably administered to a patient once a day, or divided over 2 or 3 administrations.

EXAMPLES

Hereinafter, the present invention will be described in detail in the following examples. However, these examples are not intended to limit the scope of the present invention. Various types of reagents used in the examples are commercially available products, unless otherwise specified. For silica gel chromatography, Biotage SNAP Cartridge Ultra manufactured by Biotage was used, and for basic silica gel chromatography, Biotage SNAP Cartridge KP-NH manufactured by Biotage was used.

For preparatory thin-layer chromatography, Kieselgel TM60F254, Art. 5744 manufactured by Merck, or NH2 Silica Gel 60F254 Plate Wako manufactured by Wako Pure Chemical Industries, Ltd. was used.

For $^1$H-NMR, AL400 (400 MHz) manufactured by JEOL, Mercury (400 MHz) manufactured by Varian, or Inova (400 MHz) manufactured by Varian was used, and the measurement was carried out by the use of tetramethylsilane as a standard substance. In addition, for mass spectrum, Micromass ZQ or SQD manufactured by Waters was used, and the measurement was carried out according to an electrospray ionization method (ESI) or an atmospheric pressure chemical ionization method (APCI). A microwave reaction was carried out by the use of Initiator manufactured by Biotage.

Abbreviations have the following meanings.
s: singlet
d: doublet
t: triplet
q: quartet
dd: double doublet
dt: double triplet
td: triple doublet
tt: triple triplet
ddd: double double doublet
ddt: double double triplet
dtd: double triple doublet
tdd: triple double doublet
m: multiplet
br: broad
Boc: tert-butoxycarbonyl
DMSO-d$_6$: deuterated dimethyl sulfoxide
CDCl$_3$: deuterated chloroform
THF: tetrahydrofuran
DMF: N,N-dimethylformamide
DMSO: dimethyl sulfoxide
TFA: trifluoroacetic acid
HATU: O-(7-azabenzotriazol-1-yl)-N,N,N',N'-tetramethyluronium hexafluorophosphate
HBTU: O-(benzotriazol-1-yl)-N,N,N',N'-tetramethyluronium hexafluorophosphate
Pd(PPh$_3$)$_4$: tetrakis(triphenylphosphine)palladium
PdCl$_2$(dppf)CH$_2$Cl$_2$: [1,1'-bis(diphenylphosphino)ferrocene]dichloropalladium(II) dichloromethane complex
PdCl$_2$(PPh$_3$)$_2$: dichlorobis(triphenylphosphine)palladium (II)

Reference Example 1

Reference Example 1(1a)

5-((tert-Butoxycarbonyl)amino)cyclohex-1-en-1-yl trifluoromethanesulfonate

Reference Example 1(1b)

3-((tert-Butoxycarbonyl)amino)cyclohex-1-en-1-yl trifluoromethanesulfonate

Tert-Butyl (3-oxocyclohexyl)carbamate (5.0 g) and N-phenyl-bis(trifluoromethanesulfonimide) (11.0 g) were dissolved in THF (100 mL), and the obtained solution was then cooled to −78° C. Thereafter, a THF solution (26.0 mL) of 2.0 M lithium diisopropylamide was added to the reaction solution, the temperature of the mixed solution was increased to 0° C., and the mixed solution was then stirred for 30 minutes. Thereafter, a 0.5 M aqueous solution of potassium hydrogen sulfate was added to the reaction mixture for dilution, and the obtained solution was then extracted with ethyl acetate. The gathered organic layer was washed with a saturated saline, dried over anhydrous sodium sulfate, and then concentrated under a reduced pressure. The obtained residue was purified by silica gel chromatography (hexane:ethyl acetate) to obtain each of the compound of Reference Example 1(1a) (4.39 g, yield: 54%), and the compound of Reference Example 1(1b) (2.00 g, yield: 25%).

Reference Example 1(1a): $^1$H NMR (CDCl$_3$) δ: 5.84-5.74 (m, 1H), 4.74-4.46 (m, 1H), 4.06-3.85 (m, 1H), 2.77-2.63 (m, 1H), 2.38-2.18 (m, 3H), 1.90-1.80 (m, 1H), 1.66-1.53 (m, 1H), 1.45 (s, 9H)
ESI-MS m/z 346 (MH$^+$)

Reference Example 1(1b): $^1$H NMR (CDCl$_3$) δ: 5.79-5.72 (m, 1H), 4.70-4.50 (m, 1H), 4.47-4.33 (m, 1H), 2.40-2.25 (m, 2H), 1.94-1.67 (m, 3H), 1.56-1.49 (m, 1H), 1.45 (s, 9H)
ESI-MS m/z 346 (MH$^+$)

Reference Example 1(2a)

tert-Butyl (3-(4,4,5,5-tetramethyl-1,3,2-dioxaborolan-2-yl)cyclohex-3-en-1-yl)carbamate DMF (90 mL) was added to the compound of Reference Example 1(1a) (9.25 g), 4,4,4',4',5,5,5',5'-octamethyl-2,2'-bi(1,3,2-dioxaborolane) (10.2 g) and potassium acetate (3.95 g), followed by nitrogen substitution. Thereafter, PdCl$_2$(dppf)CH$_2$Cl$_2$ (980 mg) was added to the resultant, and the obtained mixture was then stirred at 80° C. for 14 hours. Thereafter, the reaction mixture was cooled to a room temperature, and ethyl acetate and water were then added to the mixture. Thereafter, thus obtained mixture was filtered through Celite. The filtrate was extracted with ethyl acetate, and thereafter, the gathered organic layer was washed with water and then with a saturated saline. The resultant was dried over anhydrous sodium sulfate, and then concentrated under a reduced pressure. The obtained residue was purified by silica gel chromatography (hexane:ethyl acetate) to obtain a product of interest (6.51 g, yield: 75%).

$^1$H NMR (CDCl$_3$) δ: 6.56-6.51 (m, 1H), 4.58-4.41 (m, 1H), 3.80-3.62 (m, 1H), 2.58-2.41 (m, 1H), 2.31-2.13 (m, 2H), 1.98-1.77 (m, 2H), 1.54-1.47 (m, 1H), 1.44 (s, 9H), 1.25 (s, 12H)
ESI-MS m/z 324 (MH$^+$)

Reference Example 1(2b)

tert-Butyl (3-(4,4,5,5-tetramethyl-1,3,2-dioxaborolan-2-yl)cyclohex-2-en-1-yl)carbamate A product of interest was obtained in accordance with Reference Example 1(2a), with the exception that the compound of Reference Example 1(1b) was used instead of the compound of Reference Example 1(1a).

$^1$H NMR (CDCl$_3$) δ: 6.40-6.32 (m, 1H), 4.53 (d, J=7.3 Hz, 1H), 4.27-4.14 (m, 1H), 2.11-2.02 (m, 2H), 1.97-1.83 (m, 1H), 1.68-1.52 (m, 2H), 1.49-1.44 (m, 1H), 1.44 (s, 9H), 1.26 (s, 12H)
ESI-MS m/z 324 (MH$^+$)

Reference Example 2

Reference Example 2(1a)

4-((tert-Butoxycarbonyl)amino)cyclopent-1-en-1-yl trifluoromethanesulfonate

Reference Example 2(1b)

3-((tert-Butoxycarbonyl)amino)cyclopent-1-en-1-yl trifluoromethanesulfonate

Under a nitrogen atmosphere, a THF solution (114 mL) of 1.0 M lithium hexamethyldisilazide was added to THF (100 mL), and the obtained mixture was then cooled to −78° C. A THF (100 mL) solution of tert-butyl (3-oxocyclopentyl)carbamate (9.0 g) was added to the reaction solution over 10 minutes. Thereafter, N-phenyl-bis(trifluoromethanesulfonimide) (19.4 g) was added to the mixture, and the temperature of the obtained mixture was then increased to 0° C., followed by stirring for 10 minutes. Thereafter, water, toluene, and a 5 M aqueous solution of sodium hydroxide were added to the reaction mixture, and the obtained mixture was then stirred at a room temperature for 30 minutes. Thereafter, the reaction mixture was extracted with toluene. The gathered organic layer was successively washed with a 0.5 M aqueous solution of potassium hydrogen sulfate, a saturated sodium hydrogen carbonate aqueous solution and a saturated saline, and dried over anhydrous sodium sulfate, followed by vacuum concentration. The obtained residue was purified by silica gel chromatography (hexane:ethyl acetate) to obtain each of the compound of Reference Example 2(1a) (8.61 g, yield: 58%) and the compound of Reference Example 2(1b) (4.31 g, yield: 29%).

Reference Example 2(1a): $^1$H NMR (CDCl$_3$) δ: 5.62-5.56 (m, 1H), 4.87-4.67 (m, 1H), 4.49-4.23 (m, 1H), 3.07-2.76 (m, 2H), 2.50-2.40 (m, 1H), 2.32-2.20 (m, 1H), 1.45 (s, 9H)

ESI-MS m/z 332 (MH$^+$)

Reference Example 2(1b): $^1$H NMR (CDCl$_3$) δ: 5.68-5.61 (m, 1H), 4.89-4.70 (m, 1H), 4.69-4.48 (m, 1H), 2.75-2.43 (m, 3H), 1.84-1.66 (m, 1H), 1.45 (s, 9H)

ESI-MS m/z 332 (MH$^+$)

Reference Example 2(2a)

tert-Butyl (3-(4,4,5,5-tetramethyl-1,3,2-dioxaborolan-2-yl)cyclopent-3-en-1-yl)carbamate A product of interest was obtained in accordance with Reference Example 1(2a), with the exception that the compound of Reference Example 2(1a) was used instead of the compound of Reference Example 1(1a).

$^1$H NMR (CDCl$_3$) δ: 6.50-6.45 (m, 1H), 4.76-4.58 (m, 1H), 4.37-4.19 (m, 1H), 2.86-2.70 (m, 2H), 2.37-2.22 (m, 2H), 1.43 (s, 9H), 1.27 (s, 12H)

ESI-MS m/z 310 (MH$^+$)

Reference Example 2(2b)

tert-Butyl (3-(4,4,5,5-tetramethyl-1,3,2-dioxaborolan-2-yl)cyclopent-2-en-1-yl)carbamate A product of interest was obtained in accordance with Reference Example 1(2a), with the exception that the compound of Reference Example 2(1b) was used instead of the compound of Reference Example 1(1a).

$^1$H NMR (CDCl$_3$) δ: 6.42-6.32 (m, 1H), 4.84-4.69 (m, 1H), 4.58-4.39 (m, 1H), 2.58-2.46 (m, 1H), 2.44-2.25 (m, 2H), 1.55-1.47 (m, 1H), 1.44 (s, 9H), 1.27 (s, 12H)

ESI-MS m/z 310 (MH$^+$)

Reference Example 3

Reference Example 3(1)

tert-Butyl ((1S,3R)-3-hydroxycyclohexyl)carbamate (1R,3S)-3-Aminocyclohexanol (13.7 g) was dissolved in 2-methyltetrahydrofuran (140 mL), and a saturated aqueous solution of sodium hydrogen carbonate (70 mL) was then added to the obtained solution. Thereafter, di-tert-butyl dicarbonate (27.5 g) was added to the reaction mixture at 0° C., and the obtained mixture was then stirred at a room temperature for 16 hours. Thereafter, water was added to the reaction mixture for dilution, and the obtained mixture was then extracted with 2-methyltetrahydrofuran. The gathered organic layer was washed with a saturated aqueous solution of ammonium chloride, with a saturated aqueous solution of sodium hydrogen carbonate and with a saturated saline, and dried over anhydrous sodium sulfate, followed by vacuum concentration. The obtained solid was washed with heptane to obtain a product of interest (22.7 g, yield: 89%).

$^1$H NMR (CDCl$_3$) δ: 4.82-4.58 (m, 1H), 3.82-3.66 (m, 1H), 3.63-3.40 (m, 1H), 2.25-2.11 (m, 1H), 1.93-1.74 (m, 3H), 1.62-1.55 (m, 1H), 1.44 (s, 9H), 1.39-1.04 (m, 4H)

ESI-MS m/z 216 (MH$^+$)

Reference Example 3(2)

(S)-tert-Butyl (3-oxocyclohexyl)carbamate

The compound of Reference Example 3(1) (21.5 g) was dissolved in ethyl acetate (200 mL), and thereafter, 1-methyl-2-azaadamantane N-oxyl (166 mg), a 5 M aqueous solution of sodium bromide (6 mL) and a saturated aqueous solution of sodium hydrogen carbonate (100 mL) were successively added to the above obtained solution. Thereafter, a 10% aqueous solution of sodium hypochlorite (100 mL) was added to the mixed solution at 0° C., and the obtained mixture was then stirred for 1 hour. Thereafter, a 10% aqueous solution of sodium hydrogen sulfite was added to the reaction mixture at 0° C., and the obtained mixture was diluted with a 10% aqueous solution of potassium carbonate and was then extracted with ethyl acetate. The gathered organic layer was washed with 1 M hydrochloric acid, with a saturated aqueous solution sodium hydrogen carbonate, with water and with a saturated saline, and dried over anhydrous sodium sulfate, followed by vacuum concentration. The obtained solid was washed with diisopropyl ether-heptane to obtain a product of interest (19.4 g, yield: 91%).

$^1$H NMR (CDCl$_3$) δ: 4.67-4.35 (m, 1H), 4.05-3.77 (m, 1H), 2.76-2.64 (m, 1H), 2.43-2.19 (m, 3H), 2.14-1.92 (m, 2H), 1.79-1.64 (m, 2H), 1.44 (s, 9H)

ESI-MS m/z 214 (MH$^+$)

Reference Example 3(3)

(S)-5-((tert-Butoxycarbonyl)amino)cyclohex-1-en-1-yl trifluoromethanesulfonate

A THF (160 mL) solution of the compound of Reference Example 3(2) (32.3 g) was added dropwise to a THF solution (780 mL) of sodium bis(trimethylsilyl)amide (60.5 g), which had been cooled to −78° C., and the reaction mixture was then stirred for 30 minute. N-phenyl-bis(trifluoromethanesulfonimide) (64.3 g) was added to the reaction mixture at −78° C., and the obtained mixture was then stirred for 30 minutes. Thereafter, the temperature of the reaction mixture was increased to 0° C., and the mixture was further stirred for 2 hours. Thereafter, water and a 1 M aqueous solution of sodium hydroxide were added to the reaction mixture, the temperature of the obtained mixture was then increased to a room temperature, and the mixture was then extracted with toluene. The gathered organic layer was washed with a 1 M aqueous solution of potassium hydrogen sulfate, with a saturated aqueous solution of sodium hydrogen carbonate, with water and with a saturated saline, and dried over anhydrous sodium sulfate, followed by vacuum concentration. Heptane was added to the obtained residue, and the precipitated solid was collected by filtration and was then washed with heptane to obtain a product of interest (41.6 g, yield: 79%).

$^1$H NMR (CDCl$_3$) δ: 5.84-5.74 (m, 1H), 4.74-4.46 (m, 1H), 4.06-3.85 (m, 1H), 2.77-2.63 (m, 1H), 2.38-2.18 (m, 3H), 1.90-1.80 (m, 1H), 1.66-1.53 (m, 1H), 1.45 (s, 9H)

ESI-MS m/z 346 (MH$^+$)

Reference Example 3(4)

(S)-tert-Butyl (3-(4,4,5,5-tetramethyl-1,3,2-dioxaborolan-2-yl)cyclohex-3-en-1-yl)carbamate To a toluene (450 mL) solution of the compound of Reference Example 3(3) (32.8 g), bis(pinacolato)diboron (26.5 g), potassium acetate (28.0 g), triphenylphosphine (2.49 g) and PdCl2(PPh3)2 (3.33 g) were successively added. The temperature of the obtained mixture was increased to 60° C., and the mixture was then stirred under a nitrogen atmosphere for 4 hours. Thereafter, the reaction mixture was cooled to a room temperature, toluene was then added to the mixture, and thereafter thus obtained mixture was filtered through Celite. The filtrate was washed with a 1 M aqueous solution of sodium hydroxide, with 1 M hydrochloric acid, with a saturated aqueous solution of sodium hydrogen carbonate, with water and with a saturated saline, and dried over anhydrous sodium sulfate, followed by vacuum concentration. Ethyl acetate-heptane and activated carbon were added to the obtained residue, and the obtained mixture was left for 1 hour and was then filtered through Celite. The filtrate was concentrated under a reduced pressure, and cyclohexane-heptane was then added to the obtained residue. The precipitated solid was collected by filtration and was then washed with cyclohexane-heptane to obtain a product of interest (21.3 g, yield: 69%).

$^1$H NMR (CDCl$_3$) δ: 6.56-6.51 (m, 1H), 4.58-4.41 (m, 1H), 3.80-3.62 (m, 1H), 2.58-2.41 (m, 1H), 2.31-2.13 (m, 2H), 1.98-1.77 (m, 2H), 1.54-1.47 (m, 1H), 1.44 (s, 9H), 1.25 (s, 12H)

ESI-MS m/z 324 (MH$^+$)

TABLE 1

| | Structural formula |
|---|---|
| Reference Example 1(2a) | (cyclohexene with NHBoc and pinacol boronate) |
| Reference Example 1(2b) | (cyclohexene with NHBoc and pinacol boronate) |
| Reference Example 2(2a) | (cyclopentene with NHBoc and pinacol boronate) |
| Reference Example 2(2b) | (cyclopentene with NHBoc and pinacol boronate) |
| Reference Example 3 | (cyclohexene with NHBoc (wedge) and pinacol boronate) |

Example 1

Example 1(1)

tert-Butyl (3-(3-iodo-1-tosyl-1H-pyrrolo[2,3-b]pyridin-4-yl)cyclohex-3-en-1-yl)carbamate (Compound 1(1))

To 4-bromo-1H-pyrrolo[2,3-b]pyridine (2.00 g), the compound of Reference Example 1(2a) (4.60 g) and tripotassium phosphate (5.41 g), 1,4-dioxane (20 mL) and water (3.3 mL)

were added, followed by nitrogen substitution, and PdCl₂(dppf)CH₂Cl₂ (746 mg) was then added to the reaction mixture. Thus obtained mixture was stirred at 100° C. for 5 hours. Thereafter, the reaction mixture was cooled to a room temperature, and ethyl acetate and water were then added to the mixture. Thereafter, thus obtained mixture was filtered through Celite. The filtrate was then extracted with ethyl acetate, and the gathered organic layer was then washed with water and then with a saturated saline. The resultant was dried over anhydrous sodium sulfate, and then concentrated under a reduced pressure. The obtained residue was purified by silica gel chromatography (chloroform:methanol) to obtain a corresponding coupling product. The obtained coupling product was subjected to the subsequent reaction without further purification.

DMF (30 mL) was added to the obtained coupling product, and the obtained mixture was then cooled to 0° C. Subsequently, N-iodosuccinimide (2.52 g) was added to the mixture, and the obtained mixture was then stirred at 0° C. for 30 minutes. Thereafter, a 0.5 M aqueous solution of sodium hydrogen sulfite was added to the reaction mixture, and the obtained mixture was then extracted with ethyl acetate. The gathered organic layer was washed with water and then with a saturated saline. The resultant was dried over anhydrous sodium sulfate, and then concentrated under a reduced pressure. The obtained residue was purified by silica gel chromatography (chloroform:methanol) to obtain a corresponding iodine product. The obtained iodine product was subjected to the subsequent reaction without further purification.

DMF (30 mL) was added to the obtained iodine product, and the obtained mixture was then cooled to 0° C. Thereafter, 60% sodium hydride (1.02 g), and then, para-toluenesulfonyl chloride (2.33 g) were added to the reaction mixture, and the obtained mixture was then stirred at 0° C. for 30 minutes. Thereafter, ice water was added to the reaction mixture, and the water layer was then extracted with ethyl acetate. The gathered organic layer was washed with water and then with a saturated saline. The resultant was dried over anhydrous sodium sulfate, and then concentrated under a reduced pressure. The obtained residue was purified by silica gel chromatography (hexane:ethyl acetate) to obtain a product of interest (3.49 g, yield: 58%).

¹H NMR (CDCl₃) δ: 8.35 (d, J=4.9 Hz, 1H), 8.10 (d, J=8.5 Hz, 2H), 7.89 (s, 1H), 7.30 (d, J=8.5 Hz, 2H), 6.94 (d, J=4.9 Hz, 1H), 5.72-5.67 (m, 1H), 4.75-4.59 (m, 1H), 4.11-3.97 (m, 1H), 2.70-2.60 (m, 1H), 2.40-2.32 (m, 2H), 2.39 (s, 3H), 2.22-2.09 (m, 1H), 2.04-1.94 (m, 1H), 1.75-1.62 (m, 1H), 1.44 (s, 9H)

ESI-MS m/z 594 (MH⁺)

Example 1(2)

N-(3-(3-Phenyl-1H-pyrrolo[2,3-b]pyridin-4-yl)cyclohex-3-en-1-yl)acrylamide (Compound 1)

To Compound 1(1) (100 mg), phenylboronic acid (31.0 mg) and tripotassium phosphate (89.2 mg), 1,4-dioxane (1.8 mL) and water (0.3 mL) were added, followed by nitrogen substitution. Thereafter, PdCl₂(dppf)CH₂Cl₂ (12.3 mg) was added to the reaction mixture, and the obtained mixture was then stirred at 100° C. for 2 hours. Thereafter, the reaction mixture was cooled to a room temperature, and ethyl acetate and water were then added to the mixture. Thereafter, thus obtained mixture was filtered through Celite. The filtrate was extracted with ethyl acetate, and the gathered organic layer was washed with water and then with a saturated saline. The resultant was dried over anhydrous sodium sulfate, and then concentrated under a reduced pressure.

THF (1.0 mL) and a THF solution (1.0 mL) of 1.0 M tetrabutylammonium fluoride were added to the obtained residue, and the obtained mixture was then stirred at a room temperature for 4 hours. Thereafter, the reaction mixture was concentrated under a reduced pressure, and was then purified by silica gel chromatography (chloroform:methanol) to obtain a corresponding coupling product. The obtained coupling product was subjected to the subsequent reaction without further purification.

Methanol (1 mL) and a 1,4-dioxane solution (1 mL) of 4 M hydrochloric acid were added to the obtained coupling product, and the obtained mixture was then stirred at a room temperature for 30 minutes. Thereafter, the reaction mixture was concentrated under a reduced pressure. Under a nitrogen atmosphere, dichloromethane (2 mL) and diisopropylethylamine (0.2 mL) were added to the reaction mixture, and the obtained mixture was then cooled to 0° C. Thereafter, acryloyl chloride (0.02 mL) was added to the reaction mixture, and the obtained mixture was then stirred for 30 minutes. Thereafter, an aqueous ammonia solution, chloroform and methanol were successively added to the reaction mixture, and thus obtained mixture was then stirred at a room temperature for 1 hour. Thereafter, the reaction mixture was extracted with chloroform, and the gathered organic layer was washed with a saturated saline, dried over anhydrous sodium sulfate, and then concentrated under a reduced pressure. The obtained residue was purified by silica gel chromatography (chloroform:methanol) to obtain the title compound (38.1 mg, yield: 66%).

¹H NMR (CDCl₃-CD₃OD) δ: 8.19 (d, J=5.1 Hz, 1H), 7.46-7.23 (m, 6H), 6.93 (d, J=5.1 Hz, 1H), 6.30-6.20 (m, 1H), 6.11 (dd, J=10.2, 16.8 Hz, 1H), 5.69-5.58 (m, 1H), 5.54-5.41 (m, 1H), 4.14-3.92 (m, 1H), 2.60-2.45 (m, 1H), 2.12-1.98 (m, 1H), 1.96-1.66 (m, 3H), 1.49-1.31 (m, 1H)

ESI-MS m/z 344 (MH⁺)

Example 2

N-(3-(3-(Pyridin-4-yl)-1H-pyrrolo[2,3-b]pyridin-4-yl)cyclohex-3-en-1-yl)acrylamide (Compound 2)

The title compound was obtained in accordance with Example 1(2), with the exception that 4-(4,4,5,5-tetramethyl-1,3,2-dioxaborolan-2-yl)pyridine was used instead of the phenylboronic acid.

¹H NMR (CDCl₃-CD₃OD) δ: 8.60-8.41 (m, 2H), 8.34-8.16 (m, 1H), 7.57-7.42 (m, 1H), 7.38-7.27 (m, 2H), 7.06-6.94 (m, 1H), 6.36-6.08 (m, 2H), 5.72-5.58 (m, 1H), 5.55-5.36 (m, 1H), 4.22-4.00 (m, 1H), 2.78-2.60 (m, 1H), 2.22-1.75 (m, 4H), 1.58-1.37 (m, 1H)

ESI-MS m/z 345 (MH⁺)

Example 3

N-(3-(3-(1H-Pyrazol-4-yl)-1H-pyrrolo[2,3-b]pyridin-4-yl)cyclohex-3-en-1-yl)acrylamide (Compound 3)

The title compound was obtained in accordance with Example 1(2), with the exception that tert-butyl 4-(4,4,5,5-tetramethyl-1,3,2-dioxaborolan-2-yl)-1H-pyrazole-1-carboxylate was used instead of the phenylboronic acid.

¹H NMR (DMSO-d₆) δ: 12.73 (br. s., 1H), 11.74 (d, J=1.8 Hz, 1H), 8.16 (d, J=4.8 Hz, 1H), 7.97 (d, J=7.3 Hz, 1H), 7.62 (br. s., 1H), 7.46-7.42 (m, 2H), 6.86 (d, J=4.8 Hz, 1H), 6.23

(dd, J=10.2, 17.2 Hz, 1H), 6.06 (dd, J=2.4, 17.2 Hz, 1H), 5.56 (dd, J=2.4, 10.2 Hz, 1H), 5.40 (br. s., 1H), 3.91-3.77 (m, 1H), 2.42 (dd, J=4.6, 16.7 Hz, 1H), 2.22-1.94 (m, 3H), 1.84-1.72 (m, 1H), 1.50-1.35 (m, 1H)

ESI-MS m/z 334 (MH$^+$)

Example 4

N-(3-(3-(Pyridin-3-yl)-1H-pyrrolo[2,3-b]pyridin-4-yl)cyclohex-3-en-1-yl)acrylamide (Compound 4)

The title compound was obtained in accordance with Example 1(2), with the exception that pyridin-3-ylboronic acid was used instead of the phenylboronic acid.

$^1$H NMR (DMSO-d$_6$) δ: 12.06 (br. s., 1H), 8.52 (d, J=1.8 Hz, 1H), 8.46 (dd, J=1.8, 4.8 Hz, 1H), 8.24 (d, J=4.8 Hz, 1H), 8.01 (d, J=7.3 Hz, 1H), 7.71-7.66 (m, 2H), 7.37 (dd, J=4.8, 7.3 Hz, 1H), 6.96 (d, J=4.8 Hz, 1H), 6.24 (dd, J=10.1, 17.0 Hz, 1H), 6.08 (dd, J=2.4, 17.0 Hz, 1H), 5.57 (dd, J=3.7, 10.1 Hz, 1H), 5.18 (br.s., 1H), 3.89-3.76 (m, 1H), 2.58-2.53 (m, 1H), 2.21 (ddd, J=2.6, 9.2, 16.9 Hz, 1H), 1.80-1.65 (m, 3H), 1.44-1.28 (m, 1H)

ESI-MS m/z 345 (MH$^+$)

Example 5

N-(3-(3-(6-(Hydroxymethyl) pyridin-3-yl)-1H-pyrrolo[2,3-b]pyridin-4-yl)cyclohex-3-en-1-yl)acrylamide (Compound 5)

The title compound was obtained in accordance with Example 1(2), with the exception that (6-(hydroxymethyl) pyridin-3-yl)boronic acid was used instead of the phenylboronic acid.

$^1$H NMR (CDCl$_3$) δ: 8.49 (s, 1H), 8.28 (d, J=4.8 Hz, 1H), 7.70 (dd, J=2.2, 7.7 Hz, 1H), 7.46 (d, J=7.7 Hz, 1H), 7.39 (s, 1H), 6.92 (d, J=4.8 Hz, 1H), 6.27 (dd, J=1.6, 16.9 Hz, 1H), 6.09 (dd, J=10.3, 16.9 Hz, 1H), 5.93-5.83 (m, 1H), 5.62 (dd, J=1.6, 10.3 Hz, 1H), 5.58 (br. s., 1H), 4.87-4.78 (m, 2H), 3.80-3.69 (m, 2H), 2.32 (dd, J=3.7, 16.9 Hz, 1H), 2.21-2.08 (m, 1H), 2.03-1.75 (m, 4H)

ESI-MS m/z 375 (MH$^+$)

Example 6

N-(3-(3-(2-Methoxypyridin-3-yl)-1H-pyrrolo[2,3-b]pyridin-4-yl)cyclohex-3-en-1-yl)acrylamide (Compound 6)

The title compound was obtained in accordance with Example 1(2), with the exception that (2-methoxypyridin-3-yl)boronic acid was used instead of the phenylboronic acid.

$^1$H NMR (DMSO-d$_6$) δ: 11.83 (d, J=2.2 Hz, 1H), 8.18 (d, J=5.1 Hz, 1H), 8.11 (dd, J=1.8, 4.8 Hz, 1H), 8.06 (d, J=7.7 Hz, 1H), 7.60 (dd, J=1.8, 7.0 Hz, 1H), 7.45 (d, J=2.2 Hz, 1H), 7.01 (dd, J=5.1, 7.0 Hz, 1H), 6.90 (d, J=5.1 Hz, 1H), 6.24 (dd, J=10.3, 17.2 Hz, 1H), 6.09 (dd, J=2.6, 17.2 Hz, 1H), 5.58 (dd, J=2.6, 10.3 Hz, 1H), 5.08 (br. s., 1H), 3.76 (s, 3H), 2.55-2.48 (m, 1H), 2.31-2.14 (m, 1H), 1.72-1.44 (m, 3H), 1.39-1.14 (m, 1H)

ESI-MS m/z 375 (MH$^+$)

Example 7

N-(3-(3-(4-Methoxypyridin-3-yl)-1H-pyrrolo[2,3-b]pyridin-4-yl)cyclohex-3-en-1-yl)acrylamide (Compound 7)

The title compound was obtained in accordance with Example 1(2), with the exception that 4-methoxy-3-(4,4,5,5-tetramethyl-1,3,2-dioxaborolan-2-yl)pyridine was used instead of the phenylboronic acid.

$^1$H NMR (DMSO-d$_6$) δ: 11.86 (d, J=2.2 Hz, 1H), 8.41 (d, J=5.5 Hz, 1H), 8.29 (s, 1H), 8.18 (d, J=5.1 Hz, 1H), 8.07 (d, J=7.7 Hz, 1H), 7.46 (d, J=2.2 Hz, 1H), 7.04 (d, J=5.5 Hz, 1H), 6.90 (d, J=5.1 Hz, 1H), 6.24 (dd, J=9.9, 16.9 Hz, 1H), 6.09 (dd, J=2.2, 16.9 Hz, 1H), 5.58 (dd, J=2.2, 9.9 Hz, 1H), 5.08 (br. s., 1H), 3.75 (s, 3H), 2.55-2.48 (m, 1H), 2.29-2.16 (m, 1H), 1.71-1.48 (m, 3H), 1.36-1.17 (m, 1H)

ESI-MS m/z 375 (MH$^+$)

Example 8

N-(3-(3-(2-Hydroxypyridin-3-yl)-1H-pyrrolo[2,3-b]pyridin-4-yl)cyclohex-3-en-1-yl)acrylamide (Compound 8)

The title compound was obtained in accordance with Example 1(2), with the exception that (2-hydroxypyridin-3-yl)boronic acid was used instead of the phenylboronic acid.

$^1$H NMR (DMSO-d$_6$) δ: 11.74 (d, J=2.2 Hz, 1H), 11.47 (br. s., 1H), 8.16 (d, J=5.1 Hz, 1H), 8.06 (d, J=7.3 Hz, 1H), 7.50 (d, J=2.2 Hz, 1H), 7.31 (d, J=6.6 Hz, 2H), 6.88 (d, J=5.1 Hz, 1H), 6.30 (dd, J=9.9, 17.6 Hz, 1H), 6.21 (t, J=6.6 Hz, 1H), 6.09 (dd, J=2.2, 17.6 Hz, 1H), 5.57 (dd, J=2.2, 9.9 Hz, 1H), 5.30 (br. s., 1H), 3.93 (br. s., 1H), 2.70-2.56 (m, 1H), 2.38-2.24 (m, 1H), 1.96-1.68 (m, 3H), 1.52-1.33 (m, 1H)

ESI-MS m/z 361 (MH$^+$)

Example 9

N-(3-(3-(5-Formylfuran-2-yl)-1H-pyrrolo[2,3-b]pyridin-4-yl)cyclohex-3-en-1-yl)acrylamide (Compound 9)

The title compound was obtained in accordance with Example 1(2), with the exception that (5-formylfuran-2-yl)boronic acid was used instead of the phenylboronic acid.

$^1$H NMR (CDCl$_3$) δ: 10.96 (br. s., 1H), 9.55 (s, 1H), 8.33 (d, J=5.1 Hz, 1H), 7.73 (s, 1H), 7.36 (d, J=3.7 Hz, 1H), 7.02 (d, J=5.1 Hz, 1H), 6.59 (d, J=3.7 Hz, 1H), 6.36-6.14 (m, 3H), 5.64 (dd, J=1.8, 9.9 Hz, 1H), 5.59 (br. s., 1H), 4.40 (br. s., 1H), 2.85-2.76 (m, 1H), 2.53-2.38 (m, 1H), 2.30-2.14 (m, 1H), 2.10-1.99 (m, 1H), 1.97-1.85 (m, 1H), 1.62-1.40 (m, 1H)

ESI-MS m/z 362 (MH$^+$)

Example 10

N-(3-(3-(5-(Hydroxymethyl) furan-2-yl)-1H-pyrrolo[2,3-b]pyridin-4-yl)cyclohex-3-en-1-yl)acrylamide (Compound 10)

Methanol (1 mL) was added to the Compound 9 (15 mg), and the obtained mixture was then cooled to 0° C. Thereafter, sodium borohydride (2 mg) was added to the reaction mixture, and the obtained mixture was then stirred for 5 minutes. Thereafter, a saturated saline was added to the reaction mixture, and the obtained mixture was then extracted with chloroform. The extract was dried over anhydrous sodium sulfate, and then concentrated under a reduced pressure. The obtained residue was purified by silica gel chromatography (methanol:chloroform) to obtain the title compound (13 mg, yield: 87%).

$^1$H NMR (CDCl$_3$) δ: 10.19 (br. s., 1H), 8.28-8.22 (m, 1H), 7.52-7.35 (m, 1H), 6.90-6.86 (m, 1H), 6.37 (t, J=2.9 Hz, 1H), 6.32-6.21 (m, 2H), 6.09-6.01 (m, 1H), 5.75 (br. s., 2H), 5.70-5.55 (m, 1H), 4.68-4.66 (m, 2H), 4.22-4.11 (m, 1H), 2.52-2.44 (m, 1H), 2.30-2.24 (m, 1H), 2.06-1.80 (m, 3H), 1.53-1.43 (m, 1H)

ESI-MS m/z 364 (MH$^+$)

Example 11

N-(3-(3-(5-(Hydroxymethyl) pyridin-3-yl)-1H-pyrrolo[2,3-b]pyridin-4-yl)cyclohex-3-en-1-yl)acrylamide (Compound 11)

A compound was obtained in accordance with Example 1(2), with the exception that (5-formylpyridin-3-yl)boronic acid was used instead of the phenylboronic acid. Subsequently, the title compound was obtained in accordance with Example 10, with the exception that the above obtained compound was used instead of the Compound 9.

$^1$H NMR (DMSO-d$_6$) δ: 12.03 (s, 1H), 8.40 (d, J=2.2 Hz, 1H), 8.38 (d, J=2.2 Hz, 1H), 8.22 (d, J=5.1 Hz, 1H), 8.01 (d, J=7.3 Hz, 1H), 7.65 (d, J=2.6 Hz, 1H), 7.59 (t, J=2.0 Hz, 1H), 6.94 (d, J=5.1 Hz, 1H), 6.21 (dd, J=9.9, 16.9 Hz, 1H), 6.06 (dd, J=2.2, 16.9 Hz, 1H), 5.55 (dd, J=2.2, 9.9 Hz, 1H), 5.32 (t, J=5.5 Hz, 1H), 5.22 (br. s., 1H), 4.58 (d, J=5.5 Hz, 2H), 3.85-3.68 (m, 1H), 2.46-2.40 (m, 1H), 2.16 (ddd, J=2.4, 9.3, 16.9 Hz, 1H), 1.82-1.63 (m, 3H), 1.40-1.26 (m, 1H)

ESI-MS m/z 375 (MH$^+$)

Example 12

N-(3-(3-(Furan-2-yl)-1H-pyrrolo[2,3-b]pyridin-4-yl)cyclohex-3-en-1-yl)acrylamide (Compound 12)

DMF (1.0 mL) was added to Compound 1(1) (100 mg) and tributyl(furan-2-yl)stannane (90 mg), followed by nitrogen substitution. Thereafter, PdCl$_2$(PPh$_3$)$_2$ (12.0 mg) was added to the reaction mixture, and the obtained mixture was then stirred under heating at 100° C. for 2 hours. Thereafter, a saturated aqueous solution of sodium hydrogen carbonate and ethyl acetate were added to the reaction mixture, and the obtained mixture was stirred and was then filtered through Celite. The filtrate was extracted with ethyl acetate, and the gathered organic layer was washed with a saturated saline, dried over anhydrous sodium sulfate, and then concentrated under a reduced pressure.

The obtained residue was dissolved in THF (1 mL), a THF solution (1 mL) of 1.0 M tetrabutylammonium fluoride was then added to the obtained solution. Thus obtained mixture was stirred at a room temperature for 5 hours. Thereafter, a 0.067 M phosphate buffer (pH 7.4) was added to the reaction mixture, and the obtained mixture was then extracted with ethyl acetate. The gathered organic layer was washed with a saturated saline, dried over anhydrous sodium sulfate, and then concentrated under a reduced pressure. The obtained residue was purified by silica gel chromatography (hexane:ethyl acetate) to obtain a corresponding coupling product.

The obtained coupling product was subjected to the subsequent reaction without further purification.

Methanol (1 mL) and a 1,4-dioxane solution (1 mL) of 4 M hydrochloric acid were added to the obtained coupling product, and the obtained mixture was then stirred at a room temperature for 30 minutes. Thereafter, the reaction mixture was concentrated under a reduced pressure. Under a nitrogen atmosphere, dichloromethane (2 mL) and diisopropylethylamine (0.2 mL) were added to the reaction mixture, and the obtained mixture was then cooled to 0° C. Thereafter, acryloyl chloride (0.02 mL) was added to the reaction mixture, and the obtained mixture was then stirred for 30 minutes. Thereafter, an aqueous ammonia solution, chloroform and methanol were successively added to the reaction mixture, and thus obtained mixture was then stirred at a room temperature for 1 hour. Thereafter, the reaction mixture was extracted with chloroform, and the gathered organic layer was washed with a saturated saline, dried over anhydrous sodium sulfate, and concentrated under a reduced pressure. The obtained residue was purified by silica gel chromatography (chloroform:methanol) to obtain the title compound (40.3 mg, yield: 72%).

$^1$H NMR (CDCl$_3$-CD$_3$OD) δ: 8.23-8.15 (m, 1H), 7.54-7.42 (m, 2H), 6.99-6.88 (m, 1H), 6.49-6.42 (m, 1H), 6.39-6.22 (m, 2H), 6.22-6.05 (m, 1H), 5.69-5.56 (m, 2H), 4.35-4.15 (m, 1H), 2.74-2.59 (m, 1H), 2.16 (d, J=9.3 Hz, 3H), 1.96-1.81 (m, 1H), 1.69-1.52 (m, 1H)

ESI-MS m/z 334 (MH$^+$)

Example 13

N-(3-(3-(Thiazol-5-yl)-1H-pyrrolo[2,3-b]pyridin-4-yl)cyclohex-3-en-1-yl)acrylamide (Compound 13)

The title compound was obtained in accordance with Example 12, with the exception that 5-(tributylstannyl)thiazole was used instead of the tributyl(furan-2-yl)stannane.

$^1$H NMR (CDCl$_3$-CD$_3$OD) δ: 8.82 (s, 1H), 8.23 (d, J=5.1 Hz, 1H), 7.70 (s, 1H), 7.46 (s, 1H), 6.97 (d, J=5.1 Hz, 1H), 6.28-6.12 (m, 2H), 5.68-5.62 (m, 1H), 5.56-5.49 (m, 1H), 4.20-4.05 (m, 1H), 2.71-2.58 (m, 1H), 2.14-1.78 (m, 3H), 1.52-1.38 (m, 1H), 1.35-1.19 (m, 1H)

ESI-MS m/z 351 (MH$^+$)

Example 14

Example 14(1)

tert-Butyl (3-(3-(4-formylfuran-2-yl)-1-tosyl-1H-pyrrolo[2,3-b]pyridin-4-yl)cyclohex-3-en-1-yl)carbamate (Compound 14(1))

1,4-Dioxane (5.4 mL) and water (0.9 mL) were added to the Compound 1(1) (300 mg), (4-formylfuran-2-yl)boronic acid (99 mg), tripotassium phosphate (268 mg) and PdCl$_2$(dppf)CH$_2$Cl$_2$ (37 mg), and the obtained mixture was then stirred at 95° C. for 7 hours. Thereafter, water was added to the reaction mixture, and the obtained mixture was then extracted with ethyl acetate. The gathered organic layer was washed with a saturated saline, dried over anhydrous sodium sulfate, and then concentrated under a reduced pressure. The obtained residue was purified by silica gel chromatography (hexane:ethyl acetate) to obtain a product of interest (110 mg, yield: 39%).

ESI-MS m/z 562 (MH$^+$)

Example 14(2)

N-(3-(3-(4-(Hydroxymethyl) furan-2-yl)-1H-pyrrolo[2,3-b]pyridin-4-yl)cyclohex-3-en-1-yl)acrylamide (Compound 14)

THF (0.5 mL), methanol (0.5 mL) and a 2 M aqueous solution of sodium hydroxide (0.3 mL) were added to the Compound 14(1) (50 mg), and the obtained mixture was then stirred at a room temperature for 30 minutes. Thereafter, a saturated aqueous solution of ammonium chloride was added to the reaction mixture, and the obtained mixture was then extracted with chloroform. The extract was dried over anhydrous sodium sulfate, and then concentrated under a reduced pressure.

The obtained residue was dissolved in methanol (1.5 mL), and the obtained solution was then cooled to 0° C. Sodium borohydride (4.6 mg) was added to the reaction mixture, and the obtained mixture was then stirred for 10 minutes. Thereafter, a saturated saline was added to the reaction mixture, and the obtained mixture was then extracted with chloroform. The extract was dried over anhydrous sodium sulfate, and then concentrated under a reduced pressure. The obtained residue was purified by silica gel chromatography (chloroform:methanol) to obtain a corresponding alcohol product. The obtained alcohol product was subjected to the subsequent reaction without further purification.

TFA (1 mL) was added to a dichloromethane solution (1 mL) of the obtained alcohol product, and the obtained mixture was then stirred at a room temperature for 40 minutes. Thereafter, the reaction mixture was concentrated under a reduced pressure. Dichloromethane (2 mL) and diisopropylethylamine (0.2 mL) were added to the obtained residue, and the obtained mixture was then cooled to 0° C. Acryloyl chloride (7 µL) was added to the reaction mixture, and the obtained mixture was then stirred for 15 minutes. Thereafter, an ammonia aqueous solution was added to the reaction mixture, and the obtained mixture was then stirred at a room temperature for 1 hour. Thereafter, the reaction mixture was extracted with chloroform, and the gathered organic layer was washed with a saturated saline, dried over anhydrous sodium sulfate, and concentrated under a reduced pressure. The obtained residue was purified by silica gel chromatography (chloroform:methanol) to obtain the title compound (15 mg, yield: 48%).

$^1$H NMR (DMSO-d$_6$) δ: 10.70 (br. s., 1H), 8.21 (d, J=4.8 Hz, 1H), 7.47 (s, 1H), 7.43 (s, 1H), 6.89 (d, J=4.8 Hz, 1H), 6.44 (s, 1H), 6.29-6.22 (m, 1H), 6.04 (dd, J=10.6, 16.5 Hz, 2H), 5.81 (br. s., 1H), 5.64-5.59 (m, 1H), 4.57 (s, 2H), 4.21-4.05 (m, 1H), 2.44-2.22 (m, 2H), 2.17-1.79 (m, 4H)

ESI-MS m/z 364 (MH$^+$)

Example 15

N-(3-(3-(4-((Dimethylamino)methyl)furan-2-yl)-1H-pyrrolo[2,3-b]pyridin-4-yl)cyclohex-3-en-1-yl)acrylamide (Compound 15)

Dichloroethane (3 mL) and a THF solution (0.53 mL) of 2.0 M dimethylamine were added to the Compound 14(1) (100 mg), and the obtained mixture was then stirred for 10 minutes. Thereafter, acetic acid (0.06 mL) and sodium triacetoxyborohydride (377 mg) were added to the reaction mixture, and the obtained mixture was then stirred for 20 minutes. Thereafter, a saturated aqueous solution of sodium hydrogen carbonate was added to the reaction mixture, and the obtained mixture was then extracted with chloroform. The extract was dried over anhydrous sodium sulfate, and then concentrated under a reduced pressure.

The obtained residue was dissolved in THF (1 mL) and methanol (1 mL), and a 2 M aqueous solution of sodium hydroxide (1 mL) was then added to the above obtained solution. The obtained mixture was stirred at a room temperature for 30 minutes. Thereafter, a saturated aqueous solution of ammonium chloride was added to the reaction mixture, and the obtained mixture was then extracted with chloroform. The extract was dried over anhydrous sodium sulfate, and then concentrated under a reduced pressure. The obtained residue was purified by silica gel chromatography (chloroform:methanol) to obtain a corresponding protective group-removed product. The obtained protective group-removed product was subjected to the subsequent reaction without further purification.

Dichloromethane (3 mL) and TFA (1 mL) were added to the obtained protective group-removed product, and the obtained mixture was then stirred at a room temperature for 30 minutes. Thereafter, the reaction mixture was concentrated under a reduced pressure. Acetonitrile (1.5 mL), water (1.5 mL) and diisopropylethylamine (0.15 mL) were added to the obtained residue, and the obtained mixture was then cooled to 0° C. Acryloyl chloride (25 µL) was added to the reaction mixture, and the obtained mixture was then stirred for 30 minutes. Thereafter, an ammonia aqueous solution was added to the reaction mixture, and the obtained mixture was then stirred at a room temperature for 30 minutes. Thereafter, the reaction mixture was extracted with chloroform, and the gathered organic layer was washed with a saturated saline, dried over anhydrous sodium sulfate, and concentrated under a reduced pressure. The obtained residue was purified by silica gel chromatography (chloroform:methanol) to obtain the title compound (4 mg, yield: 6%).

$^1$H NMR (CDCl$_3$) δ: 10.44 (br. s., 1H), 8.29 (d, J=5.1 Hz, 1H), 7.49 (s, 1H), 7.39 (s, 1H), 6.95 (d, J=5.1 Hz, 1H), 6.38 (s, 1H), 6.31 (dd, J=2.2, 16.9 Hz, 1H), 6.12 (dd, J=10.6, 16.9 Hz, 1H), 5.90 (br. s., 1H), 5.67-5.62 (m, 2H), 4.44-4.28 (m, 1H), 3.34 (s, 2H), 2.79-2.64 (m, 1H), 2.30 (s, 6H), 2.25-2.04 (m, 3H), 1.95-1.62 (m, 2H)

ESI-MS m/z 391 (MH$^+$)

Example 16

N-(3-(3-(4-((Isopropylamino)methyl)furan-2-yl)-1H-pyrrolo[2,3-b]pyridin-4-yl)cyclohex-3-en-1-yl)acrylamide (Compound 16)

The title compound was obtained in accordance with Example 15, with exception that isopropylamine was used instead of the dimethylamine.

$^1$H NMR (CDCl$_3$) δ: 10.72 (br. s., 1H), 8.29 (d, J=5.1 Hz, 1H), 7.50 (s, 1H), 7.40 (s, 1H), 7.27 (s, 1H), 6.93 (d, J=5.1 Hz, 1H), 6.38-6.25 (m, 2H), 6.12 (dd, J=10.3, 16.9 Hz, 1H), 6.01 (d, J=7.7 Hz, 1H), 5.68-5.54 (m, 1H), 4.45-4.21 (m, 1H), 3.75-3.60 (s, 2H), 2.96-2.88 (m, 1H), 2.76-2.60 (m, 1H), 2.26-2.01 (m, 3H), 1.99-1.78 (m, 1H), 1.78-1.52 (m, 1H), 1.16-1.11 (d, 6H)

ESI-MS m/z 405 (MH$^+$)

Example 17

Example 17(1)

tert-Butyl (3-(3-iodo-5-methoxy-1-tosyl-1H-pyrrolo[2,3-b]pyridin-4-yl)cyclohex-3-en-1-yl)carbamate (Compound 17(1))

A product of interest was obtained in the form of a colorless solid in accordance with Example 1(1), with the exception that 4-chloro-5-methoxy-1H-pyrrolo[2,3-b]pyridine was used instead of the 4-bromo-1H-pyrrolo[2,3-b]pyridine.

$^1$H NMR (CDCl$_3$) δ: 8.15-8.11 (m, 1H), 8.07 (d, J=8.3 Hz, 2H), 7.86-7.82 (m, 1H), 7.30 (d, J=8.3 Hz, 2H), 5.66-5.58 (m, 1H), 4.13-3.93 (m, 1H), 3.92-3.87 (m, 3H), 2.83-2.69 (m, 1H), 2.48-2.15 (m, 6H), 1.98-1.78 (m, 2H), 1.49-1.41 (m, 9H)

ESI-MS m/z 624 (MH$^+$)

Example 17(2)

N-(3-(3-(Furan-2-yl)-5-methoxy-1H-pyrrolo[2,3-b]pyridin-4-yl)cyclohex-3-en-1-yl)acrylamide (Compound 17)

The title compound was obtained in accordance with Example 12, with the exception that the Compound 17(1) was used instead of the Compound 1(1).

$^1$H NMR (CDCl$_3$-CD$_3$OD) δ: 8.04-7.96 (m, 1H), 7.54-7.38 (m, 2H), 6.49-6.37 (m, 1H), 6.36-6.09 (m, 3H), 5.72-5.57 (m, 1H), 5.53-5.36 (m, 1H), 4.43-4.22 (m, 1H), 3.98-3.81 (m, 3H), 2.72-1.62 (m, 6H)

ESI-MS m/z 364 (MH$^+$)

Example 18

Example 18(1)

4-Chloro-5-(1-methyl-1H-pyrazol-4-yl)-1H-pyrrolo[2,3-b]pyridine (Compound 18(1))

1,4-Dioxane (15 mL), a 2 M aqueous solution of sodium carbonate (3 mL) and PdCl$_2$(dppf)CH$_2$Cl$_2$ (122 mg) were added to 4-chloro-5-iodo-1H-pyrrolo[2,3-b]pyridine (835 mg) and 1-methyl-4-(4,4,5,5-tetramethyl-1,3,2-dioxaborolan-2-yl)-1H-pyrazole (749 mg), and the temperature of the obtained mixture was then increased to 100° C., followed by stirring for 13 hours. Thereafter, water was added to the reaction mixture for dilution, and the obtained mixture was then extracted with ethyl acetate. The gathered organic layer was washed with a saturated saline, dried over anhydrous sodium sulfate, and then concentrated under a reduced pressure. The obtained residue was purified by silica gel chromatography (chloroform:methanol) to obtain a product of interest (573 mg, yield: 82%).

ESI-MS m/z 233 (MH$^+$)

Example 18(2)

tert-Butyl (3-(3-iodo-5-(1-methyl-1H-pyrazol-4-yl)-1-tosyl-1H-pyrrolo[2,3-b]pyridin-4-yl)cyclohex-3-en-1-yl)carbamate (Compound 18(2))

A product of interest was obtained in accordance with Example 1(1), with the exception that the Compound 18(1) was used instead of the 4-bromo-1H-pyrrolo[2,3-b]pyridine.

ESI-MS m/z 674 (MH$^+$)

Example 18(3)

N-(3-(3-(Furan-2-yl)-5-(1-methyl-1H-pyrazol-4-yl)-1H-pyrrolo[2,3-b]pyridin-4-yl)cyclohex-3-en-1-yl)acrylamide (Compound 18)

The title compound was obtained in accordance with Example 12, with the exception that the Compound 18(2) was used instead of the Compound 1(1).

$^1$H NMR (DMSO-d$_6$) δ: 11.97 (br. s., 1H), 8.32-8.22 (m, 1H), 8.00-7.83 (m, 2H), 7.68-7.57 (m, 3H), 6.49 (d, J=1.8 Hz, 1H), 6.34 (t, J=2.6 Hz, 1H), 6.21-6.08 (m, 1H), 6.06-5.97 (m, 1H), 5.52 (dd, J=2.6, 9.9 Hz, 1H), 5.44-5.32 (m, 1H), 3.96-3.69 (m, 4H), 2.29-1.98 (m, 2H), 1.96-1.65 (m, 3H), 1.33 (dq, J=5.3, 11.7 Hz, 1H)

ESI-MS m/z 414 (MH$^+$)

Example 19

N-(3-(5-(1-Methyl-1H-pyrazolo-4-yl)-3-(pyridin-3-yl)-1H-pyrrolo[2,3-b]pyridin-4-yl)cyclohex-3-en-1-yl)acrylamide (Compound 19)

The title compound was obtained in accordance with Example 1(2), with the exceptions that the Compound 18(2) was used instead of the Compound 1(1), and that 3-pyridineboronic acid was used instead of the phenylboronic acid.

$^1$H NMR (DMSO-d$_6$) δ: 11.96 (br. s., 1H), 8.52-8.45 (m, 2H), 8.32-8.24 (m, 1H), 7.92-7.73 (m, 2H), 7.72-7.62 (m, 1H), 7.57 (d, J=4.4 Hz, 1H), 7.53 (d, J=2.6 Hz, 1H), 7.37 (ddd, J=1.8, 5.0, 7.4 Hz, 1H), 6.17-6.07 (m, 1H), 6.00 (dd, J=2.6, 17.2 Hz, 1H), 5.50 (dd, J=1.5, 9.9 Hz, 1H), 5.42-5.27 (m, 1H), 3.84 (d, J=7.3 Hz, 3H), 3.71-3.34 (m, 1H), 2.19-2.03 (m, 1H), 2.03-1.80 (m, 2H), 1.74-1.46 (m, 2H), 1.29-1.12 (m, 1H)

ESI-MS m/z 425 (MH$^+$)

Example 20

Example 20(1)

Methyl 4-(5-((tert-butoxycarbonyl)amino)cyclohex-1-en-1-yl)-3-iodo-1-tosyl-1H-pyrrolo[2,3-b]pyridine-5-carboxylate (Compound 20(1))

A product of interest was obtained in accordance with Example 1(1), with the exception that methyl 4-chloro-1H-pyrrolo[2,3-b]pyridine-5-carboxylate was used instead of the 4-bromo-1H-pyrrolo[2,3-b]pyridine.

ESI-MS m/z 652 (MH$^+$)

Example 20(2)

Methyl 4-(5-((tert-butoxycarbonyl)amino)cyclohex-1-en-1-yl)-3-(furan-2-yl)-1H-pyrrolo[2,3-b]pyridine-5-carboxylate (Compound 20(2))

DMF (5 mL) was added to the Compound 20(1) (375 mg) and tributyl(furan-2-yl)stannane (0.217 mL), followed by nitrogen substitution. Thereafter, PdCl$_2$(PPh$_3$)$_2$ (40.0 mg) was added to the reaction mixture, and the temperature of the obtained mixture was increased to 120° C., followed by stirring for 3 hours. Thereafter, a saturated aqueous solution of ammonium chloride was added to the reaction mixture for dilution, and the obtained mixture was then extracted with ethyl acetate. The gathered organic layer was washed with water, with a saturated aqueous solution of sodium hydrogen carbonate and with a saturated saline, and dried over anhydrous sodium sulfate, followed by vacuum concentration, to obtain a corresponding coupling product. The obtained coupling product was subjected to the subsequent reaction without further purification.

THF (10 mL) and a THF solution (5 mL) of 1.0 M tetrabutylammonium fluoride were added to the obtained coupling product, and the obtained mixture was then stirred at a room temperature for 2 hours. Thereafter, a saturated aqueous solution of sodium hydrogen carbonate was added to the reaction mixture for dilution, and the obtained mixture was then extracted with ethyl acetate. The gathered organic layer was washed with water and then with a saturated saline, dried over anhydrous sodium sulfate, and then concentrated under a reduced pressure. The obtained residue was purified by silica gel chromatography (hexane:ethyl acetate) to obtain a product of interest (187 mg, yield: 74%).

ESI-MS m/z 438 (MH$^+$)

Example 20(3)

Methyl 4-(5-acrylamidecyclohex-1-en-1-yl)-3-(furan-2-yl)-1H-pyrrolo[2,3-b]pyridine-5-carboxylate (Compound 20)

Methanol (0.5 mL) and a 1,4-dioxane solution (2 mL) of 4 M hydrochloric acid were added to the Compound 20(2) (44.0 mg), and the obtained mixture was then stirred at a room temperature for 30 minutes. Thereafter, the reaction mixture was concentrated under a reduced pressure. Under a nitrogen atmosphere, dichloromethane (1.5 mL), ethanol (0.5 mL) and diisopropylethylamine (0.11 mL) were added to the mixture, and thus obtained mixture was then cooled to 0° C. Acryloyl chloride (0.010 mL) was added to the reaction mixture, and the obtained mixture was then stirred for 30 minutes. Thereafter, a methanol solution of 7 M ammonia was added to the reaction mixture, and the obtained mixture was then stirred at a room temperature for 1 hour. Thereafter, water was added to the reaction mixture for dilution, and the obtained mixture was then extracted with a chloroform solution of 20% ethanol. The gathered organic layer was dried over anhydrous sodium sulfate, and then concentrated under a reduced pressure. The obtained residue was purified by silica gel chromatography (chloroform:methanol) to obtain the title compound (23.7 mg, yield: 60%).

$^1$H NMR (DMSO-d$_6$) δ: 12.37 (br. s., 1H), 8.69 (s, 1H), 8.01 (br. s., 1H), 7.73 (d, J=2.6 Hz, 1H), 7.69 (br. s., 1H), 6.55-6.49 (m, 1H), 6.39 (d, J=2.6 Hz, 1H), 6.20 (dd, J=10.1, 17.0 Hz, 1H), 6.06 (dd, J=2.2, 16.9 Hz, 1H), 5.55 (dd, J=2.2, 9.9 Hz, 1H), 5.32-5.14 (m, 1H), 4.04-3.91 (m, 1H), 3.81 (s, 3H), 2.37-2.00 (m, 3H), 1.94-1.64 (m, 2H), 1.60-1.28 (m, 1H)

ESI-MS m/z 392 (MH$^+$)

Example 21

Example 21(1)

tert-Butyl (3-(5-carbamoyl-3-(furan-2-yl)-1H-pyrrolo[2,3-b]pyridin-4-yl)cyclohex-3-en-1-yl)carbamate (Compound 21(1))

Methanol (1 mL) and a 1 M aqueous solution of sodium hydroxide (1 mL) were added to the Compound 20(2) (92 mg), and the temperature of the obtained mixture was then increased to 80° C., followed by stirring for 13 hours. Thereafter, the reaction mixture was cooled to 0° C., and 1 M hydrochloric acid was then added to the mixture for dilution. Thereafter, the obtained mixture was extracted with a chloroform solution of 20% ethanol. The gathered organic layer was dried over anhydrous sodium sulfate, and then concentrated under a reduced pressure to obtain a corresponding carboxylic acid. The obtained carboxylic acid was subjected to the subsequent reaction without further purification.

DMF (2 mL), ammonium chloride (45.0 mg), diisopropylethylamine (0.183 mL) and HBTU (159 mg) were added to the obtained carboxylic acid, and the temperature of the obtained mixture was then increased to 80° C., followed by stirring for 3 hours. Thereafter, water was added to the reaction mixture for dilution, and the obtained mixture was then extracted with a chloroform solution of 20% ethanol. The gathered organic layer was dried over anhydrous sodium sulfate, and then concentrated under a reduced pressure. The obtained residue was purified by silica gel chromatography (chloroform:methanol) to obtain a product of interest (77.2 mg, yield: 87%).

ESI-MS m/z 423 (MH$^+$)

Example 21(2)

4-(5-Acrylamidecyclohex-1-en-1-yl)-3-(furan-2-yl)-1H-pyrrolo[2,3-b]pyridine-5-carboxamide (Compound 21)

Ethanol (0.5 mL) and a 1,4-dioxane solution (2 mL) of 4 M hydrochloric acid were added to the Compound 21(1) (77.2 mg), and the obtained mixture was then stirred at a room temperature for 10 minutes. Thereafter, the reaction mixture was concentrated under a reduced pressure. Under a nitrogen atmosphere, ethanol (1.8 mL) and diisopropylethylamine (0.160 mL) were added to the mixture, and the obtained mixture was then cooled to 0° C. An acetonitrile solution (0.100 mL) of 2 M acryloyl chloride was added to the reaction mixture, and the obtained mixture was then stirred for 30 minutes. Thereafter, a methanol solution of 7 M ammonia was added to the reaction mixture, and thus obtained mixture was then stirred at a room temperature for 30 minutes. Thereafter, water was added to the reaction mixture for dilution, and the obtained mixture was then extracted with a chloroform solution of 20% ethanol. The gathered organic layer was dried over anhydrous sodium sulfate, and then concentrated under a reduced pressure. The obtained residue was purified by silica gel chromatography (chloroform:methanol) to obtain the title compound (45.4 mg, yield: 66%).

$^1$H NMR (DMSO-d$_6$) δ: 12.16 (br. s., 1H), 8.34 (s, 1H), 8.02 (br. s., 1H), 7.92 (br. s., 1H), 7.69 (d, J=2.9 Hz, 1H), 7.67 (d, J=1.1 Hz, 1H), 7.48 (br. s., 1H), 6.51 (dd, J=1.8, 2.9 Hz, 1H), 6.39 (d, J=2.9 Hz, 1H), 6.19 (dd, J=9.9, 17.2 Hz, 1H), 6.07 (dd, J=2.2, 16.9 Hz, 1H), 5.55 (dd, J=2.6, 9.9 Hz, 1H), 5.37 (br. s., 1H), 3.92 (br. s, 1H), 2.38-2.06 (m, 2H), 2.01-1.92 (m, 2H), 1.81-1.44 (m, 2H)

ESI-MS m/z 377 (MH$^+$)

Example 22

4-(5-Acrylamidecyclohex-1-en-1-yl)-3-(furan-2-yl)-N-methyl-1H-pyrrolo[2,3-b]pyridine-5-carboxamide (Compound 22)

The title compound was obtained in accordance with Examples 21(1) and 21(2), with the exception that a methanol solution of 40% methylamine was used instead of the ammonium chloride.

$^1$H NMR (DMSO-d$_6$) δ: 12.16 (br. s., 1H), 8.47-8.19 (m, 2H), 7.99 (d, J=7.3 Hz, 1H), 7.70 (d, J=2.6 Hz, 1H), 7.66 (d, J=1.1 Hz, 1H), 6.51 (dd, J=1.8, 3.3 Hz, 1H), 6.38 (d, J=2.9 Hz, 1H), 6.21 (dd, J=9.9, 16.9 Hz, 1H), 6.13-6.05 (m, 1H), 5.56 (dd, J=2.2, 9.9 Hz, 1H), 5.34 (br. s., 1H), 3.92 (br. s., 1H), 2.75 (d, J=4.4 Hz, 3H), 2.25 (d, J=15.8 Hz, 1H), 2.16-2.03 (m, 1H), 2.03-1.89 (m, 2H), 1.81-1.49 (m, 1H)
ESI-MS m/z 391 (MH$^+$)

Example 23

4-(5-Acrylamidecyclohex-1-en-1-yl)-3-(furan-2-yl)-N,N-dimethyl-1H-pyrrolo[2,3-b]pyridine-5-carboxamide (Compound 23)

The title compound was obtained in accordance with Examples 21(1) and 21(2), with the exception that a THF solution of 2 M dimethylamine was used instead of the ammonium chloride.
$^1$H NMR (DMSO-d$_6$) δ: 12.19 (br. s., 1H), 8.10 (s, 1H), 7.93 (br. s., 1H), 7.74 (d, J=2.7 Hz, 1H), 7.67 (s, 1H), 6.53 (dd, J=1.7, 3.2 Hz, 1H), 6.41 (d, J=3.2 Hz, 1H), 6.21 (dd, J=9.9, 17.2 Hz, 1H), 6.08 (dd, J=2.3, 17.2 Hz, 1H), 5.57 (dd, J=2.4, 10.2 Hz, 1H), 5.43 (br. s., 1H), 3.86 (br. s., 1H), 2.99 (s, 3H), 2.78 (br. s., 3H), 2.22 (br. s., 1H), 2.03 (br. s., 3H), 1.71 (br. s., 1H), 1.44 (br. s., 1H)
ESI-MS m/z 405 (MH$^+$)

Example 24

Example 24(1)

tert-Butyl (3-(5-formyl-1H-pyrrolo[2,3-b]pyridin-4-yl)cyclohex-3-en-1-yl)carbamate (Compound 24(1))

1,4-Dioxane (20 mL), a 2 M aqueous solution of sodium carbonate (6 mL) and Pd(PPh$_3$)$_4$ (318 mg) were added to 4-chloro-1H-pyrrolo[2,3-b]pyridine-5-carbaldehyde (1.00 g) and the compound of Reference Example 1(2a) (1.96 g), and the temperature of the obtained mixture was then increased to 100° C., followed by stirring for 14 hours. Thereafter, water was added to the reaction mixture for dilution, and the obtained mixture was then extracted with chloroform. The gathered organic layer was washed with a saturated saline, dried over anhydrous sodium sulfate, and then concentrated under a reduced pressure. The obtained residue was purified by silica gel chromatography (chloroform:methanol) to obtain a product of interest (1.70 g, yield: 91%).
ESI-MS m/z 342 (MH$^+$)

Example 24(2)

tert-Butyl (3-(5-formyl-3-iodo-1-tosyl-1H-pyrrolo[2,3-b]pyridin-4-yl)cyclohex-3-en-1-yl)carbamate (Compound 24(2))

DMF (5 mL) was added to the Compound 24(1) (341 mg), and the obtained mixture was then cooled to 0° C. Thereafter, N-iodosuccinimide (247 mg) was added to the reaction mixture, and the obtained mixture was then stirred for 1 hour. Thereafter, a 10% aqueous solution of sodium hydrogen sulfite was added to the reaction mixture at 0° C., and the obtained mixture was then diluted with a saturated aqueous solution of sodium hydrogen carbonate, and was then extracted with ethyl acetate. The gathered organic layer was washed with water and then with a saturated saline. The resultant was dried over anhydrous sodium sulfate, and then concentrated under a reduced pressure. The obtained residue was purified by silica gel chromatography (chloroform:methanol) to obtain a corresponding iodine product. The obtained iodine product was subjected to the subsequent reaction without further purification.

DMF (5 mL) was added to the obtained iodine product, and the obtained mixture was then cooled to 0° C. Then, 60% sodium hydride (96.0 mg) was added to the reaction mixture. Thus obtained mixture was stirred at a room temperature for 30 minutes, and para-toluenesulfonyl chloride (229 mg) was then added to the reaction mixture at 0° C. The obtained mixture was stirred at a room temperature for 1 hour. Thereafter, a saturated aqueous solution of ammonium chloride was added to the reaction mixture for dilution, and the obtained mixture was then extracted with ethyl acetate. The gathered organic layer was washed with water and then with a saturated saline. The resultant was dried over anhydrous sodium sulfate, and then concentrated under a reduced pressure. The obtained residue was purified by silica gel chromatography (hexane:ethyl acetate) to obtain a product of interest (352 mg, yield: 57%).
ESI-MS m/z 622 (MH$^+$)

Example 24(3)

tert-Butyl (3-(5-formyl-3-(furan-2-yl)-1H-pyrrolo[2,3-b]pyridin-4-yl)cyclohex-3-en-1-yl)carbamate (Compound 24(3))

DMF (3 mL) was added to the Compound 24(2) (186 mg) and tributyl(furan-2-yl)stannane (0.113 mL), followed by nitrogen substitution. Thereafter, PdCl$_2$(PPh$_3$)$_2$ (21.0 mg) was added to the reaction mixture, and the temperature of the obtained mixture was then increased to 120° C., followed by stirring for 3 hours. Thereafter, a saturated aqueous solution of ammonium chloride was added to the reaction mixture for dilution, and the obtained mixture was then extracted with ethyl acetate. The gathered organic layer was washed with water, with a saturated aqueous solution of sodium hydrogen carbonate and with a saturated saline, dried over anhydrous sodium sulfate, and then concentrated under a reduced pressure to obtain a corresponding coupling product. The obtained coupling product was subjected to the subsequent reaction without further purification.

THF (6 mL) and a THF solution (2 mL) of 1.0 M tetrabutylammonium fluoride were added to the obtained coupling product, and the obtained mixture was then stirred at a room temperature for 2 hours. Thereafter, a saturated aqueous solution of sodium hydrogen carbonate was added to the reaction mixture for dilution, and the obtained mixture was then extracted with ethyl acetate. The gathered organic layer was washed with water and then with a saturated saline. The resultant was dried over anhydrous sodium sulfate, and then concentrated under a reduced pressure. The obtained residue was purified by silica gel chromatography (hexane:ethyl acetate) to obtain a product of interest (110 mg, yield: 90%).
ESI-MS m/z 408 (MH$^+$)

Example 24(4)

tert-Butyl (3-3-(furan-2-yl)-5-(hydroxymethyl)-1H-pyrrolo[2,3-b]pyridin-4-yl)cyclohex-3-en-1-yl)carbamate (Compound 24(4))

Methanol (3 mL) was added to the Compound 24(3) (55.0 mg), and the obtained mixture was then cooled to 0° C.

Sodium borohydride (22.0 mg) was added to the reaction mixture, and the obtained mixture was then stirred at a room temperature for 1 hour. Thereafter, a saturated aqueous solution of ammonium chloride was added to the reaction mixture at 0° C. for dilution, and the obtained mixture was then extracted with ethyl acetate. The gathered organic layer was washed with water, with a saturated aqueous solution of sodium hydrogen carbonate and with a saturated saline, and dried over anhydrous sodium sulfate, followed by vacuum concentration. The obtained residue was purified by silica gel chromatography (chloroform:methanol) to obtain a product of interest (53.2 mg, yield: 96%).

ESI-MS m/z 410 (MH$^+$)

Example 24(5)

N-(3-(3-(Furan-2-yl)-5-(hydroxymethyl)-1H-pyrrolo[2,3-b]pyridin-4-yl)cyclohex-3-en-1-yl)acrylamide (Compound 24)

Ethanol (0.5 mL) and a 1,4-dioxane solution (2 mL) of 4 M hydrochloric acid were added to the Compound 24(4) (53.2 mg), and the obtained mixture was then stirred at a room temperature for 30 minutes. Thereafter, the reaction mixture was concentrated under a reduced pressure. Under a nitrogen atmosphere, dichloromethane (1.5 mL), ethanol (0.5 mL) and diisopropylethylamine (0.114 mL) were added to the mixture, and the obtained mixture was then cooled to 0° C. Acryloyl chloride (0.012 mL) was added to the reaction mixture, and the obtained mixture was then stirred for 30 minutes. Thereafter, a methanol solution of 7 M ammonia was added to the reaction mixture, and the obtained mixture was then stirred at a room temperature for 1 hour. Thereafter, water was added to the reaction mixture for dilution, and the obtained mixture was then extracted with a chloroform solution of 20% ethanol. The gathered organic layer was dried over anhydrous sodium sulfate, and then concentrated under a reduced pressure. The obtained residue was purified by silica gel chromatography (chloroform:methanol) to obtain the title compound (22.9 mg, yield: 49%).

$^1$H NMR (DMSO-d$_6$) δ: 11.90 (br. s., 1H), 8.28 (d, J=6.2 Hz, 1H), 8.01 (d, J=7.7 Hz, 1H), 7.65 (d, J=7.3 Hz, 1H), 7.62-7.58 (m, 1H), 6.52-6.47 (m, 1H), 6.37 (t, J=2.4 Hz, 1H), 6.24-6.14 (m, 1H), 6.05 (dd, J=2.2, 16.9 Hz, 1H), 5.54 (dd, J=2.2, 9.9 Hz, 1H), 5.45-5.33 (m, 1H), 5.04 (td, J=5.4, 18.2 Hz, 1H), 4.63-4.45 (m, 2H), 3.92 (br. s., 1H), 2.33-2.06 (m, 3H), 2.05-1.92 (m, 1H), 1.77 (s, 1H), 1.59-1.27 (m, 1H)

ESI-MS m/z 364 (MH$^+$)

Example 25

Example 25(1)

tert-Butyl (3-(5-formyl-3-iodo-1-((2-(trimethylsilyl)ethoxy)methyl)-1H-pyrrolo[2,3-b]pyridin-4-yl)cyclohex-3-en-1-yl)carbamate (Compound 25(1))

DMF (3.2 mL) was added to the Compound 24(1) (215 mg), and the obtained mixture was then cooled to 0° C. N-iodosuccinimide (156 mg) was added to the reaction mixture, and the obtained mixture was then stirred for 1 hour. Thereafter, a 10% aqueous solution of sodium hydrogen sulfite was added to the reaction mixture at 0° C., and the obtained mixture was then diluted with a saturated aqueous solution of sodium hydrogen carbonate, and was then extracted with ethyl acetate. The gathered organic layer was washed with water and then with a saturated saline. The resultant was dried over anhydrous sodium sulfate, and then concentrated under a reduced pressure. The obtained residue was purified by silica gel chromatography (hexane:ethyl acetate) to obtain a corresponding iodine product. The obtained iodine product was subjected to the subsequent reaction without further purification.

DMF (3.2 mL) was added to the obtained iodine product, and the obtained mixture was then cooled to 0° C. Thereafter, 60% sodium hydride (60.0 mg) was added to the reaction mixture. Thus obtained mixture was stirred at a room temperature for 30 minutes, and 2-(trimethylsilyl)ethoxymethyl chloride (0.134 mL) was then added to the reaction mixture at 0° C. The obtained mixture was stirred at a room temperature for 1 hour. Thereafter, a saturated aqueous solution of ammonium chloride was added to the reaction mixture for dilution, and the obtained mixture was then extracted with ethyl acetate. The gathered organic layer was washed with water and then with a saturated saline. The resultant was dried over anhydrous sodium sulfate, and then concentrated under a reduced pressure. The obtained residue was purified by silica gel chromatography (hexane:ethyl acetate) to obtain a product of interest (190 mg, yield: 50%).

ESI-MS m/z 598 (MH$^+$)

Example 25(2)

tert-Butyl (3-(3-(furan-2-yl)-5-(hydroxymethyl)-1-((2-(trimethylsilyl)ethoxy)methyl)-1H-pyrrolo[2,3-b]pyridin-4-yl)cyclohex-3-en-1-yl)carbamate (Compound 25(2))

DMF (3.2 mL) was added to the Compound 25(1) (190 mg) and tributyl(furan-2-yl)stannane (0.120 mL), followed by nitrogen substitution. Thereafter, PdCl$_2$(PPh$_3$)$_2$ (22.0 mg) was added to the reaction mixture, and the temperature of the obtained mixture was then increased to 120° C., followed by stirring for 3 hours. Thereafter, a saturated aqueous solution of ammonium chloride was added to the reaction mixture for dilution, and the obtained mixture was then extracted with ethyl acetate. The gathered organic layer was washed with water and then with a saturated saline, dried over anhydrous sodium sulfate, and then concentrated under a reduced pressure to obtain a corresponding coupling product. The obtained coupling product was subjected to the subsequent reaction without further purification.

Methanol (2.5 mL) was added to the obtained coupling product, and the obtained mixture was then cooled to 0° C. Sodium borohydride (37.0 mg) was added to the reaction mixture, and the obtained mixture was then stirred at a room temperature for 1 hour. Thereafter, a saturated aqueous solution of ammonium chloride was added to the reaction mixture at 0° C., and the obtained mixture was then extracted with ethyl acetate. The gathered organic layer was washed with water, with a saturated aqueous solution of sodium hydrogen carbonate and with a saturated saline, and dried over anhydrous sodium sulfate, followed by vacuum concentration. The obtained residue was purified by silica gel chromatography (chloroform:methanol) to obtain a product of interest (117 mg, yield: 68%).

ESI-MS m/z 540 (MH$^+$)

Example 25(3)

tert-Butyl (3-(3-(furan-2-yl)-5-(methoxymethyl)-1-((2-(trimethylsilyl)ethoxy)methyl)-1H-pyrrolo[2,3-b]pyridin-4-yl)cyclohex-3-en-1-yl)carbamate (Compound 25(3))

DMF (1 mL) was added to the Compound 25(2) (54.0 mg), and the obtained mixture was then cooled to 0° C.

Thereafter, 60% sodium hydride (10.0 mg) was added to the reaction mixture. The obtained mixture was stirred at a room temperature for 30 minutes, and iodomethane (0.008 mL) was then added to the reaction mixture at 0° C. Thus obtained mixture was stirred at a room temperature for 4 hours. Thereafter, a saturated aqueous solution of ammonium chloride was added to the reaction mixture for dilution, and the obtained mixture was then extracted with ethyl acetate. The gathered organic layer was washed with water and then with a saturated saline. The resultant was dried over anhydrous sodium sulfate, and then concentrated under a reduced pressure. The obtained residue was purified by silica gel chromatography (hexane:ethyl acetate) to obtain a product of interest (26.1 mg, yield: 47%).

ESI-MS m/z 554 (MH$^+$)

Example 25(4)

N-(3-(3-(Furan-2-yl)-5-(methoxymethyl)-1H-pyrrolo[2,3-b]pyridin-4-yl)cyclohex-3-en-1-yl)acrylamide (Compound 25)

THF (1 mL) and a THF solution (0.235 mL) of 1.0 M tetrabutylammonium fluoride were added to the Compound 25(3) (26.1 mg), and the temperature of the obtained mixture was then increased to 70° C., followed by stirring for 4 hours. Thereafter, a saturated aqueous solution of sodium hydrogen carbonate was added to the reaction mixture for dilution, and the obtained mixture was then extracted with ethyl acetate. The gathered organic layer was washed with a saturated saline, dried over anhydrous sodium sulfate, and then concentrated under a reduced pressure. The obtained residue was purified by silica gel chromatography (hexane:ethyl acetate) to obtain a corresponding protective group-removed product. The obtained compound was subjected to the subsequent reaction without further purification.

Ethanol (0.5 mL) and a 1,4-dioxane solution (2 mL) of 4 M hydrochloric acid were added to the obtained protective group-removed product, and the obtained mixture was then stirred at a room temperature for 10 minutes. Thereafter, the reaction mixture was concentrated under a reduced pressure. Under a nitrogen atmosphere, THF (0.5 mL), a saturated aqueous solution of sodium hydrogen carbonate (0.5 mL) and diisopropylethylamine (0.013 mL) were added to the mixture, and the obtained mixture was then cooled to 0° C. An 2 M solution of acryloyl chloride in acetonitrile (0.021 mL) was added to the reaction mixture, and the obtained mixture was then stirred at a room temperature for 30 minutes. Thereafter, water was added to the reaction mixture for dilution, and the obtained mixture was then extracted with chloroform. The gathered organic layer was dried over anhydrous sodium sulfate, and then concentrated under a reduced pressure. The obtained residue was purified by silica gel chromatography (chloroform:methanol) to obtain the title compound (10.4 mg, yield: 58%).

$^1$H NMR (DMSO-d$_6$) δ: 11.98 (br. s., 1H), 8.23 (d, J=2.2 Hz, 1H), 7.99 (dd, J=7.5, 18.9 Hz, 1H), 7.66 (dd, J=1.1, 9.2 Hz, 1H), 7.62 (d, J=2.6 Hz, 1H), 6.53-6.48 (m, 1H), 6.38 (dd, J=3.1, 6.8 Hz, 1H), 6.27-6.13 (m, 1H), 6.10-6.00 (m, 1H), 5.54 (td, J=2.9, 9.9 Hz, 1H), 5.40 (d, J=15.8 Hz, 1H), 4.55-4.39 (m, 1H), 4.37-4.26 (m, 1H), 3.93 (br. s., 1H), 3.25 (d, J=10.6 Hz, 3H), 2.29-2.17 (m, 2H), 2.15-1.95 (m, 2H), 1.87-1.71 (m, 1H), 1.57-1.42 (m, 1H)

ESI-MS m/z 378 (MH$^+$)

Example 26

Example 26(1)

tert-Butyl (3-(5-((dimethylamino)methyl)-3-(furan-2-yl)-1H-pyrrolo[2,3-b]pyridin-4-yl)cyclohex-3-en-1-yl)carbamate (Compound 26(1))

THF (1.1 mL), a THF solution (0.067 mL) of 2 M dimethylamine and triphenylphosphine (35.0 mg) were added to the Compound 24(4) (45.8 mg), and diisopropyl azodicarboxylate (0.026 mL) was then added to the above mixture at 0° C. The obtained mixture was stirred at a room temperature for 17 hours. Thereafter, water was added to the reaction mixture for dilution, and the obtained mixture was then extracted with a chloroform solution of 20% ethanol. The gathered organic layer was dried over anhydrous sodium sulfate, and then concentrated under a reduced pressure. The obtained residue was purified by silica gel chromatography (chloroform:methanol) to obtain a product of interest (12.4 mg, yield: 25%).

Example 26(2)

N-(3-(5-((Dimethylamino)methyl)-3-(furan-2-yl)-1H-pyrrolo[2,3-b]pyridin-4-yl)cyclohex-3-en-1-yl)acrylamide (Compound 26)

Ethanol (0.5 mL) and a 1,4-dioxane solution (2 mL) of 4 M hydrochloric acid were added to the Compound 26(1) (12.4 mg), and the obtained mixture was then stirred at a room temperature for 10 minutes. Thereafter, the reaction mixture was concentrated under a reduced pressure. Under a nitrogen atmosphere, ethanol (1 mL) and diisopropylethylamine (0.049 mL) were added to the mixture, and the obtained mixture was then cooled to 0° C. An acetonitrile solution (0.017 mL) of 2 M acryloyl chloride was added to the reaction mixture, and the obtained mixture was then stirred for 1 hour. Thereafter, a methanol solution of 7 M ammonia was added to the reaction mixture, and thus obtained mixture was then stirred at a room temperature for 30 minutes. Thereafter, water was added to the reaction mixture for dilution, and the obtained mixture was then extracted with a chloroform solution of 20% ethanol. The gathered organic layer was dried over anhydrous sodium sulfate, and then concentrated under a reduced pressure. The obtained residue was purified by basic silica gel chromatography (ethyl acetate:methanol) to obtain the title compound (7.3 mg, yield: 66%).

$^1$H NMR (DMSO-d$_6$) δ: 11.90 (br. s., 1H), 8.21 (d, J=2.2 Hz, 1H), 7.96 (dd, J=7.7, 16.9 Hz, 1H), 7.65 (td, J=0.9, 10.3 Hz, 1H), 7.57 (t, J=2.7 Hz, 1H), 6.49 (ddd, J=1.8, 3.0, 7.6 Hz, 1H), 6.36 (dd, J=3.1, 8.6 Hz, 1H), 6.27-6.13 (m, 1H), 6.10-6.00 (m, 1H), 5.59-5.49 (m, 1H), 5.36 (d, J=19.1 Hz, 1H), 3.93 (d, J=8.1 Hz, 1H), 3.59-3.47 (m, 1H), 3.27-3.11 (m, 1H), 2.34-2.16 (m, 3H), 2.14-2.09 (m, 6H), 2.08-1.88 (m, 2H), 1.84-1.70 (m, 1H)

ESI-MS m/z 391 (MH$^+$)

Example 27

N-(3-(3-(Furan-2-yl)-5-(morpholinomethyl)-1H-pyrrolo[2,3-b]pyridin-4-yl)cyclohex-3-en-1-yl)acrylamide (Compound 27)

The title compound was obtained in accordance with Examples 26(1) and 26(2), with the exception that morpholine was used instead of the THF solution of 2 M dimethylamine.

¹H NMR (DMSO-d₆) δ: 11.92 (br. s., 1H), 8.18 (d, J=18.0 Hz, 1H), 7.95 (t, J=8.6 Hz, 1H), 7.65 (d, J=7.0 Hz, 1H), 7.58 (dd, J=2.6, 6.2 Hz, 1H), 6.49 (td, J=2.5, 10.7 Hz, 1H), 6.37 (dd, J=2.9, 15.4 Hz, 1H), 6.28-6.13 (m, 1H), 6.10-5.99 (m, 1H), 5.59-5.49 (m, 1H), 5.39 (d, J=11.4 Hz, 1H), 3.93 (br. s., 1H), 3.70-3.57 (m, 1H), 3.57-3.42 (m, 4H), 3.19 (d, J=12.5 Hz, 1H), 2.43-2.17 (m, 7H), 2.14-1.91 (m, 2H), 1.77 (br. s., 1H)

ESI-MS m/z 433 (MH⁺)

Example 28

Example 28(1)

N-(3-(3-Iodo-1-tosyl-1H-pyrrolo[2,3-b]pyridin-4-yl) cyclohex-3-en-1-yl)acrylamide (Compound 28(1))

Methanol (60 mL) and a 1,4-dioxane solution (10 mL) of 4 M hydrochloric acid were added to the Compound 1(1) (5.91 g), and the obtained mixture was then stirred at a room temperature for 2 hours. Thereafter, the reaction mixture was concentrated under a reduced pressure, and dichloromethane (60 mL) and diisopropylethylamine (8.89 mL) were then added to the concentrate. The obtained mixture was cooled to 0° C. Acryloyl chloride (1.13 mL) was added to the reaction mixture, and the obtained mixture was then stirred at 0° C. for 30 minutes. Thereafter, an ammonia aqueous solution, chloroform and methanol were successively added to the reaction mixture, and thus obtained mixture was then stirred at a room temperature for 1 hour. Thereafter, the reaction mixture was extracted with chloroform. The gathered organic layer was washed with a saturated saline, dried over anhydrous sodium sulfate, and then concentrated under a reduced pressure. The obtained residue was purified by silica gel chromatography (hexane:ethyl acetate) to obtain a product of interest (3.90 g, yield: 72%).

¹H NMR (CDCl₃) δ: 8.34 (d, J=4.9 Hz, 1H), 8.09 (d, J=8.5 Hz, 2H), 7.89 (s, 1H), 7.29 (d, J=8.5 Hz, 2H), 6.94 (d, J=4.9 Hz, 1H), 6.33-6.27 (m, 1H), 6.14-6.05 (m, 1H), 5.85 (br. d, J=6.1 Hz, 1H), 5.76-5.71 (m, 1H), 5.66-5.62 (m, 1H), 4.54-4.39 (m, 1H), 2.77-2.65 (m, 1H), 2.45-2.34 (m, 4H), 2.25-2.12 (m, 1H), 2.07-1.96 (m, J=1.0 Hz, 1H), 1.85-1.70 (m, 2H)

ESI-MS m/z 548 (MH⁺)

Example 28(2)

N-(3-(3-(1-Methyl-1H-pyrazol-4-yl)-1H-pyrrolo[2, 3-b]pyridin-4-yl)cyclohex-3-en-1-yl)acrylamide (Compound 28)

1,4-Dioxane (1.2 mL) and water (0.2 mL) were added to the Compound 28(1) (36.7 mg), 1-methyl-4-(4,4,5,5-tetramethyl-1,3,2-dioxaborolan-2-yl)-1H-pyrazole (21.0 mg) and tripotassium phosphate (35.6 mg), followed by nitrogen substitution. Thereafter, PdCl₂ (dppf)CH₂Cl₂ (4.9 mg) was added to the reaction mixture, and the obtained mixture was then stirred at 100° C. for 1 hour. Thereafter, the reaction mixture was cooled to a room temperature, and ethyl acetate and water were then added to the mixture. Thus obtained mixture was filtered through Celite. The filtrate was extracted with ethyl acetate, and the gathered organic layer was then washed with water and then with a saturated saline. The resultant was dried over anhydrous sodium sulfate, and then concentrated under a reduced pressure.

THF (0.5 mL) and a THF solution (0.5 mL) of 1.0 M tetrabutylammonium fluoride were added to the obtained residue, and the obtained mixture was then stirred at a room temperature for 14 hours. Thereafter, the reaction mixture was concentrated under a reduced pressure, and a 0.067 M phosphate buffer (pH 7.4) was then added to the concentrate. The water layer was extracted with ethyl acetate. The gathered organic layer was washed with a saturated saline, dried over anhydrous sodium sulfate, and then concentrated under a reduced pressure. The obtained residue was purified by silica gel chromatography (chloroform:methanol) to obtain the title compound (14.0 mg, yield: 60%).

¹H NMR (CDCl₃-CD₃OD) δ: 8.21-8.12 (m, 1H), 7.46-7.38 (m, 2H), 7.27-7.23 (m, 1H), 6.90-6.84 (m, 1H), 6.30-6.11 (m, 2H), 5.66-5.57 (m, 2H), 4.11-3.99 (m, 1H), 3.96 (s, 3H), 2.59-2.45 (m, 1H), 2.26-1.76 (m, 4H), 1.59-1.39 (m, 1H)

ESI-MS m/z 348 (MH⁺)

Example 29

N-(3-(3-(1-(Oxetan-3-yl)-1H-pyrazol-4-yl)-1H-pyrrolo[2,3-b]pyridin-4-yl)cyclohex-3-en-1-yl)acrylamide The title compound was obtained in accordance with Example 28(2), with the exception that 1-(oxetan-3-yl)-4-(4,4,5,5-tetramethyl-1,3,2-dioxaborolan-2-yl)-1H-pyrazole was used instead of the 1-methyl-4-(4,4,5,5-tetramethyl-1,3,2-dioxaborolan-2-yl)-1H-pyrazole.

¹H NMR (CDCl₃-CD₃OD) δ: 8.22-8.16 (m, 1H), 7.62 (s, 1H), 7.56 (s, 1H), 7.29 (s, 1H), 6.89 (d, J=5.1 Hz, 1H), 6.30-6.21 (m, 1H), 6.14 (dd, J=10.2, 17.1 Hz, 1H), 5.67-5.50 (m, 3H), 5.16-5.07 (m, 4H), 4.03-3.85 (m, 1H), 2.64-2.50 (m, 1H), 2.05 (d, J=1.0 Hz, 3H), 1.91-1.79 (m, 1H), 1.56-1.39 (m, 1H)

ESI-MS m/z 390 (MH⁺)

Example 30

N-(3-(3-(cyclohex-1-en-1-yl)-1H-pyrrolo[2,3-b]pyridin-4-yl)cyclohex-3-en-1-yl)acrylamide (Compound 30)

The title compound was obtained in accordance with Example 28(2), with the exception that 2-(cyclohex-1-en-1-yl)-4,4,5,5-tetramethyl-1,3,2-dioxaborolane was used instead of the 1-methyl-4-(4,4,5,5-tetramethyl-1,3,2-dioxaborolan-2-yl)-1H-pyrazole.

¹H NMR (CDCl₃-CD₃OD) δ: 8.20-8.04 (m, 1H), 7.20-7.09 (m, 1H), 6.93-6.82 (m, 1H), 6.37-6.22 (m, 1H), 6.21-6.09 (m, 1H), 5.93-5.79 (m, 1H), 5.76-5.54 (m, 2H), 4.36-4.22 (m, 1H), 2.88-2.69 (m, 1H), 2.48-1.98 (m, 8H), 1.68 (m, 5H)

ESI-MS m/z 348 (MH⁺)

Example 31

N-(3-(3-(3,6-Dihydro-2H-pyran-4-yl)-1H-pyrrolo[2, 3-b]pyridin-4-yl)cyclohex-3-en-1-yl)acrylamide (Compound 31)

The title compound was obtained in accordance with Example 28(2), with the exception that 2-(3,6-dihydro-2H-pyran-4-yl)-4,4,5,5-tetramethyl-1,3,2-dioxaborolane was used instead of the 1-methyl-4-(4,4,5,5-tetramethyl-1,3,2-dioxaborolan-2-yl)-1H-pyrazole.

¹H NMR (CDCl₃-CD₃OD) δ: 8.20-8.07 (m, 1H), 7.23-7.15 (m, 1H), 6.91-6.82 (m, 1H), 6.34-6.07 (m, 2H), 5.94-

5.81 (m, 1H), 5.78-5.58 (m, 2H), 4.41-4.17 (m, 3H), 4.04-3.80 (m, 2H), 2.74-2.58 (m, 1H), 2.51-2.23 (m, 5H), 2.09-1.91 (m, 1H), 1.70-1.51 (m, 1H)
ESI-MS m/z 350 (MH+)

Example 32

N-(3-(3-(3-Oxocyclohex-1-en-1-yl)-1H-pyrrolo[2,3-b]pyridin-4-yl)cyclohex-3-en-1-yl)acrylamide (Compound 32)

The title compound was obtained in accordance with Example 28(2), with the exception that 3-(4,4,5,5-tetramethyl-1,3,2-dioxaborolan-2-yl)cyclohex-2-enone was used instead of the 1-methyl-4-(4,4,5,5-tetramethyl-1,3,2-dioxaborolan-2-yl)-1H-pyrazole.

$^1$H NMR (CDCl$_3$-CD$_3$OD) δ: 8.24 (d, J=4.9 Hz, 1H), 7.67 (s, 1H), 7.06 (d, J=4.9 Hz, 1H), 6.44-6.20 (m, 2H), 5.95 (s, 1H), 5.74-5.52 (m, 2H), 4.51-4.25 (m, 1H), 3.06-2.61 (m, 3H), 2.59-2.43 (m, 2H), 2.41-2.04 (m, 5H), 2.00-1.81 (m, 1H), 1.78-1.56 (m, 1H)
ESI-MS m/z 362 (MH+)

Example 33

N-(3-(3-(Cyclocyclopent-1-en-1-yl)-1H-pyrrolo[2,3-b]pyridin-4-yl)cyclohex-3-en-1-yl)acrylamide (Compound 33)

The title compound was obtained in accordance with Example 28(2), with the exception that 2-(cyclopent-1-en-1-yl)-4,4,5,5-tetramethyl-1,3,2-dioxaborolane was used instead of the 1-methyl-4-(4,4,5,5-tetramethyl-1,3,2-dioxaborolan-2-yl)-1H-pyrazole.

$^1$H NMR (CDCl$_3$-CD$_3$OD) δ: 8.13 (d, J=4.9 Hz, 1H), 7.37 (s, 1H), 6.90 (d, J=4.9 Hz, 1H), 6.27 (dd, J=1.7, 17.1 Hz, 1H), 6.16 (dd, J=10.0, 17.1 Hz, 1H), 5.87-5.80 (m, 1H), 5.76-5.70 (m, 1H), 5.65 (dd, J=1.7, 10.0 Hz, 1H), 4.34-4.19 (m, 1H), 2.54 (m, 4H), 2.43-2.19 (m, 4H), 2.07-1.93 (m, 3H), 1.72-1.55 (m, 1H)
ESI-MS m/z 334 (MH+)

Example 34

N-(3-(3-(2,5-Dihydrofuran-3-yl)-1H-pyrrolo[2,3-b]pyridin-4-yl)cyclohex-3-en-1-yl)acrylamide (Compound 34)

The title compound was obtained in accordance with Example 28(2), with the exception that 2-(2,5-dihydrofuran-3-yl)-4,4,5,5-tetramethyl-1,3,2-dioxaborolane was used instead of the 1-methyl-4-(4,4,5,5-tetramethyl-1,3,2-dioxaborolan-2-yl)-1H-pyrazole.

$^1$H NMR (CDCl$_3$-CD$_3$OD) δ: 8.18 (d, J=4.9 Hz, 1H), 7.35 (s, 1H), 6.93 (d, J=4.9 Hz, 1H), 6.29 (dd, J=2.0, 17.1 Hz, 1H), 6.18 (dd, J=9.8, 17.1 Hz, 1H), 5.92-5.81 (m, 2H), 5.65 (dd, J=2.0, 9.8 Hz, 1H), 4.92-4.78 (m, 4H), 4.38-4.21 (m, 1H), 2.80-2.68 (m, 1H), 2.46-2.24 (m, 3H), 2.08-1.94 (m, 1H), 1.75-1.59 (m, 1H)
ESI-MS m/z 336 (MH+)

Example 35

N-(3-(3-(4,5-Dihydrofuran-3-yl)-1H-pyrrolo[2,3-b]pyridin-4-yl)cyclohex-3-en-1-yl)acrylamide (Compound 35)

The title compound was obtained in accordance with Example 28(2), with the exception that 2-(4,5-dihydrofuran-3-yl)-4,4,5,5-tetramethyl-1,3,2-dioxaborolane was used instead of the 1-methyl-4-(4,4,5,5-tetramethyl-1,3,2-dioxaborolan-2-yl)-1H-pyrazole.

$^1$H NMR (CDCl$_3$-CD$_3$OD) δ: 8.14 (d, J=5.1 Hz, 1H), 7.20 (s, 1H), 6.89 (d, J=5.1 Hz, 1H), 6.52-6.45 (m, 1H), 6.28 (dd, J=1.7, 16.8 Hz, 1H), 6.17 (dd, J=10.2, 16.8 Hz, 1H), 5.92-5.85 (m, 1H), 5.65 (dd, J=1.7, 10.2 Hz, 1H), 4.55-4.42 (m, 2H), 4.38-4.25 (m, 1H), 3.00-2.89 (m, 2H), 2.82-2.68 (m, 1H), 2.46-2.23 (m, 3H), 2.10-2.00 (m, 1H), 1.80-1.65 (m, 1H)
ESI-MS m/z 336 (MH+)

Example 36

N-(3-(3-(6-Methoxypyridin-3-yl)-1H-pyrrolo[2,3-b]pyridin-4-yl)cyclohex-3-en-1-yl)acrylamide (Compound 36)

The title compound was obtained in accordance with Example 28(2), with the exception that (6-methoxypyridin-3-yl)boronic acid was used instead of the 1-methyl-4-(4,4,5,5-tetramethyl-1,3,2-dioxaborolan-2-yl)-1H-pyrazole.

$^1$H NMR (CDCl$_3$) δ: 11.09 (br. s., 1H), 8.31 (d, J=5.1 Hz, 1H), 8.07 (d, J=2.6 Hz, 1H), 7.59 (dd, J=2.6, 8.4 Hz, 1H), 7.39 (s, 1H), 6.95 (d, J=5.1 Hz, 1H), 6.80 (d, J=8.4 Hz, 1H), 6.36-6.25 (m, 2H), 5.97 (d, J=8.4 Hz, 1H), 5.64 (dd, J=3.7, 8.1 Hz, 1H), 5.41-5.28 (m, 1H), 4.38-4.27 (m, 1H), 3.99 (s, 3H), 2.78-2.73 (m, 1H), 2.24-1.94 (m, 4H), 1.89-1.69 (m, 1H)
ESI-MS m/z 375 (MH+)

Example 37

N-(3-(3-(6-Fluoropyridin-3-yl)-1H-pyrrolo[2,3-b]pyridin-4-yl)cyclohex-3-en-1-yl)acrylamide (Compound 37)

The title compound was obtained in accordance with Example 28(2), with the exception that (6-fluoropyridin-3-yl)boronic acid was used instead of the 1-methyl-4-(4,4,5,5-tetramethyl-1,3,2-dioxaborolan-2-yl)-1H-pyrazole.

$^1$H NMR (CDCl$_3$) δ: 11.75 (s, 1H), 8.33 (d, J=4.8 Hz, 1H), 8.11 (s, 1H), 7.82-7.74 (m, 1H), 7.46 (s, 1H), 7.00-6.95 (m, 2H), 6.37-6.24 (m, 2H), 6.03-5.92 (m, 1H), 5.68-5.64 (m, 1H), 5.33 (br. s., 1H), 4.30 (t, J=7.1 Hz, 1H), 2.82-2.63 (m, 1H), 2.27-2.05 (m, 1H), 2.11-1.91 (m, 2H), 1.87-1.71 (m, 2H)
ESI-MS m/z 363 (MH+)

Example 38

N-(3-(3-(2-Fluoropyridin-3-yl)-1H-pyrrolo[2,3-b]pyridin-4-yl)cyclohex-3-en-1-yl)acrylamide (Compound 38)

The title compound was obtained in accordance with Example 28(2), with the exception that (2-fluoropyridin-3-yl)boronic acid was used instead of the 1-methyl-4-(4,4,5,5-tetramethyl-1,3,2-dioxaborolan-2-yl)-1H-pyrazole.

$^1$H NMR (CDCl$_3$) δ: 11.34 (br. s., 1H), 8.34 (d, J=4.8 Hz, 1H), 8.19-8.15 (m, 1H), 7.83 (ddd, J=2.0, 7.2, 9.4 Hz, 1H), 7.49 (s, 1H), 7.31-7.27 (m, 1H), 7.01 (d, J=4.8 Hz, 1H), 6.45-6.33 (m, 2H), 6.13 (d, J=8.4 Hz, 1H), 5.68 (dd, J=2.9, 8.4 Hz, 1H), 5.21 (t, J=3.7 Hz, 1H), 4.47-4.36 (m, 1H), 3.01-2.91 (m, 1H), 2.35 (dd, J=4.0, 17.2 Hz, 1H), 1.94 (br. s., 1H), 1.89-1.79 (m, 1H), 1.77-1.58 (m, 1H), 1.56-1.37 (m, 1H)

ESI-MS m/z 363 (MH$^+$)

Example 39

N-(3-(3-(6-Aminopyridin-3-yl)-1H-pyrrolo[2,3-b]pyridin-4-yl)cyclohex-3-en-1-yl)acrylamide (Compound 39)

The title compound was obtained in accordance with Example 28(2), with the exception that (6-aminopyridin-3-yl)boronic acid was used instead of the 1-methyl-4-(4,4,5,5-tetramethyl-1,3,2-dioxaborolan-2-yl)-1H-pyrazole.

$^1$H NMR (DMSO-d$_6$) δ: 11.79 (d, J=2.2 Hz, 1H), 8.18 (d, J=5.1 Hz, 1H), 8.03 (d, J=7.3 Hz, 1H), 7.85 (d, J=2.6 Hz, 1H), 7.44 (d, J=2.6 Hz, 1H), 7.26 (dd, J=2.6, 8.4 Hz, 1H), 6.89 (d, J=5.1 Hz, 1H), 6.44 (d, J=8.4 Hz, 1H), 6.26 (dd, J=10.3, 17.2 Hz, 1H), 6.08 (dd, J=2.2, 17.2 Hz, 1H), 5.83 (s, 2H), 5.57 (dd, J=2.2, 10.3 Hz, 1H), 5.22 (br. s., 1H), 4.01-3.81 (m, 1H), 2.58-2.52 (m, 1H), 2.28-2.14 (m, 1H), 1.96-1.66 (m, 3H), 1.53-1.32 (m, 1H)

ESI-MS m/z 360 (MH$^+$)

Example 40

N-(3-(3-(6-(Difluoromethoxy) pyridin-3-yl)-1H-pyrrolo[2,3-b]pyridin-4-yl)cyclohex-3-en-1-yl)acrylamide (Compound 40)

The title compound was obtained in accordance with Example 28(2), with the exception that 2-(difluoromethoxy)-5-(4,4,5,5-tetramethyl-1,3,2-dioxaborolan-2-yl)pyridine was used instead of the 1-methyl-4-(4,4,5,5-tetramethyl-1,3,2-dioxaborolan-2-yl)-1H-pyrazole.

$^1$H NMR (CDCl$_3$) δ: 11.77 (br. s., 1H), 8.31 (d, J=5.1 Hz, 1H), 8.11 (d, J=2.6 Hz, 1H), 7.70 (dd, J=2.6, 8.2 Hz, 1H), 7.67-7.28 (m, 2H), 6.96-6.92 (m, 2H), 6.32 (dd, J=1.5, 16.9 Hz, 1H), 6.18 (dd, J=10.1, 16.9 Hz, 1H), 5.88 (d, J=8.2 Hz, 1H), 5.65 (dd, J=1.5, 10.1 Hz, 1H), 5.35 (br. s., 1H), 4.29-4.11 (m, 1H), 2.73-2.68 (m, 1H), 2.39 (br. s., 1H), 2.19-2.07 (m, 1H), 2.06-1.91 (m, 1H), 1.88-1.73 (m, 1H), 1.60-1.40 (m, 1H)

ESI-MS m/z 411 (MH$^+$)

Example 41

N-(3-(3-(2-(Difluoromethoxy) pyridin-3-yl)-1H-pyrrolo[2,3-b]pyridin-4-yl)cyclohex-3-en-1-yl)acrylamide (Compound 41)

The title compound was obtained in accordance with Example 28(2), with the exception that 2-(difluoromethoxy)-3-(4,4,5,5-tetramethyl-1,3,2-dioxaborolan-2-yl)pyridine was used instead of the 1-methyl-4-(4,4,5,5-tetramethyl-1,3,2-dioxaborolan-2-yl)-1H-pyrazole.

$^1$H NMR (CDCl$_3$) δ: 10.35 (br. s., 1H), 8.30 (d, J=5.1 Hz, 1H), 8.17 (dd, J=1.8, 4.8 Hz, 1H), 7.67 (dd, J=1.8, 7.3 Hz, 1H), 7.65-7.27 (m, 1H), 7.19 (dd, J=4.8, 7.3 Hz, 1H), 6.96 (d, J=5.1 Hz, 1H), 6.30 (dd, J=1.5, 16.9 Hz, 1H), 6.11 (dd, J=10.3, 16.9 Hz, 1H), 5.65 (dd, J=1.5, 10.3 Hz, 1H), 5.49 (d, J=8.1 Hz, 1H), 5.35 (br. s., 1H), 4.14-4.04 (m, 1H), 2.72 (dd, J=4.8, 17.2 Hz, 1H), 2.53-2.27 (m, 1H), 2.27-2.12 (m, 1H), 2.10-1.94 (m, 1H), 1.92-1.67 (m, 1H), 1.45-1.33 (m, 1H)

ESI-MS m/z 411 (MH$^+$)

Example 42

N-(3-(3-(2-Aminopyridin-3-yl)-1H-pyrrolo[2,3-b]pyridin-4-yl)cyclohex-3-en-1-yl)acrylamide (Compound 42)

The title compound was obtained in accordance with Example 28(2), with the exception that (2-aminopyridin-3-yl)boronic acid was used instead of the 1-methyl-4-(4,4,5,5-tetramethyl-1,3,2-dioxaborolan-2-yl)-1H-pyrazole.

$^1$H NMR (CDCl$_3$) δ: 9.50 (br. s., 1H), 8.31 (d, J=5.1 Hz, 1H), 8.07 (dd, J=1.6, 4.9 Hz, 1H), 7.46 (d, J=5.5 Hz, 1H), 7.34 (s, 1H), 6.95 (d, J=5.1 Hz, 1H), 6.77 (t, J=5.7 Hz, 1H), 6.37 (d, J=16.5 Hz, 1H), 5.69 (d, J=11.7 Hz, 1H), 5.35 (br. s., 1H), 4.58-4.09 (m, 2H), 2.91 (br. s., 1H), 2.35-2.28 (m, 1H), 1.92-1.75 (m, 1H), 1.54-1.33 (m, 3H)

ESI-MS m/z 360 (MH$^+$)

Example 43

3-(4-(5-Acrylamidecyclohex-1-en-1-yl)-1H-pyrrolo[2,3-b]pyridin-3-yl)pyridine 1-oxide (Compound 43)

DMF (1.5 mL) was added to the Compound 28(1) (100 mg) and 3-(tributylstannyl)pyridine 1-oxide (100 mg), followed by nitrogen substitution. Thereafter, PdCl$_2$(PPh$_3$) (12.8 mg) was added to the reaction mixture, and the obtained mixture was then stirred under heating at 100° C. for 6 hours. Thereafter, the reaction mixture was cooled to a room temperature, and a saturated aqueous solution of sodium hydrogen carbonate and chloroform were then added to the reaction mixture. Thus obtained mixture was stirred, and was then filtered through Celite. The filtrate was extracted with chloroform, and the gathered organic layer was then washed with a saturated saline, dried over anhydrous sodium sulfate, and then concentrated under a reduced pressure. The obtained residue was purified by silica gel chromatography (chloroform:methanol) to obtain a corresponding coupling product. The obtained coupling product was subjected to the subsequent reaction without further purification.

THF (0.8 mL) and a THF solution (0.8 mL) of 1.0 M tetrabutylammonium fluoride were added to the obtained coupling product, and the obtained mixture was then stirred at a room temperature for 1 hour. Thereafter, a 0.067 M phosphate buffer (pH 7.4) was added to the reaction mixture, and the obtained mixture was then extracted with chloroform. The gathered organic layer was washed with a saturated saline, dried over anhydrous sodium sulfate, and then concentrated under a reduced pressure. The obtained residue was purified by silica gel chromatography (chloroform:methanol) to obtain the title compound (4.3 mg, yield: 7%).

$^1$H NMR (CDCl$_3$-CD$_3$OD) δ: 8.35-8.03 (m, 3H), 7.57-7.36 (m, 3H), 7.04 (t, J=4.9 Hz, 1H), 6.36-6.17 (m, 2H), 5.69-5.54 (m, 1H), 5.44-5.28 (m, 1H), 4.43-4.18 (m, 1H), 2.93-2.73 (m, 1H), 2.30-1.74 (m, 4H), 1.65-1.45 (m, 1H)

ESI-MS m/z 361 (MH$^+$)

Example 44

4-(4-(5-Acrylamidecyclohex-1-en-1-yl)-1H-pyrrolo[2,3-b]pyridin-3-yl)pyridine 1-oxide (Compound 44)

The title compound was obtained in accordance with Example 43, with the exception that 4-(tributylstannyl)pyridine 1-oxide was used instead of the 3-(tributylstannyl)pyridine 1-oxide.

$^1$H NMR (CDCl$_3$-CD$_3$OD) δ: 8.35-8.15 (m, 3H), 7.54 (s, 1H), 7.46-7.33 (m, 2H), 7.03 (d, J=5.1 Hz, 1H), 6.27 (dd, J=2.0, 17.1 Hz, 1H), 6.18 (dd, J=9.8, 17.1 Hz, 1H), 5.64 (dd, J=2.0, 9.8 Hz, 1H), 5.59-5.53 (m, 1H), 4.19-3.96 (m, 1H), 2.80-2.56 (m, 1H), 2.26-1.79 (m, 5H)

ESI-MS m/z 361 (MH$^+$)

Example 45

Example 45(1)

4-Chloro-3-iodo-1-tosyl-1H-pyrrolo[2,3-b]pyridine-5-carbonitrile (Compound 45(1))

DMF (9 mL) and potassium hydroxide (589 mg) were added to 4-chloro-1H-pyrrolo[2,3-b]pyridine-5-carbonitrile (533 mg), and the obtained mixture was then stirred at a room temperature for 20 minutes. Thereafter, iodine (1.14 g) was added to the reaction mixture, and the obtained mixture was further stirred at a room temperature for 2 hours. Thereafter, a saturated aqueous solution of sodium hydrogen carbonate was added to the reaction mixture for dilution, and the obtained mixture was then extracted with ethyl acetate. The gathered organic layer was washed with a 10% aqueous solution of sodium thiosulfate, and then with a saturated saline, and dried over anhydrous sodium sulfate, followed by vacuum concentration, to obtain a corresponding iodine product. The obtained iodine product was subjected to the subsequent reaction without further purification.

DMF (9 mL) was added to the obtained iodine product, and the obtained mixture was then cooled to 0° C. Thereafter, 60% sodium hydride (144 mg) was added to the reaction mixture. Thus obtained mixture was stirred at a room temperature for 10 minutes, and para-toluenesulfonyl chloride (858 mg) was then added to the reaction mixture at 0° C. The obtained mixture was stirred at a room temperature for 2 hours. Thereafter, a saturated aqueous solution of ammonium chloride was added to the reaction mixture, and the precipitated solid was collected by filtration and was then washed with ethyl acetate and water to obtain a product of interest (767 mg, yield: 56%)

$^1$H NMR (CDCl$_3$) δ: 8.59 (s, 1H), 8.09-8.06 (m, 3H), 7.34 (d, J=8.0 Hz, 2H), 2.41 (s, 3H)

ESI-MS m/z 458 (MH$^+$)

Example 45(2)

4-Chloro-3-(furan-2-yl)-1-tosyl-1H-pyrrolo[2,3-b]pyridine-5-carbonitrile (Compound 45(2))

DMF (10 mL) was added to the Compound 45(1) (458 mg) and tributyl(furan-2-yl)stannane (0.35 mL), followed by nitrogen substitution. Thereafter, PdCl$_2$(PPh$_3$) (35 mg) was added to the reaction mixture, and the temperature of the obtained mixture was then increased to 100° C., followed by stirring for 15 hours. Thereafter, a saturated aqueous solution of ammonium chloride was added to the reaction mixture for dilution, and the obtained mixture was then extracted with ethyl acetate. The gathered organic layer was washed with water, with a saturated aqueous solution of sodium hydrogen carbonate and with a saturated saline, and dried over anhydrous sodium sulfate, followed by vacuum concentration. The obtained residue was purified by silica gel chromatography (hexane:ethyl acetate) to obtain a product of interest (348 mg, yield: 88%).

$^1$H NMR (CDCl$_3$) δ: 8.62 (s, 1H), 8.10 (d, J=8.5 Hz, 2H), 8.08 (s, 1H), 7.55 (dd, J=0.7, 1.7 Hz, 1H), 7.34 (d, J=8.5 Hz, 2H), 6.69 (dd, J=0.7, 3.4 Hz, 1H), 6.52 (dd, J=1.7, 3.4 Hz, 1H), 2.42 (s, 3H)

ESI-MS m/z 398 (MH$^+$)

Example 45(3)

N-(3-(5-Cyano-3-(furan-2-yl)-1H-pyrrolo[2,3-b]pyridin-4-yl)cyclohex-3-en-1-yl)acrylamide (Compound 45)

1,4-Dioxane (3.0 mL) and water (0.5 mL) were added to the Compound 45(2) (80 mg), the compound of Reference Example 1(2a) (156 mg) and tripotassium phosphate (175 mg), followed by nitrogen substitution. Thereafter, PdCl$_2$(dppf)CH$_2$Cl$_2$ (24.0 mg) was added to the reaction mixture, and the obtained mixture was then stirred at 100° C. for 1 hour. Thereafter, the reaction mixture was cooled to a room temperature, and ethyl acetate and water were then added to the mixture. Thus obtained mixture was then filtered through Celite. The filtrate was extracted with ethyl acetate, and the gathered organic layer was washed with water and then with a saturated saline. The resultant was dried over anhydrous sodium sulfate, and then concentrated under a reduced pressure.

THF (1 mL) and a THF solution (1 mL) of 1.0 M tetrabutylammonium fluoride were added to the obtained residue, and the obtained mixture was then stirred at a room temperature for 1 hour, followed by vacuum concentration. A 0.067 M phosphate buffer (pH 7.4) was added to the residue, and the obtained mixture was then extracted with ethyl acetate. The gathered organic layer was washed with a saturated saline, dried over anhydrous sodium sulfate, and then concentrated under a reduced pressure. The obtained residue was purified by silica gel chromatography (chloroform:methanol) to obtain a corresponding coupling product. The obtained coupling product was subjected to the subsequent reaction without further purification.

Methanol (1 mL) and a 1,4-dioxane solution (1 mL) of 4 M hydrochloric acid were added to the obtained coupling body, and the obtained mixture was then stirred at a room temperature for 30 minutes. Thereafter, the reaction mixture was concentrated under a reduced pressure. Under a nitrogen atmosphere, dichloromethane (3 mL) and diisopropylethylamine (0.3 mL) were added to the reaction mixture, and the obtained mixture was then cooled to 0° C. Thereafter, acryloyl chloride (0.03 mL) was added to the reaction mixture, and the obtained mixture was then stirred for 20 minutes. An ammonia aqueous solution, chloroform and methanol were successively added to the reaction mixture, and thus obtained mixture was then stirred at a room temperature for 1 hour. Thereafter, the reaction mixture was extracted with chloroform, and the gathered organic layer was washed with a saturated saline, dried over anhydrous sodium sulfate, and then concentrated under a reduced pressure. The obtained residue was purified by silica gel chromatography (chloroform:methanol) to obtain the title compound (52.2 mg, yield: 44%).

$^1$H NMR (CDCl$_3$-CD$_3$OD) δ: 8.51 (s, 1H), 7.63-7.53 (m, 2H), 6.50 (dd, J=2.0, 3.2 Hz, 1H), 6.41 (dd, J=0.7, 3.2 Hz, 1H), 6.28 (dd, J=1.7, 17.1 Hz, 1H), 6.16 (dd, J=10.2, 17.1 Hz, 1H), 5.78-5.70 (m, 1H), 5.65 (dd, J=1.7, 10.2 Hz, 1H), 4.38-4.26 (m, 1H), 2.68-2.53 (m, 1H), 2.36-2.07 (m, 3H), 1.91-1.72 (m, 2H)

ESI-MS m/z 359 (MH$^+$)

Example 46

N-(3-(5-Cyano-3-(furan-2-yl)-1H-pyrrolo[2,3-b]pyridin-4-yl)cyclopent-3-en-1-yl)acrylamide (Compound 46)

The title compound was obtained in accordance with Example 45(3), with the exception that the compound of Reference Example 2(2a) was used instead of the compound of Reference Example 1(2a).

$^1$H NMR (CDCl$_3$-CD$_3$OD) δ: 8.53 (s, 1H), 7.61-7.46 (m, 2H), 6.50-6.42 (m, 1H), 6.39-6.06 (m, 3H), 5.78-5.60 (m, 2H), 4.77-4.62 (m, 1H), 3.08-2.68 (m, 2H), 2.67-2.37 (m, 2H)

ESI-MS m/z 345 (MH$^+$)

Example 47

Example 47(1)

4-Chloro-1-tosyl-1H-pyrrolo[2,3-b]pyridine-3-carbaldehyde (Compound 47(1))

DMF (50 mL) was added to 4-chloro-1H-pyrrolo[2,3-b]pyridine-3-carbaldehyde (1.81 g), and the obtained mixture was then cooled to 0° C. Thereafter, 60% sodium hydride (1.2 g) was added to the reaction mixture, and the obtained mixture was then stirred for 30 minutes. Thereafter, para-toluenesulfonyl chloride (3.43 g) was added to the reaction mixture, and the obtained mixture was then stirred for 1 hour. Thereafter, ice and water were successively added to the reaction mixture, and the obtained mixture was then stirred for 30 minutes. Thereafter, the reaction mixture was filtered, and the residue was then washed with water to obtain a product of interest (3.28 g, yield: 98%).

ESI-MS m/z 335 (MH$^+$)

Example 47(2)

tert-Butyl (3-(3-formyl-1-tosyl-1H-pyrrolo[2,3-b]pyridin-4-yl)cyclohex-3-en-1-yl)carbamate (Compound 47(2))

1,4-Dioxane (44 mL) and a 2 M aqueous solution of sodium carbonate (6.57 mL) were added to the Compound 47(1) (2.20 g), the compound of Reference Example 1(2a) (2.34 g) and Pd(PPh$_3$)$_4$ (1.14 mg), followed by nitrogen substitution. Thereafter, the reaction mixture was stirred at 100° C. for 10 hours. Thereafter, water was added to the reaction mixture, and the obtained mixture was then extracted with ethyl acetate. The gathered organic layer was washed with a saturated saline, dried over anhydrous sodium sulfate, and then concentrated under a reduced pressure. The obtained residue was purified by silica gel chromatography (hexane:ethyl acetate) to obtain a product of interest (2.05 g, yield: 63%).

ESI-MS m/z 496 (MH$^+$)

Example 47(3)

4-(5-((tert-Butoxycarbonyl)amino)cyclohex-1-en-1-yl)-1-tosyl-1H-pyrrolo[2,3-b]pyridine-3-carboxylic acid (Compound 47(3))

A tert-butanol solution (25 mL) and 2-methyl-2-butene (1.71 mL) were added to the Compound 47(2) (1.0 g), and an aqueous solution (10 mL) of sodium chlorite (1.37 g) and sodium dihydrogen phosphate (970 mg) was then added to the above mixture under cooling on ice. Thus obtained mixture was stirred for 1.5 hours. Thereafter, the reaction mixture was concentrated under a reduced pressure, and was then extracted with chloroform. The gathered organic layer was washed with a saturated saline, dried over anhydrous sodium sulfate, and then concentrated under a reduced pressure. The obtained residue was purified by silica gel chromatography (hexane:ethyl acetate) to obtain a product of interest (1.09 g, yield: 99%).

ESI-MS m/z 512 (MH$^+$)

Example 47(4)

tert-Butyl (3-(3-(1,2,4-oxadiazol-5-yl)-1-tosyl-1H-pyrrolo[2,3-b]pyridin-4-yl)cyclohex-3-en-1-yl)carbamate (Compound 47(4))

DMF (10 mL), HATU (1.48 g) and diisopropylethylamine (0.66 mL) were added to the Compound 47(3) (500 mg), and the obtained mixture was then stirred for 10 minutes. Thereafter, ammonia water (0.81 mL) was added to the reaction mixture, and thus obtained mixture was then stirred for 5 minutes. Thereafter, a saturated aqueous solution of sodium hydrogen carbonate was added to the reaction mixture, and the obtained mixture was then extracted with ethyl acetate. The gathered organic layer was successively washed with water and a saturated saline, and dried over anhydrous sodium sulfate, followed by vacuum concentration. The obtained residue was purified by silica gel chromatography (methanol:chloroform) to obtain a corresponding carbamoyl product (380 mg, yield: 78%).

N,N-Dimethylformamidedimethylacetal (3 mL) was added to the obtained carbamoyl product, and the obtained mixture was then stirred at 80° C. for 40 minutes. Thereafter, the reaction mixture was concentrated under a reduced pressure. A 1 M aqueous solution of sodium hydroxide (0.28 mL), hydroxyamine hydrochloride (20 mg) and acetic acid (1.8 mL) were added to the obtained residue, and the obtained mixture was then stirred at a room temperature for 20 hours, and was further stirred at 60° C. for 4 hours. Subsequently, the reaction mixture was stirred at a room temperature for 15 hours. Thereafter, the reaction mixture was concentrated under a reduced pressure, and the obtained residue was purified by silica gel chromatography (hexane:ethyl acetate) to obtain a product of interest (32 mg, yield: 20%).

ESI-MS m/z 536 (MH$^+$)

Example 47(5)

N-(3-(3-(1,2,4-Oxadiazol-5-yl)-1H-pyrrolo[2,3-b]pyridin-4-yl)cyclohex-3-en-1-yl)acrylamide (Compound 47)

Dichloromethane (1 mL) and TFA (0.30 mL) were added to the Compound 47(4) (27 mg), and the obtained mixture was then stirred at a room temperature for 20 minutes. Thereafter, the reaction mixture was concentrated under a reduced pressure. Diisopropylethylamine (25 µL) was added to an ethanol solution (1 mL) of the obtained residue, and the obtained mixture was then cooled to 0° C. Subsequently, acryloyl chloride (5 µL) was added to the reaction mixture, and the obtained mixture was then stirred for 10 minutes. Thereafter, a saturated saline was added to the reaction mixture, and the obtained mixture was then extracted with chloroform. The extract was dried over anhydrous sodium sulfate, and then concentrated under a reduced pressure. The obtained residue was purified by silica gel chromatography (chloroform:methanol) to obtain a corresponding acrylamide product. The obtained acrylamide product was subjected to the subsequent reaction without further purification. THF (0.5 mL), methanol (0.5 mL) and a 2 M aqueous solution of sodium hydroxide (0.3 mL) were successively added to the obtained acrylamide product, and the obtained mixture was then stirred at a room temperature for 1 hour. Thereafter, a saturated aqueous solution of ammonium chloride was added to the reaction mixture, and the obtained mixture was then extracted with chloroform. The extract was dried over anhydrous sodium sulfate, and then concentrated under a reduced pressure. The obtained residue was purified by preparatory thin-layer chromatography (chloroform:methanol) to obtain the title compound (2 mg, yield: 12%).

$^1$H NMR (DMSO-$d_6$) δ: 12.59 (br. s., 1H), 11.71 (br. s., 1H), 8.28 (d, J=5.1 Hz, 1H), 8.23 (d, J=2.9 Hz, 1H), 8.15 (d, J=6.6 Hz, 1H), 7.01 (d, J=5.1 Hz, 1H), 6.30 (dd, J=10.1, 17.0 Hz, 1H), 6.10 (dd, J=2.2, 17.0 Hz, 1H), 5.59-5.54 (m, 2H), 4.16-4.07 (m, 1H), 2.58 (dd, J=4.0, 16.5 Hz, 1H), 2.22 (br. s., 3H), 1.87-1.80 (m, 1H), 1.38-1.31 (m, 1H)

ESI-MS m/z 336 (MH$^+$)

Example 48

Example 48(1)

4-Chloro-1-((2-(trimethylsilyl)ethoxy)methyl)-1H-pyrrolo[2,3-b]pyridine-3-carbaldehyde (Compound 48(1))

DMF (78 mL) was added to 4-chloro-1H-pyrrolo[2,3-b]pyridine-3-carbaldehyde (1.41 g), and the obtained mixture was then cooled to 0° C. Thereafter, 60% sodium hydride (625 mg) was added to the reaction mixture, and the obtained mixture was then stirred for 30 minutes. Thereafter, 2-(chloromethoxy)ethyltrimethylsilane (2.07 mL) was added to the reaction mixture, and the obtained mixture was then stirred for 1 hour. Thereafter, a saturated aqueous solution of ammonium chloride was added to the reaction mixture, and the obtained mixture was then extracted with ethyl acetate. The gathered organic layer was successively washed with water and with a saturated saline, and dried over anhydrous sodium sulfate, followed by vacuum concentration. The obtained residue was purified by silica gel chromatography (hexane:ethyl acetate) to obtain a product of interest (2.03 g, yield: 84%).

ESI-MS m/z 311 (MH$^+$)

Example 48(2)

tert-Butyl (3-(3-formyl-1-((2-(trimethylsilyl)ethoxy)methyl)-1H-pyrrolo[2,3-b]pyridin-4-yl)cyclohex-3-en-1-yl)carbamate (Compound 48(2))

1,4-Dioxane (15 mL) and a 2 M aqueous solution of sodium carbonate (4.5 mL) were added to the Compound 48(1) (1.4 g), the compound of Reference Example 1(2a) (2.19 g) and Pd(PPh$_3$)$_4$ (520 mg). Under a nitrogen atmosphere, the mixture was stirred at 90° C. for 14 hours. Thereafter, water was added to the reaction mixture, and the obtained mixture was then extracted with ethyl acetate. The gathered organic layer was washed with a saturated saline, dried over anhydrous sodium sulfate, and then concentrated under a reduced pressure. The obtained residue was purified by silica gel chromatography (hexane:ethyl acetate) to obtain a product of interest (1.78 g, yield: 84%).

$^1$H NMR (CDCl$_3$) δ: 10.06 (s, 1H), 8.35 (d, J=4.8 Hz, 1H), 8.09 (s, 1H), 7.03 (d, J=4.8 Hz, 1H), 5.81 (s, 1H), 5.74 (s, 2H), 5.37 (br. s., 1H), 4.10-4.02 (m, 1H), 3.61 (dd, J=7.7, 8.8 Hz, 2H), 2.82-2.65 (m, 1H), 2.47-2.21 (m, 3H), 1.98-1.76 (m, 2H), 1.47 (s, 9H), 0.98-0.89 (m, 2H), −0.03 (s, 6H)

ESI-MS m/z 472 (MH$^+$)

Example 48(3)

tert-Butyl (3-(3-(oxazol-5-yl)-1-((2-(trimethylsilyl)ethoxy)methyl)-1H-pyrrolo[2,3-b]pyridin-4-yl)cyclohex-3-en-1-yl)carbamate (Compound 48(3))

Methanol (2.5 mL), p-toluenesulfonylmethylisocyanide (65 mg) and potassium carbonate (46 mg) were added to the Compound 48(2) (120 mg), and the obtained mixture was then stirred under heating to reflux for 28 hours. Thereafter, the reaction mixture was concentrated under a reduced pressure, and the obtained residue was purified by silica gel chromatography (hexane:ethyl acetate) to obtain a product of interest (54 mg, yield: 42%).

$^1$H NMR (CDCl$_3$) δ: 8.35 (d, J=4.8 Hz, 1H), 8.00 (s, 1H), 7.57 (s, 1H), 7.08 (s, 1H), 6.98 (d, J=4.8 Hz, 1H), 5.73 (s, 2H), 5.53 (br. s., 1H), 4.71 (br. s., 1H), 3.95 (br. s., 1H), 3.64-3.58 (m, 2H), 2.76 (d, J=16.9 Hz, 1H), 2.25-1.99 (m, 3H), 1.93-1.79 (m, 1H), 1.62 (d, J=7.0 Hz, 1H), 1.47 (s, 9H), 0.98-0.91 (m, 2H), −0.04 (s, 9H)

ESI-MS m/z 511 (MH$^+$)

Example 48(4)

N-(3-(3-(Oxazol-5-yl)-1H-pyrrolo[2,3-b]pyridin-4-yl)cyclohex-3-en-1-yl)acrylamide (Compound 48)

THF (2 mL) and a THF solution (1 mL) of 1.0 M tetrabutylammonium fluoride were added to the Compound 48(3) (52 mg), and the obtained mixture was then stirred at 60° C. for 21 hours. Thereafter, a 0.067 M phosphate buffer (pH 7.4) was added to the reaction mixture, and the obtained mixture was then extracted with ethyl acetate. The gathered organic layer was washed with a saturated saline, dried over anhydrous sodium sulfate, and then concentrated under a reduced pressure. The obtained residue was purified by silica gel chromatography (hexane:ethyl acetate) to obtain a corresponding protective group-removed product. The obtained protective group-removed product was subjected to the subsequent reaction without further purification.

A methanol solution (2 mL) and a 1,4-dioxane solution (1 mL) of 4 M hydrochloric acid were added to the obtained protective group-removed product, and the obtained mixture was then stirred at a room temperature for 1 hour. Thereafter, the reaction mixture was concentrated under a reduced pressure. Diisopropylethylamine (0.15 mL) was added to a dichloromethane solution (3 mL) of the obtained residue, and thus obtained mixture was then cooled to 0° C. Acryloyl chloride (15 µL) was added to the reaction mixture, and the obtained mixture was then stirred for 30 minutes. Thereafter, an ammonia aqueous solution was added to the reaction mixture, and the obtained mixture was then stirred at a room temperature for 2 hours. Thereafter, the reaction mixture was extracted with chloroform, and the gathered organic layer was washed with a saturated saline, dried over anhydrous sodium sulfate, and then concentrated under a reduced pressure. The obtained residue was purified by silica gel chromatography (chloroform:methanol) to obtain the title compound (13 mg, yield: 38%).

$^1$H NMR (CDCl$_3$) δ: 8.29 (d, J=4.8 Hz, 1H), 7.97 (s, 1H), 7.56 (s, 1H), 7.05 (s, 1H), 6.96 (d, J=4.8 Hz, 1H), 6.31 (dd, J=1.5, 16.9 Hz, 1H), 6.13 (dd, J=9.9, 16.9 Hz, 1H), 5.91-5.81 (m, 1H), 5.66 (dd, J=1.5, 9.9 Hz, 1H), 5.60 (br. s, 1H), 4.34-4.26 (m, 1H), 2.75 (d, J=18.7 Hz, 1H), 2.24-2.04 (m, 3H), 2.00-1.82 (m, 1H), 1.68-1.54 (m, 1H)

ESI-MS m/z 335 (MH$^+$)

Example 49

Example 49(1)

4-(5-((tert-Butoxycarbonyl)amino)cyclohex-1-en-1-yl)-1-((2-(trimethylsilyl)ethoxy)methyl)-1H-pyrrolo[2,3-b]pyridine-3-carboxylic acid (Compound 49(1))

tert-Butanol (30 mL) and 2-methyl-2-butene (5.4 mL) were added to the Compound 48(2) (1.24 g), and an aqueous solution (12 mL) of sodium chlorite (2.88 g) and sodium dihydrogen phosphate (2.23 g) was then added to the above mixture under cooling on ice. Thus obtained mixture was stirred for 1.5 hours. Thereafter, the reaction mixture was concentrated under a reduced pressure, and was then extracted with chloroform. The gathered organic layer was washed with a saturated saline, dried over anhydrous sodium sulfate, and then concentrated under a reduced pressure. The obtained residue was purified by silica gel chromatography (hexane:ethyl acetate) to obtain a product of interest (1.15 g, yield: 90%).

$^1$H NMR (DMSO-d$_6$) δ: 12.18 (s, 1H), 8.31 (s, 1H), 8.28 (d, J=4.8 Hz, 1H), 6.99 (d, J=4.8 Hz, 1H), 6.80 (d, J=7.7 Hz, 1H), 5.67 (s, 2H), 5.54-5.50 (m, 1H), 3.87-3.67 (m, 1H), 3.60-3.50 (m, 2H), 2.47-2.34 (m, 1H), 2.24-2.08 (m, 3H), 1.97-1.77 (m, 1H), 1.62-1.42 (m, 1H), 1.40-1.35 (m, 9H), 0.85-0.79 (m, 2H), −0.09-−0.11 (m, 9H)

ESI-MS m/z 488 (MH$^+$)

Example 49(2)

tert-Butyl (3-(3-(hydrazinecarbonyl)-1-((2-(trimethylsilyl)ethoxy)methyl)-1H-pyrrolo[2,3-b]pyridin-4-yl)cyclohex-3-en-1-yl)carbamate (Compound 49(2))

DMF (6 mL), HATU (975 mg) and diisopropylethylamine (0.15 mL) were added to the Compound 49(1) (300 mg), and the obtained mixture was then stirred for 10 minutes. Thereafter, hydrazine monohydrate (0.18 mL) was added to the reaction mixture, and the obtained mixture was then stirred for 15 minutes. Thereafter, a saturated aqueous solution of sodium hydrogen carbonate was added to the reaction mixture, and the obtained mixture was then extracted with ethyl acetate. The gathered organic layer was successively washed with water and with a saturated saline, and dried over anhydrous sodium sulfate, followed by vacuum concentration. The obtained residue was purified by silica gel chromatography (chloroform:methanol) to obtain a product of interest (283 mg, yield: 92%).

$^1$H NMR (CDCl$_3$) δ: 8.32 (d, J=4.8 Hz, 1H), 7.84 (s, 1H), 7.44 (br. s., 1H), 6.96 (d, J=4.8 Hz, 1H), 5.91 (br. s., 1H), 5.69 (s, 2H), 5.65-5.56 (m, 1H), 4.51-4.20 (m, 2H), 4.09-4.00 (m, 1H), 3.60-3.54 (m, 2H), 2.80-2.52 (m, 1H), 2.43-2.23 (m, 2H), 2.20-2.09 (m, 1H), 1.89-1.79 (m, 2H), 1.46 (s, 9H), 0.97-0.88 (m, 2H), −0.05 (s, 9H)

ESI-MS m/z 502 (MH$^+$)

Example 49(3)

tert-Butyl (3-(3-(1,3,4-oxadiazol-2-yl)-1-((2-(trimethylsilyl)ethoxy)methyl)-1H-pyrrolo[2,3-b]pyridin-4-yl)cyclohex-3-en-1-yl)carbamate (Compound 49(3))

Triethyl orthoformate (2 mL) was added to the Compound 49(2) (283 mg), and the obtained mixture was then stirred under heating to reflux for 1.5 hours. Thereafter, the reaction mixture was concentrated under a reduced pressure, and the obtained residue was then purified by silica gel chromatography (methanol:chloroform) to obtain a product of interest (250 mg, yield: 87%).

$^1$H NMR (CDCl$_3$) δ: 8.50 (s, 1H), 8.38 (d, J=5.1 Hz, 1H), 8.03 (s, 1H), 7.04 (d, J=5.1 Hz, 1H), 5.77 (s, 2H), 5.57-5.47 (m, 2H), 4.15-4.03 (m, 1H), 3.64-3.58 (m, 2H), 2.92-2.78 (m, 1H), 2.36-2.26 (m, 1H), 2.17-2.09 (m, 2H), 1.90-1.70 (m, 2H), 1.50-1.44 (m, 9H), 0.98-0.88 (m, 2H), −0.04 (s, 9H)

ESI-MS m/z 512 (MH$^+$)

Example 49(4)

N-(3-(3-(1,3,4-Oxadiazol-2-yl)-1H-pyrrolo[2,3-b]pyridin-4-yl)cyclohex-3-en-1-yl)acrylamide (Compound 49)

THF (5 mL) and a THF solution (3 mL) of 1 M tetrabutylammonium fluoride were added to the Compound 49(3) (240 mg), and the obtained mixture was then stirred at 60° C. for 16 hours. Thereafter, a 0.067 M phosphate buffer (pH 7.4) was added to the reaction mixture, and the obtained mixture was then extracted with ethyl acetate. The gathered organic layer was washed with a saturated saline, dried over anhydrous sodium sulfate, and then concentrated under a reduced pressure. The obtained residue was purified by silica gel chromatography (methanol:chloroform) to obtain a corresponding protective group-removed product. The obtained protective group-removed product was subjected to the subsequent reaction without further purification.

Hexafluoroisopropanol (1.5 mL) was added to the obtained protective group-removed product, and the obtained mixture was then stirred in a microwave at 145° C. for 1.5 hours. Thereafter, the reaction mixture was concentrated under a reduced pressure. Diisopropylethylamine (0.11 mL) was added to an ethanol solution (4 mL) of the obtained residue, and the obtained mixture was then cooled to 0° C. Acryloyl chloride (32 μL) was added to the reaction mixture, and the obtained mixture was then stirred for 5 minutes. Thereafter, an ammonia aqueous solution was added to the reaction mixture, and the obtained mixture was then stirred at a room temperature for 5 minutes. Thereafter, the reaction mixture was extracted with chloroform, and the gathered organic layer was washed with a saturated saline, dried over anhydrous sodium sulfate, and then concentrated under a reduced pressure. The obtained residue was purified by silica gel chromatography (chloroform:methanol) to obtain the title compound (43 mg, yield: 28%).

$^1$H NMR (DMSO-d$_6$) δ: 12.64 (br. s., 1H), 9.29 (s, 1H), 8.31 (d, J=5.1 Hz, 1H), 8.21 (s, 1H), 8.19 (d, J=7.7 Hz, 1H), 7.05 (d, J=5.1 Hz, 1H), 6.34 (dd, J=10.3, 16.9 Hz, 1H), 6.10 (dd, J=2.2, 16.9 Hz, 1H), 5.58 (dd, J=2.2, 10.3 Hz, 1H), 5.42-5.36 (m, 1H), 4.16-4.04 (m, 1H), 2.71-2.58 (m, 1H), 2.30-2.20 (m, 1H), 2.07-1.99 (m, 2H), 1.86-1.75 (m, 1H), 1.65-1.51 (m, 1H)
ESI-MS m/z 336 (MH$^+$)

Example 50

N-(3-(3-(5-Methyl-1,3,4-oxadiazol-2-yl)-1H-pyrrolo[2,3-b]pyridin-4-yl)cyclohex-3-en-1-yl)acrylamide (Compound 50)

The title compound was obtained in accordance with Example 49, with the exception that triethyl orthoacetate was used instead of the triethyl orthoformate.
$^1$H NMR (CDCl$_3$) δ: 10.90 (br. s., 1H), 8.44 (d, J=8.8 Hz, 1H), 8.39 (d, J=5.1 Hz, 1H), 8.02 (s, 1H), 7.08 (d, J=5.1 Hz, 1H), 6.71 (dd, J=10.3, 16.9 Hz, 1H), 6.37 (dd, J=2.0, 16.9 Hz, 1H), 5.63-5.58 (m, 2H), 4.82-4.66 (m, 1H), 2.96 (tdd, J=2.3, 4.4, 17.0 Hz, 1H), 2.63 (s, 3H), 2.35 (d, J=17.2 Hz, 1H), 2.29-1.97 (m, 3H), 1.85-1.69 (m, 1H)
ESI-MS m/z 350 (MH$^+$)

Example 51

N-(3-(3-(5-Ethyl-1,3,4-oxadiazol-2-yl)-1H-pyrrolo[2,3-b]pyridin-4-yl)cyclohex-3-en-1-yl)acrylamide (Compound 51)

The title compound was obtained in accordance with Example 49, with the exception that triethyl orthopropionate was used instead of the triethyl orthoformate.
$^1$H NMR (CDCl$_3$) δ: 11.42 (br. s., 1H), 8.49 (d, J=8.4 Hz, 1H), 8.40 (d, J=5.1 Hz, 1H), 8.05 (s, 1H), 7.08 (d, J=5.1 Hz, 1H), 6.77 (dd, J=10.3, 16.9 Hz, 1H), 6.37 (dd, J=2.2, 16.9 Hz, 1H), 5.64-5.58 (m, 2H), 4.79-4.67 (m, 1H), 2.99-2.91 (m, 3H), 2.37 (d, J=17.2 Hz, 1H), 2.31-2.01 (m, 3H), 1.81-1.69 (m, 1H), 1.47 (t, J=7.5 Hz, 3H)
ESI-MS m/z 364 (MH$^+$)

Example 52

Example 52(1)

tert-Butyl (3-(3-(5-oxo-4,5-dihydro-1,3,4-oxadiazol-2-yl)-1-((2-(trimethylsilyl)ethoxy)methyl)-1H-pyrrolo[2,3-b]pyridin-4-yl)cyclohex-3-en-1-yl)carbamate (Compound 52(1))

THF (3 mL) was added to the Compound 49(2) (282 mg), and the obtained mixture was then cooled to 0° C. Carbonyldiimidazole (273 mg) and triethylamine (1 mL) were added to the reaction mixture, and the obtained mixture was then stirred at a room temperature for 2 hours. Thereafter, a saturated aqueous solution of sodium hydrogen carbonate was added to the reaction mixture, and the obtained mixture was then extracted with ethyl acetate. The gathered organic layer was washed with a saturated saline, dried over anhydrous sodium sulfate, and then concentrated under a reduced pressure. The obtained residue was purified by silica gel chromatography (methanol:chloroform) to obtain a product of interest (270 mg, yield: 91%).
$^1$H NMR (CDCl$_3$) δ: 10.76 (br. s., 1H), 9.15 (br. s., 1H), 8.37 (d, J=5.1 Hz, 1H), 7.97 (s, 1H), 7.44 (d, J=7.0 Hz, 1H), 7.01 (d, J=4.8 Hz, 1H), 6.44 (br. s., 1H), 5.74 (s, 2H), 5.59 (d, J=5.1 Hz, 1H), 4.28-3.88 (m, 1H), 3.63-3.57 (m, 2H), 2.93-2.74 (m, 1H), 2.53-1.87 (m, 4H), 1.54-1.46 (m, 10H), 0.95 (dd, J=7.5, 9.0 Hz, 2H), −0.04 (s, 9H)
ESI-MS m/z 528 (MH$^+$)

Example 52(2)

N-(3-(3-(5-Oxo-4,5-dihydro-1,3,4-oxadiazol-2-yl)-1H-pyrrolo[2,3-b]pyridin-4-yl)cyclohex-3-en-1-yl)acrylamide (Compound 52)

The title compound was obtained in accordance with Example 49(4), with the exception that the Compound 52(1) was used instead of the Compound 49(3).
$^1$H NMR (DMSO-d$_6$) δ: 12.49 (br. s., 1H), 12.29 (br. s., 1H), 8.28 (d, J=5.1 Hz, 1H), 8.10 (d, J=7.7 Hz, 1H), 8.05 (s, 1H), 7.03 (d, J=5.1 Hz, 1H), 6.26 (dd, J=10.6, 16.9 Hz, 1H), 6.09 (dd, J=1.8, 16.9 Hz, 1H), 5.64-5.50 (m, 2H), 4.16-3.98 (m, 1H), 2.60 (dd, J=4.9, 16.3 Hz, 1H), 2.31-2.08 (m, 3H), 1.95-1.80 (m, 1H), 1.68-1.53 (m, 1H)
ESI-MS m/z 352 (MH$^+$)

Example 53

Example 53(1)

tert-Butyl (3-(3-(4-methyl-5-oxo-4,5-dihydro-1,3,4-oxadiazol-2-yl)-1-((2-(trimethylsilyl)ethoxy)methyl)-1H-pyrrolo[2,3-b]pyridin-4-yl)cyclohex-3-en-1-yl)carbamate (Compound 53(1))

DMF (1.2 mL) and potassium carbonate (37 mg) were added to the Compound 52(1) (131 mg), and the obtained mixture was then stirred for 15 minutes. Thereafter, iodomethane (0.015 mL) was added to the reaction mixture, and the obtained mixture was then stirred at a room temperature for 20 minutes. Thereafter, water was added to the reaction mixture, and the obtained mixture was then extracted with ethyl acetate. The gathered organic layer was washed with a saturated saline, dried over anhydrous sodium sulfate, and then concentrated under a reduced pressure. The obtained residue was purified by silica gel chromatography (methanol:chloroform) to obtain a product of interest (120 mg, yield: 89%).
$^1$H NMR (CDCl$_3$) δ: 8.36 (d, J=4.8 Hz, 1H), 7.93 (s, 1H), 7.02 (d, J=4.8 Hz, 1H), 5.73 (s, 2H), 5.69-5.65 (m, 1H), 5.12 (d, J=8.8 Hz, 1H), 4.24-4.08 (m, 1H), 3.62-3.51 (m, 5H), 2.94-2.77 (m, 1H), 2.33-2.16 (m, 3H), 2.02-1.87 (m, 1H), 1.82-1.69 (m, 1H), 1.45 (s, 9H), 0.97-0.90 (m, 2H), −0.04 (s, 9H)
ESI-MS m/z 542 (MH$^+$)

Example 53(2)

N-(3-(3-(4-Methyl-5-oxo-4,5-dihydro-1,3,4-oxadiazol-2-yl)-1H-pyrrolo[2,3-b]pyridin-4-yl)cyclohex-3-en-1-yl)acrylamide (Compound 53)

The title compound was obtained in accordance with Example 49(4), with the exception that the Compound 53(1) was used instead of the Compound 49(3).
$^1$H NMR (DMSO-d$_6$) δ: 12.56 (br. s., 1H), 8.28 (d, J=4.8 Hz, 1H), 8.13-8.08 (m, 2H), 7.01 (d, J=4.8 Hz, 1H), 6.23 (dd, J=10.3, 17.2 Hz, 1H), 6.08 (dd, J=2.6, 17.2 Hz, 1H), 5.62-5.53 (m, 2H), 4.29-3.96 (m, 1H), 3.43 (s, 3H), 2.62-2.52 (m, 1H), 2.33-2.13 (m, 3H), 1.90-1.86 (m, 1H), 1.69-1.50 (m, 1H)
ESI-MS m/z 366 (MH$^+$)

Example 54

Example 54(1)

tert-Butyl (3-(3-(1,3,4-thiadiazol-2-yl)-1-((2-(trimethylsilyl)ethoxy)methyl)-1H-pyrrolo[2,3-b]pyridin-4-yl)cyclohex-3-en-1-yl)carbamate (Compound 54(1))

DMF (4 mL), HATU (624 mg) and diisopropylethylamine (0.28 mL) were added to the Compound 49(1) (200 mg), and the obtained mixture was then stirred for 10 minutes. Thereafter, formohydrazide (148 mg) was added to the reaction mixture, and the obtained mixture was then stirred for 30 minutes. Thereafter, a saturated aqueous solution of sodium hydrogen carbonate was added to the reaction mixture, and the obtained mixture was then extracted with ethyl acetate. The gathered organic layer was successively washed with water and a saturated saline, and dried over anhydrous sodium sulfate, followed by vacuum concentration. The obtained residue was purified by silica gel chromatography (chloroform:methanol) to obtain an acyl hydrazide product (166 mg, yield: 76%). THF (5 mL) and a Lawesson reagent (380 mg) were added to the obtained acyl hydrazide product, and the obtained mixture was then stirred at 60° C. for 2 hours. Thereafter, a saturated aqueous solution of sodium hydrogen carbonate was added to the reaction mixture. The obtained mixture was extracted with ethyl acetate, and dried over anhydrous sodium sulfate, followed by vacuum concentration. The obtained residue was purified by silica gel chromatography (methanol:chloroform) to obtain a product of interest (19 mg, yield: 12%).
ESI-MS m/z 528 (MH$^+$)

Example 54(2)

N-(3-(3-(1,3,4-Thiadiazol-2-yl)-1H-pyrrolo[2,3-b]pyridin-4-yl)cyclohex-3-en-1-yl)acrylamide (Compound 54)

THF (1 mL) and a THF solution (0.29 mL) of 1.0 M tetrabutylammonium fluoride were added to the Compound 54(1) (19 mg), and the obtained mixture was then stirred at 60° C. for 15 hours. Thereafter, a 0.067 M phosphate buffer (pH 7.4) was added to the reaction mixture, and the obtained mixture was then extracted with ethyl acetate. The gathered organic layer was washed with a saturated saline, dried over anhydrous sodium sulfate, and then concentrated under a reduced pressure. The obtained residue was purified by silica gel chromatography (methanol:chloroform) to obtain a corresponding protective group-removed body. The obtained protective group-removed body was subjected to the subsequent reaction without further purification.
Dichloromethane (0.5 mL) and TFA (1 mL) were added to the obtained protective group-removed product, and the obtained mixture was then stirred at a room temperature for 5 minutes. Thereafter, the reaction mixture was concentrated under a reduced pressure. Diisopropylethylamine (3 μL) was added to an ethanol solution (0.5 mL) of the obtained residue, and the obtained mixture was then cooled to 0° C. Acryloyl chloride (0.6 μL) was added to the reaction mixture, and the obtained mixture was then stirred for 5 minutes. Thereafter, an ammonia aqueous solution was added to the reaction mixture, and the obtained mixture was then stirred at a room temperature for 5 minutes. Thereafter, the reaction mixture was extracted with chloroform, and the gathered organic layer was washed with a saturated saline, dried over anhydrous sodium sulfate, and then concentrated under a reduced pressure. The obtained residue was purified by silica gel chromatography (chloroform:methanol) to obtain the title compound (1 mg, yield: 7%).
$^1$H NMR (CDCl$_3$) δ: 9.09 (s, 1H), 8.40 (d, J=5.1 Hz, 1H), 7.82 (s, 1H), 7.65 (d, J=8.4 Hz, 1H), 7.10 (d, J=5.1 Hz, 1H), 6.73 (dd, J=10.3, 17.2 Hz, 1H), 6.39 (dd, J=1.8, 17.2 Hz, 1H), 5.64 (dd, J=1.8, 10.3 Hz, 1H), 5.34 (br. s., 1H), 4.78-4.62 (m, 1H), 3.02-2.98 (m, 1H), 2.36 (d, J=16.1 Hz, 1H), 2.12-1.82 (m, 3H), 1.47-1.29 (m, 1H)
ESI-MS m/z 352 (MH$^+$)

Example 55

Example 55(1)

4-Chloro-1-trityl-1H-pyrrolo[2,3-b]pyridine-3-carbaldehyde (Compound 55(1))

DMF (50 mL) was added to 4-chloro-1H-pyrrolo[2,3-b]pyridine-3-carbaldehyde (1.81 g), and the obtained mixture was then cooled to 0° C. Thereafter, 60% sodium hydride (1.2 g) was added to the reaction mixture, and the obtained mixture was then stirred for 30 minutes. Thereafter, trityl chloride (5.02 g) was added to the reaction mixture, and the obtained mixture was then stirred at a room temperature for 40 minutes. Thereafter, the reaction mixture was cooled to 0° C., and ice and water were successively added to the mixture, followed by stirring for 30 minutes. Thereafter, the reaction mixture was filtered, and the residue was then washed with water. The obtained residue was purified by silica gel chromatography (hexane:ethyl acetate) to obtain a compound of interest (1.49 g, yield: 35%).
$^1$H NMR (DMSO-d$_6$) δ: 10.32 (s, 1H), 8.09 (s, 1H), 7.97 (d, J=5.1 Hz, 1H), 7.37-7.29 (m, 9H), 7.15-7.12 (m, 7H)
ESI-MS m/z 423 (MH$^+$)

Example 55(2)

4-Chloro-1-trityl-1H-pyrrolo[2,3-b]pyridine-3-carboxylic acid (Compound 55(2))

A product of interest (1.45 g, yield: 98%) was obtained in accordance with Example 49(1), with the exception that the Compound 55(1) was used instead of the Compound 48(2).
$^1$H NMR (DMSO-d$_6$) δ: 12.38 (br. s., 1H), 7.91-7.88 (m, 2H), 7.36-7.27 (m, 9H), 7.21 (d, J=5.1 Hz, 1H), 7.15-7.08 (m, 6H)
ESI-MS m/z 439 (MH$^+$)

Example 55(3)

4-Chloro-1-trityl-1H-pyrrolo[2,3-b]pyridine-3-carbohydrazide (Compound 55(3))

A product of interest (267 mg, yield: 86%) was obtained in accordance with Example 49(2), with the exception that the Compound 55(2) was used instead of the Compound 49(1).
$^1$H NMR (DMSO-d$_6$) δ: 9.42 (s, 1H), 7.88 (d, J=5.1 Hz, 1H), 7.59 (s, 1H), 7.36-7.24 (m, 9H), 7.18-7.10 (m, 7H), 4.38 (d, J=4.0 Hz, 2H)
ESI-MS m/z 453 (MH$^+$)

Example 55(4)

2-(4-Chloro-1-trityl-1H-pyrrolo[2,3-b]pyridin-3-yl)-1,3,4-oxadiazole (Compound 55(4))

A product of interest was obtained in accordance with Example 49(3), with the exception that the Compound 55(3) was used instead of the Compound 49(2).

$^1$H NMR (DMSO-d$_6$) δ: 9.30 (s, 1H), 8.00 (d, J=5.1 Hz, 1H), 7.93 (s, 1H), 7.38-7.27 (m, 10H), 7.20-7.13 (m, 6H)
ESI-MS m/z 463 (MH$^+$)

Example 55(5)

(S)-tert-Butyl (3-(3-(1,3,4-oxadiazol-2-yl)-1-trityl-1H-pyrrolo[2,3-b]pyridin-4-yl)cyclohex-3-en-1-yl) carbamate (Compound 55(5))

Under a nitrogen atmosphere, 1-butanol (43 mL) and water (17 mL) were added to the Compound 55(4) (850 mg), the compound of Reference Example 3 (711 mg), palladium (II) acetate (82 mg), 2-dicyclohexylphosphino-2',6'-dimethoxybiphenyl (301 mg) and tripotassium phosphate (780 mg), and the obtained mixture was then stirred at 110° C. for 42 hours. Thereafter, a saturated saline was added to the reaction mixture. The obtained mixture was extracted with ethyl acetate, and dried over anhydrous sodium sulfate, followed by vacuum concentration. The obtained residue was purified by silica gel chromatography (hexane:ethyl acetate) to obtain a product of interest (800 mg, yield: 70%).

$^1$H NMR (CDCl$_3$) δ: 8.46 (s, 1H), 8.00 (d, J=4.8 Hz, 1H), 7.85 (s, 1H), 7.31-7.27 (m, 9H), 7.24-7.16 (m, 6H), 6.85 (d, J=4.8 Hz, 1H), 5.54 (br. s., 1H), 5.41 (d, J=8.1 Hz, 1H), 4.05 (br. s., 1H), 2.88-2.76 (m, 1H), 2.36-2.22 (m, 1H), 2.12-2.07 (m, 2H), 1.89-1.70 (m, 2H), 1.47 (s, 9H)
ESI-MS m/z 624 (MH$^+$)

Example 55(6)

(S)-N-(3-(3-(1,3,4-Oxadiazol-2-yl)-1H-pyrrolo[2,3-b]pyridin-4-yl)cyclohex-3-en-1-yl)acrylamide (Compound 55)

TFA (1 mL) was added to the Compound 55(5) (100 mg), and the obtained mixture was then stirred at a room temperature for 30 minutes. Thereafter, the reaction mixture was concentrated under a reduced pressure. A 2 M aqueous solution of sodium carbonate was added to the obtained residue, and the obtained mixture was then extracted with a mixed solvent of ethanol/chloroform. The extract was dried over anhydrous sodium sulfate, and then concentrated under a reduced pressure. Ethanol (0.8 mL), water (0.8 mL) and diisopropylethylamine (54 µL) were added to the obtained residue, and the obtained mixture was then cooled to 0° C. Acryloyl chloride (14 µL) was added to the reaction mixture, and the obtained mixture was then stirred for 5 minutes. Thereafter, a saturated saline was added to the reaction mixture, and the obtained mixture was then extracted with chloroform. The extract was dried over anhydrous sodium sulfate, and then concentrated under a reduced pressure. The obtained residue was purified by silica gel chromatography (chloroform:methanol) to obtain the title compound (38 mg, yield: 70%).

$^1$H NMR (DMSO-d$_6$) δ: 12.64 (br. s., 1H), 9.29 (s, 1H), 8.31 (d, J=5.1 Hz, 1H), 8.21 (s, 1H), 8.19 (d, J=7.7 Hz, 1H), 7.05 (d, J=5.1 Hz, 1H), 6.34 (dd, J=10.3, 16.9 Hz, 1H), 6.10 (dd, J=2.2, 16.9 Hz, 1H), 5.58 (dd, J=2.2, 10.3 Hz, 1H), 5.42-5.36 (m, 1H), 4.16-4.04 (m, 1H), 2.71-2.58 (m, 1H), 2.30-2.20 (m, 1H), 2.07-1.99 (m, 2H), 1.86-1.75 (m, 1H), 1.65-1.51 (m, 1H)
ESI-MS m/z 336 (MH$^+$)

Example 56

N-(3-(3-(1,3,4-Oxadiazol-2-yl)-1H-pyrrolo[2,3-b]pyridin-4-yl) chlorohex-2-en-1-yl)acrylamide (Compound 56)

1,4-Dioxane (2.4 mL) and water (0.4 mL) were added to the Compound 55(4) (100 mg), the compound of Reference Example 1(2b) (98 mg), palladium(II) acetate (4.8 mg), 2-dicyclohexylphosphino-2',4',6'-triisopropylbiphenyl (20.6 mg) and disodium carbonate (45.8 mg), and the obtained mixture was then stirred at 130° C. for 90 minutes by the use of a microwave reaction apparatus. Thereafter, water was added to the reaction mixture, and the obtained mixture was then extracted with ethyl acetate. The organic layer was washed with a saturated saline, dried over anhydrous sodium sulfate, and then concentrated under a reduced pressure. The obtained residue was purified by silica gel chromatography (hexane:ethyl acetate) to obtain a coupling product. The obtained coupling product was subjected to the subsequent reaction without further purification.

TFA (1 mL) was added to the obtained coupling product, and the obtained mixture was then stirred at a room temperature for 20 minutes. Thereafter, the reaction mixture was concentrated under a reduced pressure. The obtained residue was purified by basic silica gel chromatography (chloroform:methanol) to obtain an amine product. The obtained amine product was subjected to the subsequent reaction without further purification.

Methylene chloride (2.0 mL) and diisopropylethylamine (0.30 mL) were added to the obtained amine product, and the obtained mixture was then cooled to 0° C. Acryloyl chloride (0.022 mL) was added to the reaction mixture, and the obtained mixture was then stirred for 30 minutes. Thereafter, an ammonia aqueous solution, chloroform and methanol were successively added to the reaction mixture, and the obtained mixture was then stirred at a room temperature for 1 hour. Thereafter, the reaction mixture was extracted with chloroform, and the gathered organic layer was washed with a saturated saline, dried over anhydrous sodium sulfate, and then concentrated under a reduced pressure. The obtained residue was purified by silica gel chromatography (chloroform:methanol) to obtain the title compound (38.1 mg, yield: 66%).

$^1$H NMR (CDCL$_3$-CD$_3$OD) δ: 8.52 (s, 1H), 8.32 (d, J=4.9 Hz, 1H), 8.04 (s, 1H), 7.03 (d, J=4.9 Hz, 1H), 6.41-6.27 (m, 2H), 5.72-5.61 (m, 2H), 4.76-4.65 (m, 1H), 2.32-2.22 (m, 2H), 2.04-1.82 (m, 3H), 1.80-1.67 (m, 1H)
ESI-MS m/z 336 (MH$^+$)

Example 57

N-(3-(3-(1,3,4-Oxadiazol-2-yl)-1H-pyrrolo[2,3-b]pyridin-4-yl)cyclopent-3-en-1-yl)acrylamide (Compound 57)

The title compound was obtained in accordance with Example 56, with the exception that the compound of Reference Example 2(2a) was used instead of the compound of Reference Example 1(2b).

¹H NMR (CDCL₃-CD₃OD) δ: 8.58 (s, 1H), 8.31 (d, J=4.9 Hz, 2H), 8.07 (s, 1H), 7.07 (d, J=4.9 Hz, 1H), 6.58-6.45 (m, 1H), 6.39-6.28 (m, 1H), 5.72-5.57 (m, 2H), 4.92-4.78 (m, 1H), 3.26-3.12 (m, 1H), 3.04-2.89 (m, 1H), 2.82-2.72 (m, 1H), 2.51-2.41 (m, 1H)

ESI-MS m/z 322 (MH⁺)

Example 58

N-(3-(3-(1,3,4-Oxadiazol-2-yl)-1H-pyrrolo[2,3-b]pyridin-4-yl)cyclopent-2-en-1-yl)acrylamide (Compound 58)

The title compound was obtained in accordance with Example 56, with the exception that the compound of Reference Example 2(2b) was used instead of the compound of Reference Example 1(2b).

¹H NMR (CDCL₃-CD₃OD) δ: 8.60 (s, 1H), 8.32 (d, J=4.9 Hz, 1H), 8.08 (s, 1H), 7.09 (d, J=4.9 Hz, 1H), 6.47-6.28 (m, 2H), 5.72-5.60 (m, 2H), 5.27-5.17 (m, 1H), 2.94-2.83 (m, 1H), 2.70-2.45 (m, 2H), 2.02-1.91 (m, 1H)

ESI-MS m/z 322 (MH⁺)

Example 59

Example 59(1)

5-(4-Chloro-1-(phenylsulfonyl)-1H-pyrrolo[2,3-b]pyridin-3-yl)isoxazole (Compound 59(1))

Ethanol (5 mL) was added to (E)-1-(4-chloro-1-(phenylsulfonyl)-1H-pyrrolo[2,3-b]pyridin-3-yl)-3-(dimethylamino)prop-2-en-1-one (250 mg) and hydroxyamine hydrochloride (53 mg), and the obtained mixture was then stirred at 80° C. for 2 hours. Thereafter, water was added to the reaction mixture, and the obtained mixture was then extracted with ethyl acetate. The extract was dried over anhydrous sodium sulfate, and then concentrated under a reduced pressure. The obtained solid was washed with ethyl acetate and diisopropyl ether to obtain a product of interest (191 mg, yield: 83%).

¹H-NMR (CDCl₃) δ: 8.38 (d, J=5.5 Hz, 1H), 8.34 (d, J=1.8 Hz, 1H), 8.26 (d, J=8.4 Hz, 2H), 8.22 (s, 1H), 7.65 (t, J=7.7 Hz, 1H), 7.54 (dd, J=8.4, 7.7 Hz, 2H), 7.29 (d, J=5.5 Hz, 1H), 6.68 (d, J=1.8 Hz, 1H)

ESI-MS m/z 360 (MH⁺)

Example 59(2)

(S)-N-(3-(3-(Isoxazol-5-yl)-1H-pyrrolo[2,3-b]pyridin-4-yl)cyclohex-3-en-1-yl)acrylamide (Compound 59)

The title compound was obtained in accordance with Example 45(3), with the exception that the Compound 59(1) was used instead of the Compound 45(2).

¹H-NMR (CDCl₃) δ: 11.34 (br. s., 1H), 8.36-8.29 (m, 2H), 7.68 (s, 1H), 7.04 (d, J=5.1 Hz, 1H), 6.55-6.43 (m, 2H), 6.40-6.31 (m, 2H), 5.67-5.63 (m, 1H), 5.51-5.46 (m, 1H), 4.66-4.57 (m, 1H), 2.98-2.88 (m, 1H), 2.37-2.28 (m, 1H), 2.16-2.08 (m, 1H), 1.96-1.75 (m, 3H)

ESI-MS m/z 335 (MH⁺)

Comparative Example 1

4-(Cyclohex-1-en-1-yl)-1H-pyrrolo[2,3-b]pyridine

Compound 30 described in International Publication No. WO 2006/127587 was synthesized in accordance with the method described in this publication.

Comparative Example 2

4-(Cyclopent-1-en-1-yl)-1H-pyrrolo[2,3-b]pyridine

Compound 27 described in International Publication No. WO 2006/127587 was synthesized in accordance with the method described in this publication.

Comparative Example 3

2-Methyl-4-(5-phenyl-1H-pyrrolo[2,3-b]pyridin-3-yl)thiazole

Compound I-1 described in International Publication No. WO 2006/004984 was synthesized in accordance with the method described in this publication.

Hereinafter, the structural formulae of the compounds described in Examples 1 to 59 and Comparative Examples 1 to 3 will be shown.

TABLE 2

| Compound No. | Structural formula |
| --- | --- |
| 1 | |
| 2 | |
| 3 | |

TABLE 2-continued

| Compound No. | Structural formula |
|---|---|
| 4 | (3-pyridyl substituted 7-azaindole with cyclohexenyl acrylamide) |
| 5 | (6-hydroxymethylpyridin-3-yl substituted 7-azaindole with cyclohexenyl acrylamide) |
| 6 | (2-methoxypyridin-3-yl substituted 7-azaindole with cyclohexenyl acrylamide) |
| 7 | (4-methoxypyridin-3-yl substituted 7-azaindole with cyclohexenyl acrylamide) |
| 8 | (2-hydroxypyridin-3-yl substituted 7-azaindole with cyclohexenyl acrylamide) |
| 9 | (5-formylfuran-2-yl substituted 7-azaindole with cyclohexenyl acrylamide) |
| 10 | (5-hydroxymethylfuran-2-yl substituted 7-azaindole with cyclohexenyl acrylamide) |
| 11 | (5-hydroxymethylpyridin-3-yl substituted 7-azaindole with cyclohexenyl acrylamide) |
| 12 | (furan-2-yl substituted 7-azaindole with cyclohexenyl acrylamide) |

TABLE 3

| Compound No. | Structural formula |
|---|---|
| 13 | (thiazol-5-yl substituted 7-azaindole with cyclohexenyl acrylamide) |

TABLE 3-continued
| Compound No. | Structural formula |
|---|---|
| 14 | 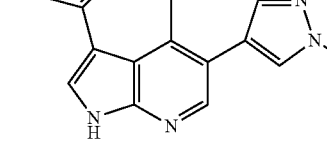 |
| 15 | 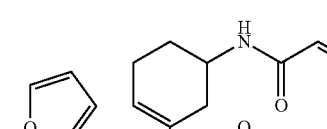 |
| 16 | 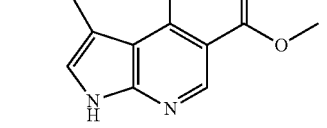 |
| 17 | 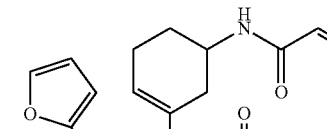 |
| 18 | 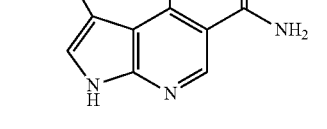 |
| 19 | |
| 20 | |
| 21 | |
| 22 | |
| 23 | |
| 24 | 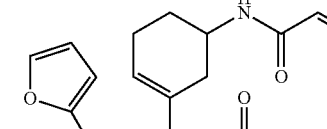 |

TABLE 3-continued
| Compound No. | Structural formula |
|---|---|
TABLE 4
| Compound No. | Structural formula |
|---|---|
| 25 | 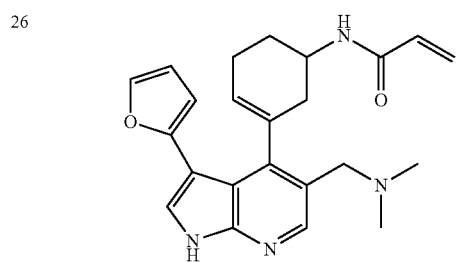 |
| 26 | 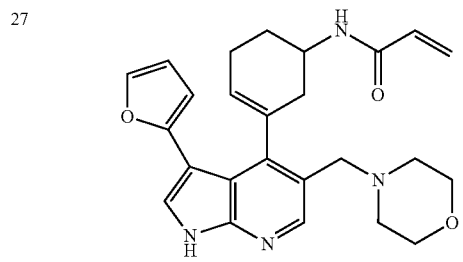 |
| 27 | 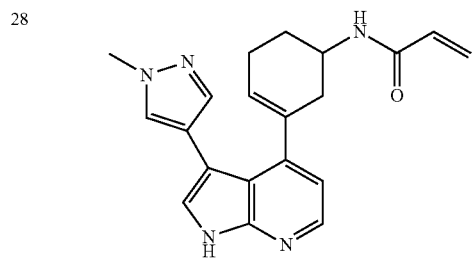 |
| 28 | 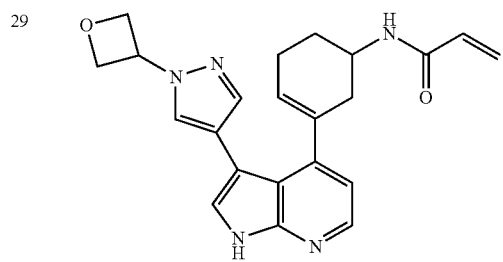 |
| 29 | 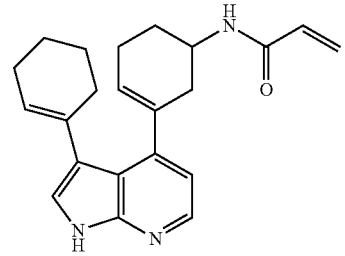 [SMILES: C=CC(=O)NC1CCC=C(c2ccnc3[nH]cc(C4=CCOCC4)c23)C1] |
TABLE 4-continued
| Compound No. | Structural formula |
|---|---|
| 30 | 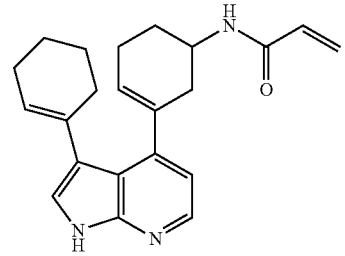 [SMILES: C=CC(=O)NC1CCC=C(c2ccnc3[nH]cc(C4=CCOCC4)c23)C1] |
| 31 | 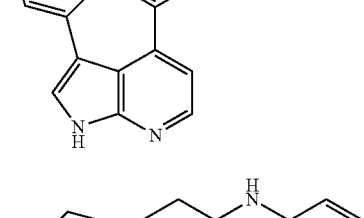 |
| 32 | 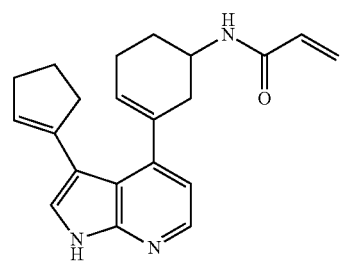 [SMILES: C=CC(=O)NC1CCC=C(c2ccnc3[nH]cc(C4=CCCC4)c23)C1] |
| 33 | 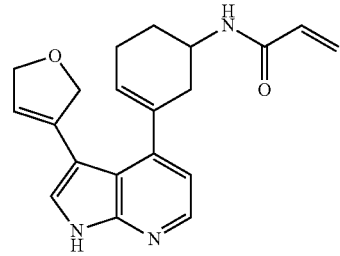 |
| 34 | 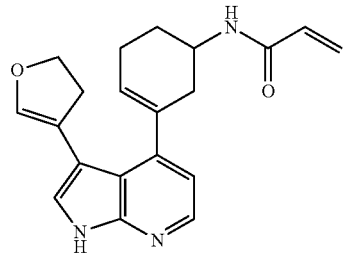 [SMILES: C=CC(=O)NC1CCC=C(c2ccnc3[nH]cc(C4=COCC4)c23)C1] |
| 35 | 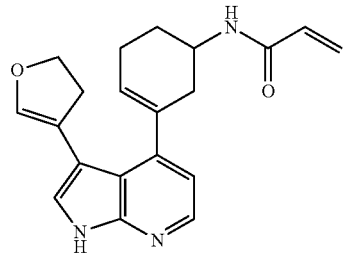 [SMILES: C=CC(=O)NC1CCC=C(c2ccnc3[nH]cc(C4=COCC4)c23)C1] |

TABLE 4-continued
| Compound No. | Structural formula |
|---|---|
| 36 | 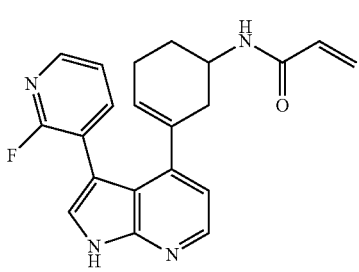 |
TABLE 5
| Compound No. | Structural formula |
|---|---|
| 37 | 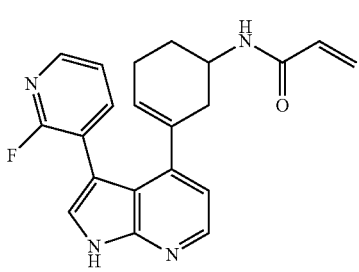 |
| 38 | 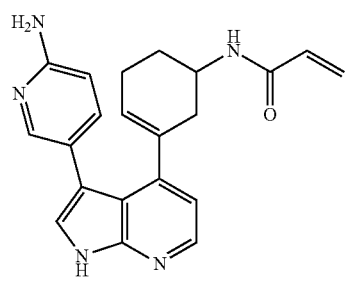 [SMILES: C=CC(=O)NC1CCC=C(c2ccnc3[nH]cc(-c4ccc(F)nc4)c23)C1] |
| 39 | 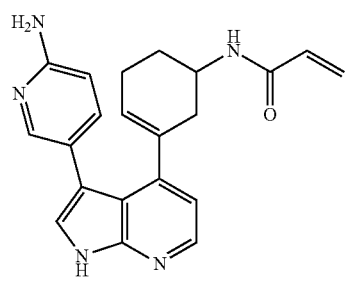 [SMILES: C=CC(=O)NC1CCC=C(c2ccnc3[nH]cc(-c4ccc(F)nc4)c23)C1] |
TABLE 5-continued
| Compound No. | Structural formula |
|---|---|
| 40 | 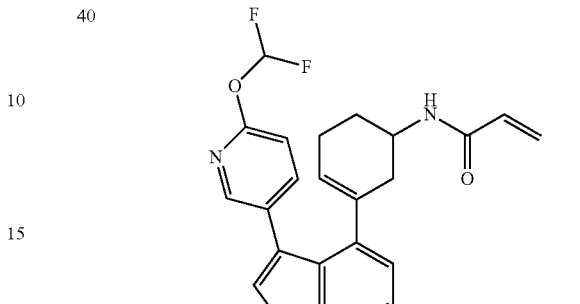 |
| 41 | 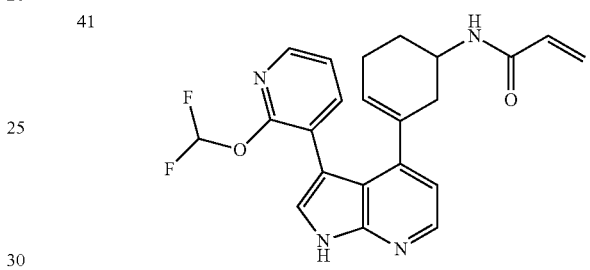 |
| 42 | 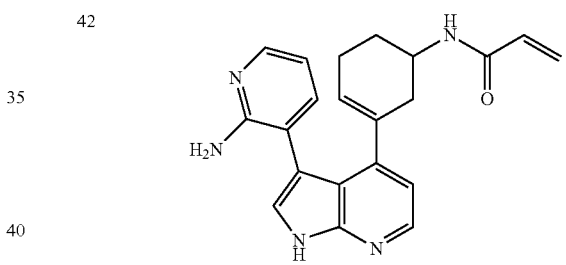 |
| 43 | 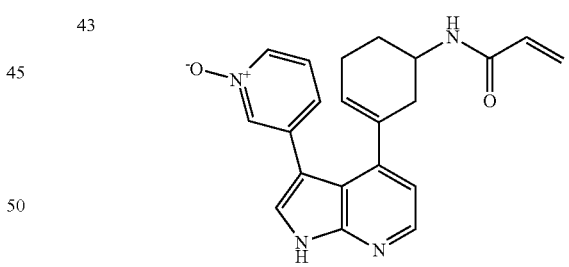 |
| 44 | 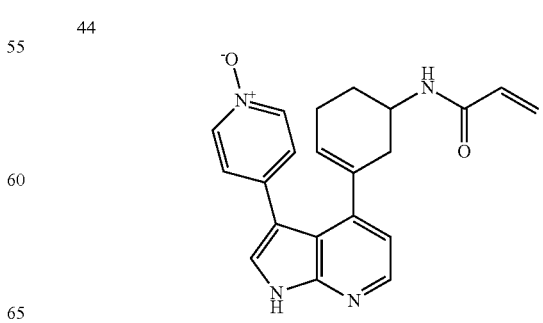 |

| Compound No. | Structural formula |
|---|---|
| 45 | |
| 46 | |
| 47 | |
| 48 | |
TABLE 6
| Compound No. | Structural formula |
|---|---|
| 49 | |
| 50 | |
| 51 | |
| 52 | |
| 53 | |
| 54 | |
| 55 | |
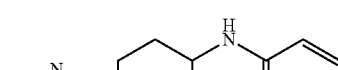

TABLE 6-continued

| Compound No. | Structural formula |
|---|---|
| 56 | 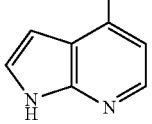 |
| 57 | |
| 58 | |
| 59 | |
| Comparative Example 1 | |

TABLE 7

| Compound No. | Structural formula |
|---|---|
| Comparative Example 2 | 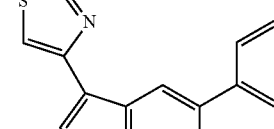 |
| Comparative Example 3 | |

TEST EXAMPLES

The compound according to the present invention was evaluated by the following test methods:

Test Example 1

Test Regarding Action to Inhibit Various JAK Kinase Activities (In Vitro)

1) Measurement of JAK1 Kinase-inhibitory Activity

The activity of the compound of the present invention to inhibit the activity of JAK1 kinase was measured.

Among materials for the measurement of this inhibitory activity, a substrate peptide and a kinase protein were acquired as follows. As such a substrate peptide, a substrate peptide for QSS Assist™ JAK1-MSA assay kit (Carna Biosciences, Inc.) was purchased. As such a kinase protein, a purified recombinant human JAK1 protein (Carna Biosciences, Inc.) was purchased.

The method for measuring the inhibitory activity is as follows. First, the compounds of the present invention were each dissolved in dimethyl sulfoxide (DMSO), and a serial dilution was then prepared by the use of DMSO. Subsequently, a serial dilution solution of the compound (the final concentration of DMSO upon a kinase reaction: 5.0%) or DMSO (final concentration: 5.0%) was mixed with a solution containing the substrate peptide (final concentration: 1 µM), magnesium chloride (final concentration: 5 mM) and ATP (final concentration: 75 µM) in a buffer for kinase reaction (20 mM HEPES (pH 7.5), 2 mM dithiothreitol and 0.01% Triton X-100). Thereafter, a JAK1 protein was further added to the mixed solution, and the obtained mixture was then incubated at 25° C. for 120 minutes to carry out a kinase reaction. To the reaction solution, EDTA was added to a final concentration of 30 mM, so as to terminate the reaction. Finally, with LabChip EZ Reader II (Perkin Elmer Corp.), an unphosphorylated substrate peptide (S) and a phosphorylated peptide (P) were subjected to microchannel capillary electrophoresis, so that the two peptides were separated from each other and were then detected. The amount of a phosphorylation reaction was obtained based on the heights of the peaks of S and P, and the concentration of the compound capable of inhibiting 50% of the phosphorylation reaction was defined as an IC50 value (nM). The obtained data are shown in a table below.

2) Measurement of JAK2 Kinase-inhibitory Activity

The activity of the compound of the present invention to inhibit the activity of JAK2 kinase was measured.

Among materials for the measurement of this inhibitory activity, a substrate peptide and a kinase protein were acquired as follows. As such a substrate peptide, FL-Peptide 22 (Perkin Elmer Corp.) was purchased. As such a kinase protein, a purified recombinant human JAK2 protein (Carna Biosciences, Inc.) was purchased.

The method for measuring the inhibitory activity is as follows. First, a serial dilution of the compound of the present invention was prepared by the same method as that described in the above section regarding JAK1. This serial dilution solution (the final concentration of DMSO upon a kinase reaction: 5.0%) or DMSO (final concentration: 5.0%) was mixed with a solution containing the substrate peptide (final concentration: 1 µM), magnesium chloride (final concentration: 10 mM) and ATP (final concentration: 10 M) in a buffer for kinase reaction (15 mM Tris (pH 7.5), 2 mM dithiothreitol and 0.01% Tween 20). Thereafter, a JAK2 protein was further added to the mixed solution, and the obtained mixture was then incubated at 25° C. for 80 minutes to carry out a kinase reaction. To the reaction solution, EDTA was added to a final concentration of 30 mM, so as to terminate the reaction. After termination of the reaction, the measurement and the data analysis were carried out by the same methods as those described in the above section regarding JAK1.

3) Measurement of JAK3 Kinase-inhibitory Activity

The activity of the compound of the present invention to inhibit the activity of JAK3 kinase was measured.

Among materials for the measurement of this inhibitory activity, a substrate peptide and a kinase protein were acquired as follows. As such a substrate peptide, a substrate peptide for QSS Assist™ JAK3-MSA assay kit (Carna Biosciences, Inc.) was purchased. As such a kinase protein, a purified recombinant human JAK3 protein (Carna Biosciences, Inc.) was purchased.

The method for measuring the inhibitory activity is as follows. First, a serial dilution of the compound of the present invention was prepared by the same method as that described in the above section regarding JAK1. This serial dilution solution (the final concentration of DMSO upon a kinase reaction: 5.0%) or DMSO (final concentration: 5.0%) was mixed with a solution containing the substrate peptide (final concentration: 1 µM), magnesium chloride (final concentration: 5 mM) and ATP (final concentration: 5 M) in a buffer for kinase reaction (20 mM HEPES (pH 7.5), 2 mM dithiothreitol and 0.01% Triton X-100). Thereafter, a JAK3 protein was further added to the mixed solution, and the obtained mixture was then incubated at 25° C. for 80 minutes to carry out a kinase reaction. To the reaction solution, EDTA was added to a final concentration of 30 mM, so as to terminate the reaction. After termination of the reaction, the measurement and the data analysis were carried out by the same methods as those described in the above section regarding JAK1.

As a result, it was found that, as shown in Table 8 below, the compound of the present invention or a salt thereof had a stronger JAK3-inhibitory activity than that of each of the compounds described in Patent Literatures 1 and 2, and had extremely high selectivity to JAK3.

TABLE 8

| Example No. | JAK1 IC50 (nM) | JAK2 IC50 (nM) | JAK3 IC50 (nM) |
|---|---|---|---|
| 1 | 740 | 450 | <0.30 |
| 2 | >10000 | 3100 | 0.38 |
| 3 | 1900 | 570 | <0.30 |
| 4 | 7000 | 2600 | 0.53 |
| 6 | 1100 | 600 | 0.42 |
| 9 | 2400 | 430 | <0.30 |
| 10 | 1900 | 250 | <0.30 |
| 11 | 9500 | 1900 | 0.49 |
| 12 | 780 | 500 | <0.30 |
| 13 | 5200 | 2000 | 0.34 |
| 14 | 3200 | 590 | <0.30 |
| 17 | 860 | 170 | <0.30 |
| 19 | 1000 | 280 | 0.51 |
| 30 | 3200 | 1400 | 0.48 |
| 31 | 7700 | 3000 | 0.71 |
| 32 | >10000 | 3000 | 0.72 |
| 33 | 3600 | 1400 | 0.60 |
| 34 | 2400 | 970 | <0.30 |
| 37 | 4400 | 2400 | <0.30 |
| 38 | 5800 | 2500 | 0.67 |
| 39 | >10000 | 4800 | 0.83 |
| 43 | >10000 | 9100 | 0.93 |
| 45 | 1600 | 440 | 0.34 |
| 48 | 2400 | 710 | <0.30 |
| 49 | 3400 | 980 | <0.30 |
| 50 | 3800 | 920 | 0.62 |
| 51 | 3000 | 380 | 0.61 |
| 52 | 890 | 480 | <0.30 |
| 53 | 3900 | 990 | <0.30 |
| 54 | 6900 | 2100 | 0.45 |
| 55 | >1000 | 260 | <0.30 |
| 57 | 3500 | 880 | 0.57 |
| 59 | 1500 | 430 | <0.30 |
| Comparative Example 1 | 1200 | 450 | 250 |
| Comparative Example 2 | 2200 | 540 | 350 |
| Comparative Example 3 | 2900 | 1600 | 460 |

Test Example 2

Test Regarding Growth of Human Peripheral Blood Mononuclear Cells (PBMC)

The activity of the compound of the present invention to inhibit the IL-2-dependent growth reaction of human PBMC, which is caused by JAK3, was measured (Arthritis Rheum. 2010; 62(8): 2283-93).

With a medium containing 10 µg/mL PHA-M (Sigma) (which is RPMI-1640 (Sigma) containing 10% human serum type AB (MP Biomedicals)), human PBMC (C.T.L.) (cell density: $1\times10^6$ cells/mL) was cultured at 37° C. in a culture vessel containing 5% carbon dioxide for 3 days. Thereafter, the culture was washed with RPMI-1640 four times, and a medium (RPMI-1640 containing 10% human serum type AB) was then added to the resultant culture to prepare a cell suspension. The cells ($1\times10^4$ cells per well) and the serially diluted compound of the present invention were added to each well of a 96-well U-bottom microplate, and thus obtained mixture was then cultured at 37° C. in a culture vessel containing 5% carbon dioxide for 30 minutes. After completion of the culture, recombinant human IL-2 (Peprotech) was added to the culture to a final concentration of 2 ng/mL, and the obtained mixture was then stirred at 37° C. in a culture vessel containing 5% carbon dioxide for 2 days ($1\times10^4$ cells/100 l/each well). After completion of the culture, the resultant was left at a room temperature for 30 minutes, and 100 μl of CellTiter-Glo Luminescent Cell Viability Assay (Promega) was then added to the resultant, followed by stirring it. Thereafter, the reaction mixture was left for 10 minutes, and the amount of a luminescence derived from living cells in each well was then measured with a microplate reader (TECAN). The inhibition rate of the compound to the cell growth caused by IL-2 stimulation was calculated, and the concentration of the compound capable of inhibiting 50% of the cell growth was defined as an IC50 value (nM). The obtained data are shown in a table below.

As a result, it was found that the compound of the present invention or a salt thereof has a stronger PBMC growth-inhibitory effect than that of each of the compounds described in Patent Literatures 1 to 3.

TABLE 9

| Compound No. | PBMC IC50 (nM) |
|---|---|
| 1 | 216 |
| 3 | 182 |
| 6 | 181 |
| 10 | 136 |
| 12 | 123 |
| 14 | 114 |
| 34 | 82 |
| 37 | 159 |
| 48 | 114 |
| 49 | 122 |
| 53 | 162 |
| 54 | 170 |
| 55 | 34 |
| 57 | 304 |
| 59 | 55 |
| Comparative Example 1 | >3000 |
| Comparative Example 2 | >3000 |
| Comparative Example 3 | >3000 |

Test Example 3

Therapeutic Effect on Rheumatoid Arthritis

Collagen-induced arthritis, which is a mouse experimental model for rheumatoid arthritis, was used. The clinical symptoms of arthritis were scored, the obtained scores were used as indicators, and the action of the compound of the present invention by oral administration was confirmed. Six-week-old male DBA/1 mice (Charles River Laboratories Japan, Inc.) were administered with a 100 μL/body solution (emulsion), which had been obtained by mixing a 4 mg/mL bovine type 2 collagen solution (Collagen Research Center) with a Freund's complete adjuvant (DIFCO) in equal amounts, via dorsal intradermal injection (initial immunization). Twenty-one days after the initial immunization, the mice were administered with a 100 μL/body solution (emulsion), which had been obtained by mixing a 4 mg/mL bovine type 2 collagen solution (Collagen Research Center) with a Freund's incomplete adjuvant (DIFCO) in equal amounts, via intradermal injection to the tail base thereof (booster), so as to induce an arthritis reaction (Arthritis Rheum 2010; 62 (8): 2283-93). Seven days after the implementation day of the booster (which is defined as Day 0), the compound of the present invention was continuously administered to the mice for 13 days via oral administration of twice a day. On Day 7, Day 9, Day 12, Day 15 and Day 19, the clinical symptoms of arthritis were scored by observation with naked eyes, and the action of the compound of the present invention was then confirmed. The clinical symptoms for each limb were scored (0: not changed, 1: one finger swelled, 2: two or more fingers swelled, 3: instep swelled, 4: all fingers swelled and also wrist or ankle swelled), and a total score from the four limbs was defined as a score for an individual mouse (the highest score: 16).

As a result, it was found that the compound of the present invention showed an excellent therapeutic effect on rheumatoid arthritis.

Test Example 4

Therapeutic Effect on Multiple Sclerosis

Experimental autoimmune encephalomyelitis, which is a mouse experimental model for multiple sclerosis, was used. Eight-week-old male SJL/J mice (Charles River Laboratories Japan, Inc.) were administered with a mixed solution (emulsion), which had been obtained by mixing a normal saline aqueous solution (1 mg/mL) of a peptide (Toray Research Center, Inc.) corresponding to 139-151 residues of a proteolipid protein with a Freund's complete adjuvant (DIFCO) containing 4 mg/mL killed *Mycobacterium tuberculosis* (H37Ra) in equal amounts, via intradermal injection in an amount of 100 μL each into two sites of the dorsal portion of each mouse, so as to induce encephalomyelitis. Seven days after the implementation day of the immunization (which is defined as Day 0), the compound of the present invention was continuously administered to the mice for 4 weeks via oral administration of twice a day. On Day 0, Day 2, Day 5, and Days 7 to 35, the clinical symptoms of encephalomyelitis were observed with naked eyes, and the action of the compound of the present invention was then confirmed. The observed clinical symptoms were scored (0: no symptoms, 1: weakened tail, 1.5: complete ptosis of tail, 2: ataxia, 3: light paralysis of hindlimbs, 3.5: light paralysis of hindlimbs, 4. complete paralysis of hindlimbs, 4.5: paralysis of four limbs, dying, 5: death).

As a result, it was found that the compound of the present invention showed an excellent therapeutic effect on multiple sclerosis.

Test Example 5

Evaluation of Oral Absorbability

The compound of the present invention was suspended or dissolved in 0.5% HPMC, and the obtained suspension or solution was administered to BALB/cA mice via oral administration. 0.5, 1, 2, 4 and 6 hours after completion of the oral administration, blood was collected from the eye ground of each mouse, to obtain plasma. The concentration of the compound in the obtained plasma was measured by LCMS, and oral absorbability was then evaluated.

As a result, it was found that, after completion of the oral administration, the compound of the present invention was present in a sufficient concentration in the plasma, and that the compound exhibited good oral absorbability.

The invention claimed is:
1. A method for treating rheumatoid arthritis, comprising: administering a compound of the formula (I) or a salt thereof to a subject in need thereof,

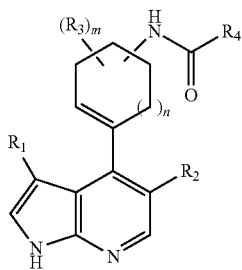

(I)

wherein:
R$_1$ represents an optionally substituted C$_4$-C$_{10}$ cycloalkyl group, an optionally substituted C$_4$-C$_{10}$ cycloalkenyl group, an optionally substituted C$_4$-C$_{10}$ cycloalkynyl group, an optionally substituted C$_6$-C$_{14}$ aromatic hydrocarbon group, or an optionally substituted 4- to 10-membered saturated or unsaturated heterocyclic group;
R$_2$ represents a hydrogen atom, a halogen atom, a hydroxy group, a cyano group, a nitro group, —C(=O)R$_x$, —C(=O)OR$_x$, —C(=O)N(R$_x$)(R$_y$), —N(R$_x$)(R$_y$), —NR$_x$C(=O)R$_y$, —NR$_x$S(=O)$_2$R$_y$, —NR$_x$C(=O)OR$_y$, —NR$_x$C(=O)N(R$_y$)(R$_z$), —NR$_x$S(=O)$_2$N(R$_y$)(R$_z$), —OC(=O)R$_x$, —OC(=O)OR$_x$, —OC(=O)N(R$_x$)(R$_y$), —SR$_x$, —S(=O)$_2$R$_x$, —S(=O)$_2$OR$_x$, an optionally R$_b$-substituted C$_1$-C$_6$ alkyl group, an optionally R$_b$-substituted C$_2$-C$_6$ alkenyl group, an optionally R$_b$-substituted C$_2$-C$_6$ alkynyl group, an optionally R$_b$-substituted C$_1$-C$_6$ alkoxy group, an optionally R$_c$-substituted C$_3$-C$_{10}$ cycloalkyl group, an optionally R$_c$-substituted C$_6$-C$_{14}$ aromatic hydrocarbon group, or an optionally R$_c$-substituted 4- to 10-membered saturated or unsaturated heterocyclic group;
R$_3$ represents a halogen atom, an amino group, a hydroxy group, a cyano group, a nitro group, a C$_1$-C$_6$ alkyl group, a C$_2$-C$_6$ alkenyl group, a C$_2$-C$_6$ alkynyl group, or a C$_1$-C$_6$ alkoxy group;
R$_4$ represents an optionally R$_b$-substituted C$_2$-C$_6$ alkenyl group or an optionally R$_b$-substituted C$_2$-C$_6$ alkynyl group;
R$_b$ represents a halogen atom, an amino group, a hydroxy group, a cyano group, a nitro group, a C$_1$-C$_6$ alkoxy group, a di- or mono-(C$_1$-C$_6$ alkyl)amino group, or a 4- to 10-membered saturated or unsaturated heterocyclic group;
R$_c$ represents a halogen atom, an amino group, a hydroxy group, a cyano group, a nitro group, an oxo group, an imino group, an N-oxide group, a C$_1$-C$_6$ alkyl group, a C$_2$-C$_6$ alkenyl group, a C$_2$-C$_6$ alkynyl group, a C$_1$-C$_6$ alkoxy group, or a di- or mono-(C$_1$-C$_6$ alkyl)amino group;
R$_x$, R$_y$ and R$_z$, which are the same or different, each represent a hydrogen atom, a C$_1$-C$_6$ alkyl group, a C$_1$-C$_6$ haloalkyl group, a C$_2$-C$_6$ alkenyl group, a C$_2$-C$_6$ alkynyl group, a C$_3$-C$_{10}$ cycloalkyl group, a C$_6$-C$_{14}$ aromatic hydrocarbon group, or a 4- to 10-membered saturated or unsaturated heterocyclic group;
m represents an integer of 0 to 3; and
n represents an integer of 0 to 2.

2. The method of claim 1,
wherein a group with which the C$_4$-C$_{10}$ cycloalkyl group, C$_4$-C$_{10}$ cycloalkenyl group, C$_4$-C$_{10}$ cycloalkynyl group, C$_6$-C$_{14}$ aromatic hydrocarbon group or 4- to 10-membered saturated or unsaturated heterocyclic group, which is represented by R$_1$, is optionally substituted is R$_a$, and
R$_a$ represents a halogen atom, a hydroxy group, a cyano group, a nitro group, an oxo group, an N-oxide group, —C(=O)R$_x$, —C(=O)OR$_x$, —C(=O)N(R$_x$)(R$_y$), —C(=O)SR$_x$, —C(=S)OR$_x$, —C(=O)ON(R$_x$)(R$_y$), —N(R$_x$)(R$_y$), —NR$_x$C(=O)R$_y$, —NR$_x$S(=O)$_2$R$_y$, —NR$_x$C(=O)OR$_y$, —NR$_x$C(=O)N(R$_y$)(R$_z$), —NR$_x$S(=O)$_2$N(R$_y$)(R$_z$), —N(R$_x$)—OR$_y$, =NR$_x$, =N—OR$_x$, —OC(=O)R$_x$, —OC(=S)R$_x$, —OC(=O)OR$_x$, —OC(=O)N(R$_x$)(R$_y$), —OC(=S)OR$_x$, —SR$_x$, —S(=O)$_2$R$_x$, —S(=O)$_2$OR$_x$, —S(=O)$_2$N(R$_x$)(R$_y$), an optionally R$_b$-substituted C$_1$-C$_6$ alkyl group, an optionally R$_b$-substituted C$_2$-C$_6$ alkenyl group, an optionally R$_b$-substituted C$_2$-C$_6$ alkynyl group, an optionally R$_b$-substituted C$_1$-C$_6$ alkoxy group, an optionally R$_c$-substituted C$_3$-C$_{10}$ cycloalkyl group, an optionally R$_c$-substituted C$_6$-C$_{14}$ aromatic hydrocarbon group, or an optionally R$_c$-substituted 4- to 10-membered saturated or unsaturated heterocyclic group.

3. The method of claim 1,
wherein R$_1$ represents an optionally R$_a$-substituted C$_5$-C$_7$ cycloalkenyl group, an optionally R$_a$-substituted C$_6$-C$_{10}$ aromatic hydrocarbon group, or an optionally R$_a$-substituted monocyclic 4- to 7-membered unsaturated heterocyclic group having 1 to 3 heteroatoms selected from the group consisting of N, S and O, and
R$_a$ represents a halogen atom, a hydroxy group, a cyano group, a nitro group, an oxo group, an N-oxide group, —C(=O)R$_x$, —C(=O)OR$_x$, —C(=O)N(R$_x$)(R$_y$), —C(=O)SR$_x$, —C(=S)OR$_x$, —C(=O)ON(R$_x$)(R$_y$), —N(R$_x$)(R$_y$), —NR$_x$C(=O)R$_y$, —NR$_x$S(=O)$_2$R$_y$, —NR$_x$C(=O)OR$_y$, —NR$_x$C(=O)N(R$_y$)(R$_z$), —NR$_x$S(=O)$_2$N(R$_y$)(R$_z$), —N(R$_x$)—OR$_y$, =NR$_x$, =N—OR$_x$, —OC(=O)R$_x$, —OC(=S)R$_x$, —OC(=O)OR$_x$, —OC(=O)N(R$_x$)(R$_y$), —OC(=S)OR$_x$, —SR$_x$, —S(=O)$_2$R$_x$, —S(=O)$_2$OR$_x$, —S(=O)$_2$N(R$_x$)(R$_y$), an optionally R$_b$-substituted C$_1$-C$_6$ alkyl group, an optionally R$_b$-substituted C$_2$-C$_6$ alkenyl group, an optionally R$_b$-substituted C$_2$-C$_6$ alkynyl group, an optionally R$_b$-substituted C$_1$-C$_6$ alkoxy group, an optionally R$_c$-substituted C$_3$-C$_{10}$ cycloalkyl group, an optionally R$_c$-substituted C$_6$-C$_{14}$ aromatic hydrocarbon group, or an optionally R$_c$-substituted 4- to 10-membered saturated or unsaturated heterocyclic group.

4. The method of claim 1,
wherein R$_1$ represents an optionally R$_a$-substituted cyclopentenyl group, cyclohexenyl group, phenyl group, furanyl group, 1H-pyrazolyl group, thiazolyl group, oxazolyl group, isoxazolyl group, 1,3,4-thiadiazolyl group, 1,2,4-oxadiazolyl group, 1,3,4-oxadiazolyl group, pyridyl group, dihydropyranyl group, dihydrofuranyl group, or 4,5-dihydro-1,3,4-oxadiazolyl group, and
R$_a$ represents a halogen atom, a hydroxy group, a cyano group, a nitro group, an oxo group, an N-oxide group, —C(=O)R$_x$, —C(=O)OR$_x$, —C(=O)N(R$_x$)(R$_y$), —C(=O)SR$_x$, —C(=S)OR$_x$, —C(=O)ON(R$_x$)(R$_y$), —N(R$_x$)(R$_y$), —NR$_x$C(=O)R$_y$, —NR$_x$S(=O)$_2$R$_y$, —NR$_x$C(=O)OR$_y$, —NR$_x$C(=O)N(R$_y$)(R$_z$), —NR$_x$S(=O)$_2$N(R$_y$)(R$_z$), —N(R$_x$)—OR$_y$, =NR$_x$, =N—OR$_x$, —OC(=O)R$_x$, —OC(=S)R$_x$, —OC(=O)OR$_x$, —OC(=O)N(R$_x$)(R$_y$), —OC(=S)OR$_x$, —SR$_x$, —S(=O)$_2$R$_x$, —S(=O)$_2$OR$_x$, —S(=O)$_2$N(R$_x$)(R$_y$), an optionally R$_b$-substituted C$_1$-C$_6$ alkyl group, an optionally R$_b$-substituted C$_2$-C$_6$ alkenyl group, an optionally $R_b$-substituted $C_2$-$C_6$ alkynyl group, an optionally $R_b$-substituted $C_1$-$C_6$ alkoxy group, an optionally $R_c$-substituted $C_3$-$C_{10}$ cycloalkyl group, an optionally $R_c$-substituted $C_6$-$C_{14}$ aromatic hydrocarbon group, or an optionally $R_c$-substituted 4- to 10-membered saturated or unsaturated heterocyclic group.

5. The method of claim 1, wherein $R_1$ represents a cyclopentenyl group, a cyclohexenyl group, a phenyl group, a furanyl group, a 1H-pyrazolyl group, a thiazolyl group, an oxazolyl group, an isoxazolyl group, a 1,3,4-thiadiazolyl group, a 1,2,4-oxadiazolyl group, a 1,3,4-oxadiazolyl group, a pyridyl group, a dihydropyranyl group, a dihydrofuranyl group, or a 4,5-dihydro-1,3,4-oxadiazolyl group, which is optionally substituted with a group selected from the group consisting of a halogen atom, an amino group, a hydroxy group, an oxo group, an N-oxide group, a formyl group, a $C_1$-$C_6$ alkyl group (which is optionally substituted with a group selected from the group consisting of a hydroxy group and a di- or mono-($C_1$-$C_6$ alkyl)amino group), a $C_1$-$C_6$ alkoxy group (which is optionally substituted with a halogen atom), and a 4- to 10-membered saturated heterocyclic group.

6. The method of claim 1, wherein $R_1$ represents a cyclopentenyl group; a cyclohexenyl group; a phenyl group; a furanyl group, which is optionally substituted with a group selected from the group consisting of a formyl group and a $C_1$-$C_6$ alkyl group (which is optionally substituted with a group selected from the group consisting of a hydroxy group and a di- or mono-($C_1$-$C_6$ alkyl)amino group); a 1H-pyrazolyl group, which is optionally substituted with a group selected from the group consisting of a $C_1$-$C_6$ alkyl group and a 4- to 10-membered saturated heterocyclic group; a thiazolyl group; an oxazolyl group; an isoxazolyl group; a 1,3,4-thiadiazolyl group; a 1,2,4-oxadiazolyl group; a 1,3,4-oxadiazolyl group, which is optionally substituted with a $C_1$-$C_6$ alkyl group; a pyridyl group, which is optionally substituted with a group selected from the group consisting of a halogen atom, an amino group, a hydroxy group, an N-oxide group, a $C_1$-$C_6$ alkyl group (which is optionally substituted with a hydroxy group), and a $C_1$-$C_6$ alkoxy group (which is optionally substituted with a halogen atom); a dihydropyranyl group; a dihydrofuranyl group; or a 4,5-dihydro-1,3,4-oxadiazolyl group, which is optionally substituted with a group selected from the group consisting of an oxo group and a $C_1$-$C_6$ alkyl group.

7. The method of claim 1, wherein $R_2$ represents a hydrogen atom, a cyano group, —C(=O)O$R_x$, —C(=O)N($R_x$)($R_y$), an optionally $R_b$-substituted $C_1$-$C_6$ alkyl group, an optionally $R_b$-substituted $C_1$-$C_6$ alkoxy group, or an optionally $R_c$-substituted monocyclic 4- to 7-membered unsaturated heterocyclic group having 1 to 3 heteroatoms selected from the group consisting of N, S and O.

8. The method of claim 1, wherein $R_2$ represents a hydrogen atom; a cyano group; a ($C_1$-$C_6$ alkoxy)carbonyl group; a carbamoyl group; a di- or mono-($C_1$-$C_6$ alkyl)carbamoyl group; a $C_1$-$C_6$ alkyl group, which is optionally substituted with a group selected from the group consisting of a hydroxy group, a $C_1$-$C_6$ alkoxy group, a di- or mono-($C_1$-$C_6$ alkyl)amino group, and a 4- to 10-membered saturated heterocyclic group; a $C_1$-$C_6$ alkoxy group; or a monocyclic 5- or 6-membered completely unsaturated heterocyclic group having 1 to 3 N atoms, which is optionally substituted with a $C_1$-$C_6$ alkyl group.

9. The method of claim 1, wherein m represents 0, n represents 0 or 1, $R_4$ represents a $C_2$-$C_6$ alkenyl group, and in the formula (I), the structure:

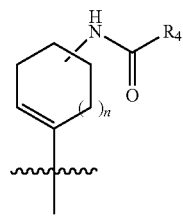

is any one of

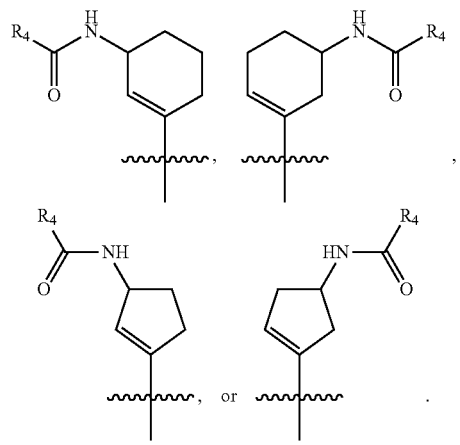

10. The method of claim 1,
wherein $R_1$ represents a cyclopentenyl group; a cyclohexenyl group; a phenyl group; a furanyl group, which is optionally substituted with a group selected from the group consisting of a formyl group and a $C_1$-$C_6$ alkyl group (which is optionally substituted with a group selected from the group consisting of a hydroxy group and a di- or mono-($C_1$-$C_6$ alkyl)amino group); a 1H-pyrazolyl group, which is optionally substituted with a group selected from the group consisting of a $C_1$-$C_6$ alkyl group and a 4- to 10-membered saturated heterocyclic group; a thiazolyl group; an oxazolyl group; an isoxazolyl group; a 1,3,4-thiadiazolyl group; a 1,2,4-oxadiazolyl group; a 1,3,4-oxadiazolyl group, which is optionally substituted with a $C_1$-$C_6$ alkyl group; a pyridyl group, which is optionally substituted with a group selected from the group consisting of a halogen atom, an amino group, a hydroxy group, an N-oxide group, a $C_1$-$C_6$ alkyl group (which is optionally substituted with a hydroxy group), and a $C_1$-$C_6$ alkoxy group (which is optionally substituted with a halogen atom); a dihydropyranyl group; a dihydrofuranyl group; or a 4,5-dihydro-1,3,4-oxadiazolyl group, which is optionally substituted with a group selected from the group consisting of an oxo group and a $C_1$-$C_6$ alkyl group,
$R_2$ represents a hydrogen atom; a cyano group; a ($C_1$-$C_6$ alkoxy)carbonyl group; a carbamoyl group; a di- or mono-($C_1$-$C_6$ alkyl)carbamoyl group; a $C_1$-$C_6$ alkyl group, which is optionally substituted with a group selected from the group consisting of a hydroxy group, a $C_1$-$C_6$ alkoxy group, a di- or mono-($C_1$-$C_6$ alkyl) amino group, and a 4- to 10-membered saturated heterocyclic group; a $C_1$-$C_6$ alkoxy group; or a monocyclic 5- or 6-membered completely unsaturated heterocyclic group having 1 to 3 N atoms, which is optionally substituted with a $C_1$-$C_6$ alkyl group, m represents 0, n represents 0 or 1, $R_4$ represents a $C_2$-$C_6$ alkenyl group, and in the formula (I), the structure:

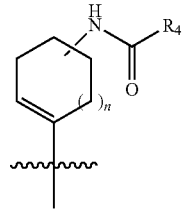

is any one of:

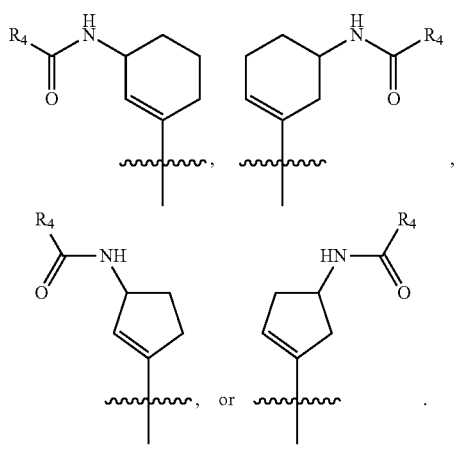

11. The method of claim 1, wherein the compound of the formula (I) is selected from the group consisting of:
(1) N-(3-(3-phenyl-1H-pyrrolo[2,3-b]pyridin-4-yl)cyclohex-3-en-1-yl)acrylamide,
(2) N-(3-(3-(1H-pyrazol-4-yl)-1H-pyrrolo[2,3-b]pyridin-4-yl)cyclohex-3-en-1-yl)acrylamide,
(3) N-(3-(3-(2-methoxypyridin-3-yl)-1H-pyrrolo[2,3-b]pyridin-4-yl)cyclohex-3-en-1-yl)acrylamide,
(4) N-(3-(3-(furan-2-yl)-1H-pyrrolo[2,3-b]pyridin-4-yl)cyclohex-3-en-1-yl)acrylamide,
(5) N-(3-(3-(4-(hydroxymethyl)furan-2-yl)-1H-pyrrolo[2,3-b]pyridin-4-yl)cyclohex-3-en-1-yl)acrylamide,
(6) N-(3-(3-(2,5-dihydrofuran-3-yl)-1H-pyrrolo[2,3-b]pyridin-4-yl)cyclohex-3-en-1-yl)acrylamide,
(7) N-(3-(3-(oxazol-5-yl)-1H-pyrrolo[2,3-b]pyridin-4-yl)cyclohex-3-en-1-yl)acrylamide,
(8) N-(3-(3-(1,3,4-oxadiazol-2-yl)-1H-pyrrolo[2,3-b]pyridin-4-yl)cyclohex-3-en-1-yl)acrylamide,
(9) (S)-N-(3-(3-(1,3,4-oxadiazol-2-yl)-1H-pyrrolo[2,3-b]pyridin-4-yl)cyclohex-3-en-1-yl)acrylamide,
(10) N-(3-(3-(1,3,4-oxadiazol-2-yl)-1H-pyrrolo[2,3-b]pyridin-4-yl)cyclopent-3-en-1-yl)acrylamide, and
(11) (S)-N-(3-(3-(isoxazol-5-yl)-1H-pyrrolo[2,3-b]pyridin-4-yl)cyclohex-3-en-1-yl)acrylamide.

12. A method for treating multiple sclerosis, comprising:
administering a compound of the formula (I) or a salt thereof to a subject in need thereof,

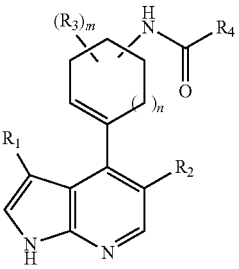

wherein:
$R_1$ represents an optionally substituted $C_4$-$C_{10}$ cycloalkyl group, an optionally substituted $C_4$-$C_{10}$ cycloalkenyl group, an optionally substituted $C_4$-$C_{10}$ cycloalkynyl group, an optionally substituted $C_6$-$C_{14}$ aromatic hydrocarbon group, or an optionally substituted 4- to 10-membered saturated or unsaturated heterocyclic group;

$R_2$ represents a hydrogen atom, a halogen atom, a hydroxy group, a cyano group, a nitro group, —C(=O)$R_x$, —C(=O)O$R_x$, —C(=O)N($R_x$)($R_y$), —N($R_x$)($R_y$), —$NR_x$C(=O)$R_y$, —$NR_x$S(=O)$_2R_y$, —$NR_x$C(=O)O$R_y$, —$NR_x$C(=O)N($R_y$)($R_z$), —$NR_x$S(=O)$_2$N($R_y$)($R_z$), —OC(=O)$R_x$, —OC(=O)O$R_x$, —OC(=O)N($R_x$)($R_y$), —S$R_x$, —S(=O)$_2R_x$, —S(=O)$_2$O$R_x$, an optionally $R_b$-substituted $C_1$-$C_6$ alkyl group, an optionally $R_b$-substituted $C_2$-$C_6$ alkenyl group, an optionally $R_b$-substituted $C_2$-$C_6$ alkynyl group, an optionally $R_b$-substituted $C_1$-$C_6$ alkoxy group, an optionally $R_c$-substituted $C_3$-$C_{10}$ cycloalkyl group, an optionally $R_c$-substituted $C_6$-$C_{14}$ aromatic hydrocarbon group, or an optionally $R_c$-substituted 4- to 10-membered saturated or unsaturated heterocyclic group;

$R_3$ represents a halogen atom, an amino group, a hydroxy group, a cyano group, a nitro group, a $C_1$-$C_6$ alkyl group, a $C_2$-$C_6$ alkenyl group, a $C_2$-$C_6$ alkynyl group, or a $C_1$-$C_6$ alkoxy group;

$R_4$ represents an optionally $R_b$-substituted $C_2$-$C_6$ alkenyl group or an optionally $R_b$-substituted $C_2$-$C_6$ alkynyl group;

$R_b$ represents a halogen atom, an amino group, a hydroxy group, a cyano group, a nitro group, a $C_1$-$C_6$ alkoxy group, a di- or mono-($C_1$-$C_6$ alkyl)amino group, or a 4- to 10-membered saturated or unsaturated heterocyclic group;

$R_c$ represents a halogen atom, an amino group, a hydroxy group, a cyano group, a nitro group, an oxo group, an imino group, an N-oxide group, a $C_1$-$C_6$ alkyl group, a $C_2$-$C_6$ alkenyl group, a $C_2$-$C_6$ alkynyl group, a $C_1$-$C_6$ alkoxy group, or a di- or mono-($C_1$-$C_6$ alkyl)amino group;

$R_x$, $R_y$, and $R_z$, which are the same or different, each represent a hydrogen atom, a $C_1$-$C_6$ alkyl group, a $C_1$-$C_6$ haloalkyl group, a $C_2$-$C_6$ alkenyl group, a $C_2$-$C_6$ alkynyl group, a $C_3$-$C_{10}$ cycloalkyl group, a $C_6$-$C_{14}$ aromatic hydrocarbon group, or a 4- to 10-membered saturated or unsaturated heterocyclic group;

m represents an integer of 0 to 3; and n represents an integer of 0 to 2.

13. The method of claim 12,
wherein a group with which the $C_4$-$C_{10}$ cycloalkyl group, $C_4$-$C_{10}$ cycloalkenyl group, $C_4$-$C_{10}$ cycloalkynyl group, $C_6$-$C_{14}$ aromatic hydrocarbon group or 4- to 10-membered saturated or unsaturated heterocyclic group, which is represented by $R_1$, is optionally substituted is $R_a$, and $R_a$ represents a halogen atom, a hydroxy group, a cyano group, a nitro group, an oxo group, an N-oxide group, —C(=O)$R_x$, —C(=O)O$R_x$, —C(=O)N($R_x$)($R_y$), —C(=O)S$R_x$, —C(=S)O$R_x$, —C(=O)ON($R_x$)($R_y$), —N($R_x$)($R_y$), —N$R_x$C(=O)$R_y$, —N$R_x$S(=O)$_2R_y$, —N$R_x$C(=O)O$R_y$, —N$R_x$C(=O)N($R_y$)($R_z$), —N$R_x$S(=O)$_2$N($R_y$)($R_z$), —N($R_x$)—O$R_y$, =N$R_x$, =N—O$R_x$, —OC(=O)$R_x$, —OC(=S)$R_x$, —OC(=O)O$R_x$, —OC(=O)N($R_x$)($R_y$), —OC(=S)O$R_x$, —S$R_x$, —S(=O)$_2R_x$, —S(=O)$_2$O$R_x$, —S(=O)$_2$N($R_x$)($R_y$), an optionally $R_b$-substituted $C_1$-$C_6$ alkyl group, an optionally $R_b$-substituted $C_2$-$C_6$ alkenyl group, an optionally $R_b$-substituted $C_2$-$C_6$ alkynyl group, an optionally $R_b$-substituted $C_1$-$C_6$ alkoxy group, an optionally $R_c$-substituted $C_3$-$C_{10}$ cycloalkyl group, an optionally $R_c$-substituted $C_6$-$C_{14}$ aromatic hydrocarbon group, or an optionally $R_c$-substituted 4- to 10-membered saturated or unsaturated heterocyclic group.

14. The method of claim 12, wherein $R_1$ represents an optionally $R_a$-substituted $C_5$-$C_7$ cycloalkenyl group, an optionally $R_a$-substituted $C_6$-$C_{10}$ aromatic hydrocarbon group, or an optionally $R_a$-substituted monocyclic 4- to 7-membered unsaturated heterocyclic group having 1 to 3 heteroatoms selected from the group consisting of N, S and O, and $R_a$ represents a halogen atom, a hydroxy group, a cyano group, a nitro group, an oxo group, an N-oxide group, —C(=O)$R_x$, —C(=O)O$R_x$, —C(=O)N($R_x$)($R_y$), —C(=O)S$R_x$, —C(=S)O$R_x$, —C(=O)ON($R_x$)($R_y$), —N($R_x$)($R_y$), —N$R_x$C(=O)$R_y$, —N$R_x$S(=O)$_2R_y$, —N$R_x$C(=O)O$R_y$, —N$R_x$C(=O)N($R_y$)($R_z$), —N$R_x$S(=O)$_2$N($R_y$)($R_z$), —N($R_x$)—O$R_y$, =N$R_x$, =N—O$R_x$, —OC(=O)$R_x$, —OC(=S)$R_x$, —OC(=O)O$R_x$, —OC(=O)N($R_x$)($R_y$), —OC(=S)O$R_x$, —S$R_x$, —S(=O)$_2R_x$, —S(=O)$_2$O$R_x$, —S(=O)$_2$N($R_x$)($R_y$), an optionally $R_b$-substituted $C_1$-$C_6$ alkyl group, an optionally $R_b$-substituted $C_2$-$C_6$ alkenyl group, an optionally $R_b$-substituted $C_2$-$C_6$ alkynyl group, an optionally $R_b$-substituted $C_1$-$C_6$ alkoxy group, an optionally $R_c$-substituted $C_3$-$C_{10}$ cycloalkyl group, an optionally $R_c$-substituted $C_6$-$C_{14}$ aromatic hydrocarbon group, or an optionally $R_c$-substituted 4- to 10-membered saturated or unsaturated heterocyclic group.

15. The method of claim 12, wherein $R_1$ represents an optionally $R_a$-substituted cyclopentenyl group, cyclohexenyl group, phenyl group, furanyl group, 1H-pyrazolyl group, thiazolyl group, oxazolyl group, isoxazolyl group, 1,3,4-thiadiazolyl group, 1,2,4-oxadiazolyl group, 1,3,4-oxadiazolyl group, pyridyl group, dihydropyranyl group, dihydrofuranyl group, or 4,5-dihydro-1,3,4-oxadiazolyl group, and $R_a$ represents a halogen atom, a hydroxy group, a cyano group, a nitro group, an oxo group, an N-oxide group, —C(=O)$R_x$, —C(=O)O$R_x$, —C(=O)N($R_x$)($R_y$), —C(=O)S$R_x$, —C(=S)O$R_x$, —C(=O)ON($R_x$)($R_y$), —N($R_x$)($R_y$), —N$R_x$C(=O)$R_y$, —N$R_x$S(=O)$_2R_y$, —N$R_x$C(=O)O$R_y$, —N$R_x$C(=O)N($R_y$)($R_z$), —N$R_x$S(=O)$_2$N($R_y$)($R_z$), —N($R_x$)—O$R_y$, =N$R_x$, =N—O$R_x$, —OC(=O)$R_x$, —OC(=S)$R_x$, —OC(=O)O$R_x$, —OC(=O)N($R_x$)($R_y$), —OC(=S)O$R_x$, —S$R_x$, —S(=O)$_2R_x$, —S(=O)$_2$O$R_x$, —S(=O)$_2$N($R_x$)($R_y$), an optionally $R_b$-substituted $C_1$-$C_6$ alkyl group, an optionally $R_b$-substituted $C_2$-$C_6$ alkenyl group, an optionally $R_b$-substituted $C_2$-$C_6$ alkynyl group, an optionally $R_b$-substituted $C_1$-$C_6$ alkoxy group, an optionally $R_c$-substituted $C_3$-$C_{10}$ cycloalkyl group, an optionally $R_c$-substituted $C_6$-$C_{14}$ aromatic hydrocarbon group, or an optionally $R_c$-substituted 4- to 10-membered saturated or unsaturated heterocyclic group.

16. The method of claim 12, wherein $R_1$ represents a cyclopentenyl group, a cyclohexenyl group, a phenyl group, a furanyl group, a 1H-pyrazolyl group, a thiazolyl group, an oxazolyl group, an isoxazolyl group, a 1,3,4-thiadiazolyl group, a 1,2,4-oxadiazolyl group, a 1,3,4-oxadiazolyl group, a pyridyl group, a dihydropyranyl group, a dihydrofuranyl group, or a 4,5-dihydro-1,3,4-oxadiazolyl group, which is optionally substituted with a group selected from the group consisting of a halogen atom, an amino group, a hydroxy group, an oxo group, an N-oxide group, a formyl group, a $C_1$-$C_6$ alkyl group (which is optionally substituted with a group selected from the group consisting of a hydroxy group and a di- or mono-($C_1$-$C_6$ alkyl)amino group), a $C_1$-$C_6$ alkoxy group (which is optionally substituted with a halogen atom), and a 4- to 10-membered saturated heterocyclic group.

17. The method of claim 12, wherein $R_1$ represents a cyclopentenyl group; a cyclohexenyl group; a phenyl group; a furanyl group, which is optionally substituted with a group selected from the group consisting of a formyl group and a $C_1$-$C_6$ alkyl group (which is optionally substituted with a group selected from the group consisting of a hydroxy group and a di- or mono-($C_1$-$C_6$ alkyl)amino group); a 1H-pyrazolyl group, which is optionally substituted with a group selected from the group consisting of a $C_1$-$C_6$ alkyl group and a 4- to 10-membered saturated heterocyclic group; a thiazolyl group; an oxazolyl group; an isoxazolyl group; a 1,3,4-thiadiazolyl group; a 1,2,4-oxadiazolyl group; a 1,3,4-oxadiazolyl group, which is optionally substituted with a $C_1$-$C_6$ alkyl group; a pyridyl group, which is optionally substituted with a group selected from the group consisting of a halogen atom, an amino group, a hydroxy group, an N-oxide group, a $C_1$-$C_6$ alkyl group (which is optionally substituted with a hydroxy group), and a $C_1$-$C_6$ alkoxy group (which is optionally substituted with a halogen atom); a dihydropyranyl group; a dihydrofuranyl group; or a 4,5-dihydro-1,3,4-oxadiazolyl group, which is optionally substituted with a group selected from the group consisting of an oxo group and a $C_1$-$C_6$ alkyl group.

18. The method of claim 12, wherein $R_2$ represents a hydrogen atom, a cyano group, —C(=O)O$R_x$, —C(=O)N($R_x$)($R_y$), an optionally $R_b$-substituted $C_1$-$C_6$ alkyl group, an optionally $R_b$-substituted $C_1$-$C_6$ alkoxy group, or an optionally $R_c$-substituted monocyclic 4- to 7-membered unsaturated heterocyclic group having 1 to 3 heteroatoms selected from the group consisting of N, S and O.

19. The method of claim 12, wherein $R_2$ represents a hydrogen atom; a cyano group; a ($C_1$-$C_6$ alkoxy)carbonyl group; a carbamoyl group; a di- or mono-($C_1$-$C_6$ alkyl)carbamoyl group; a $C_1$-$C_6$ alkyl group, which is optionally substituted with a group selected from the group consisting of a hydroxy group, a $C_1$-$C_6$ alkoxy group, a di- or mono-($C_1$-$C_6$ alkyl)amino group, and a 4- to 10-membered saturated heterocyclic group; a $C_1$-$C_6$ alkoxy group; or a monocyclic 5- or 6-membered completely unsaturated heterocyclic group having 1 to 3 N atoms, which is optionally substituted with a $C_1$-$C_6$ alkyl group.

20. The method of claim 12, wherein m represents 0, n represents 0 or 1, $R_4$ represents a $C_2$-$C_6$ alkenyl group, and in the formula (I), the structure:

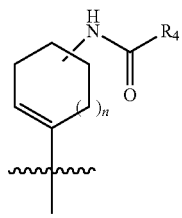

is any one of

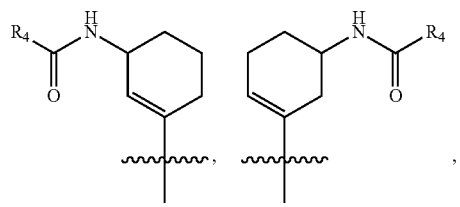

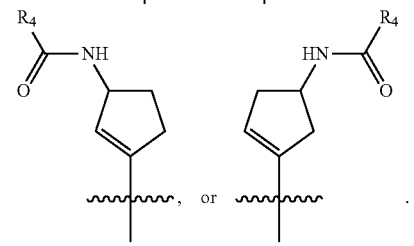

21. The method of claim 12,
wherein $R_1$ represents a cyclopentenyl group; a cyclohexenyl group; a phenyl group; a furanyl group, which is optionally substituted with a group selected from the group consisting of a formyl group and a $C_1$-$C_6$ alkyl group (which is optionally substituted with a group selected from the group consisting of a hydroxy group and a di- or mono-($C_1$-$C_6$ alkyl)amino group); a 1H-pyrazolyl group, which is optionally substituted with a group selected from the group consisting of a $C_1$-$C_6$ alkyl group and a 4- to 10-membered saturated heterocyclic group; a thiazolyl group; an oxazolyl group; an isoxazolyl group; a 1,3,4-thiadiazolyl group; a 1,2,4-oxadiazolyl group; a 1,3,4-oxadiazolyl group, which is optionally substituted with a $C_1$-$C_6$ alkyl group; a pyridyl group, which is optionally substituted with a group selected from the group consisting of a halogen atom, an amino group, a hydroxy group, an N-oxide group, a $C_1$-$C_6$ alkyl group (which is optionally substituted with a hydroxy group), and a $C_1$-$C_6$ alkoxy group (which is optionally substituted with a halogen atom); a dihydropyranyl group; a dihydrofuranyl group; or a 4,5-dihydro-1,3,4-oxadiazolyl group, which is optionally substituted with a group selected from the group consisting of an oxo group and a $C_1$-$C_6$ alkyl group,
$R_2$ represents a hydrogen atom; a cyano group; a ($C_1$-$C_6$ alkoxy)carbonyl group; a carbamoyl group; a di- or mono-($C_1$-$C_6$ alkyl)carbamoyl group; a $C_1$-$C_6$ alkyl group, which is optionally substituted with a group selected from the group consisting of a hydroxy group, a $C_1$-$C_6$ alkoxy group, a di- or mono-($C_1$-$C_6$ alkyl) amino group, and a 4- to 10-membered saturated heterocyclic group; a $C_1$-$C_6$ alkoxy group; or a monocyclic 5- or 6-membered completely unsaturated heterocyclic group having 1 to 3 N atoms, which is optionally substituted with a $C_1$-$C_6$ alkyl group,
m represents 0, n represents 0 or 1, $R_4$ represents a $C_2$-$C_6$ alkenyl group, and
in the formula (1), the structure:

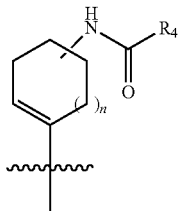

is any one of:

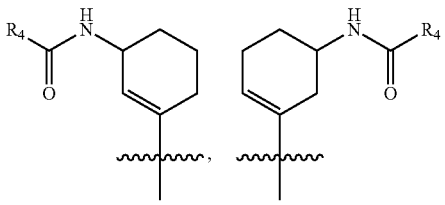

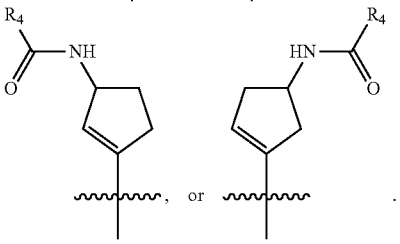

22. The method of claim 12, wherein the compound of the formula (I) is selected from the group consisting of:
(1) N-(3-(3-phenyl-1H-pyrrolo[2,3-b]pyridin-4-yl)cyclohex-3-en-1-yl)acrylamide,
(2) N-(3-(3-(1H-pyrazol-4-yl)-1H-pyrrolo[2,3-b]pyridin-4-yl)cyclohex-3-en-1-yl)acrylamide,
(3) N-(3-(3-(2-methoxypyridin-3-yl)-1H-pyrrolo[2,3-b]pyridin-4-yl)cyclohex-3-en-1-yl)acrylamide,
(4) N-(3-(3-(furan-2-yl)-1H-pyrrolo[2,3-b]pyridin-4-yl)cyclohex-3-en-1-yl)acrylamide,
(5) N-(3-(3-(4-(hydroxymethyl)furan-2-yl)-1H-pyrrolo[2,3-b]pyridin-4-yl)cyclohex-3-en-1-yl)acrylamide,
(6) N-(3-(3-(2,5-dihydrofuran-3-yl)-1H-pyrrolo[2,3-b]pyridin-4-yl)cyclohex-3-en-1-yl)acrylamide,
(7) N-(3-(3-(oxazol-5-yl)-1H-pyrrolo[2,3-b]pyridin-4-yl)cyclohex-3-en-1-yl)acrylamide,
(8) N-(3-(3-(1,3,4-oxadiazol-2-yl)-1H-pyrrolo[2,3-b]pyridin-4-yl)cyclohex-3-en-1-yl)acrylamide,
(9) (S)-N-(3-(3-(1,3,4-oxadiazol-2-yl)-1H-pyrrolo[2,3-b]pyridin-4-yl)cyclohex-3-en-1-yl)acrylamide,
(10) N-(3-(3-(1,3,4-oxadiazol-2-yl)-1H-pyrrolo[2,3-b]pyridin-4-yl)cyclopent-3-en-1-yl)acrylamide, and
(11) (S)-N-(3-(3-(isoxazol-5-yl)-1H-pyrrolo[2,3-b]pyridin-4-yl)cyclohex-3-en-1-yl)acrylamide.

* * * * *